US007759304B2

(12) United States Patent
Gilkeson et al.

(10) Patent No.: US 7,759,304 B2
(45) Date of Patent: Jul. 20, 2010

(54) TARGETING COMPLEMENT FACTOR H FOR TREATMENT OF DISEASES

(75) Inventors: Gary Gilkeson, Charleston, SC (US); Stephen Tomlinson, Mount Pleasant, SC (US); V. Michael Holers, Denver, CO (US); Baerbel Rohrer, Mount Pleasant, SC (US)

(73) Assignees: Regents of the University of Colorado, Boulder, CO (US); MUSC Foundation For Research Development, Charleston, SC (US)

( * ) Notice: Subject to any disclaimer, the term of this patent is extended or adjusted under 35 U.S.C. 154(b) by 0 days.

(21) Appl. No.: 11/821,370

(22) Filed: Jun. 21, 2007

(65) Prior Publication Data

US 2008/0221011 A1 Sep. 11, 2008

Related U.S. Application Data

(60) Provisional application No. 60/815,748, filed on Jun. 21, 2006.

(51) Int. Cl.
*C07K 14/00* (2006.01)
(52) U.S. Cl. .................. 514/2; 530/350; 435/320.1; 435/325
(58) Field of Classification Search .................. None
See application file for complete search history.

(56) References Cited

U.S. PATENT DOCUMENTS

| 4,883,784 | A | 11/1989 | Kaneko |
| 5,212,071 | A | 5/1993 | Fearon et al. |
| 5,328,470 | A | 7/1994 | Nabel et al. |
| 5,472,939 | A | 12/1995 | Fearon et al. |
| 5,679,546 | A | 10/1997 | Ko et al. |
| 5,851,528 | A | 12/1998 | Ko et al. |
| 5,981,481 | A | 11/1999 | Fearon et al. |
| 6,140,472 | A | 10/2000 | Rosengard et al. |
| 6,214,966 | B1 | 4/2001 | Harris |
| 6,248,365 | B1 | 6/2001 | Römisch et al. |
| 6,291,239 | B1 | 9/2001 | Prodinger et al. |
| 6,432,679 | B1 | 8/2002 | Mond et al. |
| 6,458,360 | B1 | 10/2002 | Fearon et al. |
| 6,503,947 | B1 | 1/2003 | Lipton et al. |
| 6,521,450 | B1 | 2/2003 | Atkinson et al. |
| 6,820,011 | B2 | 11/2004 | Chen et al. |
| 6,897,290 | B1 | 5/2005 | Atkinson et al. |
| 2004/0005538 | A1 | 1/2004 | Chen et al. |
| 2005/0260198 | A1 | 11/2005 | Holers et al. |
| 2005/0265995 | A1 | 12/2005 | Tomlinson et al. |
| 2006/0002944 | A1 | 1/2006 | Ashkenazi et al. |
| 2006/0014681 | A1 | 1/2006 | Chen et al. |
| 2006/0178308 | A1 | 8/2006 | Schwaeble et al. |
| 2006/0263819 | A1 | 11/2006 | Hageman et al. |
| 2006/0292141 | A1 | 12/2006 | Holers et al. |
| 2007/0020647 | A1 | 1/2007 | Hageman et al. |
| 2008/0267980 | A1 | 10/2008 | Tomlinson et al. |

FOREIGN PATENT DOCUMENTS

| EP | 0 402 226 A1 | 12/1990 |
| WO | WO-91/16437 A1 | 10/1991 |
| WO | WO-2004/045520 A2 | 6/2004 |
| WO | WO-2004/045520 A3 | 6/2004 |
| WO | WO-2004/103288 A2 | 12/2004 |
| WO | WO-2004/103288 A3 | 12/2004 |
| WO | WO-2005/077417 A1 | 8/2005 |
| WO | WO-2006/062716 A2 | 6/2006 |
| WO | WO-2006/062716 A3 | 6/2006 |
| WO | WO-2006/083533 A2 | 8/2006 |
| WO | WO-2006/088950 A2 | 8/2006 |
| WO | WO-2006/088950 A3 | 8/2006 |
| WO | WO-2006/088950 B1 | 8/2006 |
| WO | WO-2006/128006 A1 | 11/2006 |
| WO | WO-2007/029008 A2 | 3/2007 |
| WO | WO-2007/029008 A3 | 3/2007 |
| WO | WO-2007/056227 A2 | 5/2007 |

OTHER PUBLICATIONS

Moore et al. 1991; Inhibition of Epstein-Barr virus infection in vitro and in vivo by soluble CR2 (CD21) containing two short consensus repeats. J. Virology 65(7): 3559-3565.*

Mold et al. 1988; Activation of the alternative complement pathway by EBV and the viral envelope glycoprotein gp350. J. Immunology 140(11): 3867-3874.*

Amsterdam, E.A. et al. (Jan. 1995). "Limitation of Reperfusion Injury by a Monoclonal Antibody to C5a During Myocardial Infarction in Pigs," *American Journal of Physiology* 268(1):H448-H457.

de Córdoba, S.R. et al. (2004). "The Human Complement Factor H: Functional Roles, Genetic Variations and Disease Associations," *Molecular Immunology* 41:355-367.

Edwards, A.O. et al. (Apr. 15, 2005). "Complement Factor H Polymorphism and Age-Related Macular Degeneration," *Science* 308:421-424.

Girardi, G. et al. (Dec. 2003). "Complement C5a Receptors and Neurophils Mediate Fetal Injury in the Antiphospholipid Syndrome," *The Journal of Clinical Investigation* 112(11):1644-1654.

Hageman, G.S. et al. (May 17, 2005). "A Common Haplotype in the Complement Regulatory Gene Factor H (HF1/CFH) Predisposes Individuals to Age-Related Macular Degeneration," *Proc. Natl. Acad. Sci USA* 102(20):7227-7232.

Haines, J.L. et al. (Apr. 15, 2005). "Complement Factor H Variant Increases the Risk of Age-Related Macular Degeneration," *Science* 308(5720):419-421.

Homeister, J.W. et al. (Feb. 1, 1993). "Soluble Complement Receptor Type 1 Prevents Complement-Mediated Damage of the Rabbit Isolated Heart," *The Journal of Immunology* 150(3):1055-1064.

(Continued)

*Primary Examiner*—Karen Cochrane Carlson
(74) *Attorney, Agent, or Firm*—Morrison & Foerster LLP

(57) ABSTRACT

The invention provides a CR2-FH molecule comprising a CR2 portion comprising CR2 protein or a fragment thereof and a FH portion comprising a factor H protein or a fragment thereof, and pharmaceutical compositions comprising a CR2-FH molecule. Also provided are methods of using the compositions for treatment diseases in which the alternative complement pathway is implicated, such as age-related macular degeneration, rheumatoid arthritis, and ischemia reperfusion.

20 Claims, 24 Drawing Sheets

OTHER PUBLICATIONS

Jozsi, M. et al. (2004). "Attachment of the Soluble Complement Regulator Factor H to Cell and Tissue Surfaces: Relevance for Pathology," *Histol. Histopathol.* 19:251-258.

Klein, R.J. et al. (Apr. 15, 2005). "Complement Factor H Polymorphism in Age-Related Macular Degeneration," *Science* 308(5720):385-389.

Kroshus, T.J. et al. (Dec. 15, 1995). "Complement Inhibition with an Anti-C5 Monoclonal Antibody Prevents Acute Cardiac Tissue Injury in an Ex Vivo Model of Pig-to-Human Xenotransplantation," *Transplantation* 60(11):1194-1202.

Lyubarsky, A.L. et al. (Jan. 15, 1996). "Recovery Phase of the Murine Rod Photoresponse Reconstructed from Electroretinographic Recordings," *The Journal of Neuroscience* 16(2):563-571.

Molina, H. et al. (Jul. 15, 1994). "Analysis of C3b/C3d Binding Sites and Factor 1 Cofactor Regions Within Mouse Complement Receptors 1 and 2," *The Journal of Immunology* 153(2):789-795.

Morgan, B.P. (Apr. 1994). "Clinical Complementology: Recent Progress and Future Trends," *European Journal of Clinical Investigation* 24(4):219-228.

Müller-Eberhard, H.J. (1988). "Molecular Organization and Function of the Complement System," *Ann. Rev. Biochem.* 57:321-347.

Nozaki, M. et al. (Feb. 14, 2006). "Drusen Complement Components C3a and C5a Promote Choroidal Neovascularization," *Proc. Natl. Acad. Sci. USA* 103(7):2328-2333.

Quigg, R.J. et al. (May 1, 1998). "Blockade of Antibody-Induced Glomerulonephritis with Crry-Ig, a Soluble Murine Complement Inhibitor," *The Journal of Immunology* 160(9):4553-4560.

Rabinovici, R. et al. (Sep. 1, 1992). "Role of Complement in Endotoxin/Platelet-Activating Factor-Induced Lung Injury," *The Journal of Immunology* 149(5):1744-1750.

Rinder, C.S. et al. (Sep. 1995). "Blockade of C5a and C5b-9 Generation Inhibits Leukocyte and Platelet Activation During Extracorporeal Circulation," *The Journal of Clinical Investigation* 96(3):1564-1572.

Rohrer, B. et al. (Oct. 15, 1999). "Role of Neurotrophin Receptor TrkB in the Maturation of Rod Photoreceptors and Establishment of Synaptic Transmission to the Inner Retina," *The Journal of Neuroscience* 19(20):8919-8930.

Tsutsumi, Y. et al. (Jul. 18, 2000) "Site-specific Chemical Modification with Polyethylene Glycol of Recombinant Immunotoxin Anti-Tac(Fv)-PE38 (LMB-2) Improves Antitumor Activity and Reduces Animal Toxicity and Immunogenicity," *Proc. Natl. Acad. Sci. USA* 97(15):8548-8553.

U.S. Appl. No. 10/534,772, filed May 13, 2005, by Tomlinson et al.

U.S. Appl. No. 11/786,788, filed Apr. 12, 2007, by Chen et al.

Wang, Y. et al. (Sep. 12, 1995). "Anti-C5 Monoclonal Antibody Therapy Prevents Collagen-Induced Arthritis and Ameliorates Established Disease," *Proc. Natl. Acad. Sci. USA* 92(19):8955-8959.

Wang, Y. et al. (Aug. 6, 1996). "Amelioration of Lupus-Like Autoimmune Disease in NZB/W $F_1$ Mice After Treatment With a Blocking Monoclonal Antibody Specific for Complement Component C5," *Proc. Natl. Acad. Sci. USA* 93(16):8563-8568.

Weisman, H.F. et al. (Jul. 13, 1990). "Soluble Human Complement Receptor Type 1: In Vivo Inhibitor of Complement Suppressing Post-Ischemic Myocardial Inflammation and Necrosis," *Science* 249(4965):146-151.

Zipfel, P.F. (Jun. 2001). "Complement Factor H: Physiology and Pathophysiology," *Seminars in Thrombosis and Hemostasis* 27(3):191-199.

Ahearn, J.H. et al. (Mar. 1996). "Disruption of the *Cr2* Locus Results in a Reduction in B-1a Cells and in an Impaired B Cell Response to T-Dependent Antigen," *Immunity* 4(3):251-262.

Andrews, B.S. et al. (Nov. 1978). "Spontaneous Murine Lupus-like Syndromes. Clinical and Immunopathological Manifestations in Several Strains," *J. Exp. Med.* 148:1198-1215.

Aslam, M. et al. (Jun. 22, 2001). "Folded-Back Solution Structure of Monomeric Factor H of Human Complement by Synchrotron X-ray and Neutron Scattering, Analytical Ultracentrifugation and Constrained Molecular Modelling," *J. Mol. Biol.* 309(5):1117-1138.

Aubry, J-P. et al. (Aug. 6, 1992). "CD21 is a Ligand for CD23 and Regulates IgE Production," *Nature* 358 (6386):505-507.

Baranyi, L. et al. (Aug. 1994). "Cell-Surface Bound Complement Regulatory Activity is Necessary for the in vivo Survival of KDH-8 Rat Hepatoma," *Immunology* 82(4):522-528.

Barlow, P.N. et al. (Jul. 5, 1993). "Solution Structure of a Pair of Complement Modules by Nuclear Magnetic Resonance," *J. Mol. Biol.* 232(1):268-284.

Bergelson, J.M. et al. (Jun. 1994). "Decay-Accelerating Factor (CD55), a Glycosylphosphatidylinositol-Anchored Complement Regulatory Protein, is a Receptor for Several Echoviruses," *PNAS* 91(13):6245-6248.

Cambier, J.C. (May 1997). "Signalling Processes in Haematopoietic Cells: Positive and Negative Signal Co-operativity in the Immune System: The BCR, FcγRIIB, CR2 Paradigm," *Biochem. Soc. Trans.* 25(2):441-445.

Caragine, T.A. et al. (Feb. 15, 2002). "A Tumor-Expressed Inhibitor of the Early but not Late Complement Lytic Pathway Enhances Tumor Growth in a Rat Model of Human Breast Cancer," *Cancer Res.* 62(4):1110-1115.

Carel, J.C. et al. (Jul. 25, 1990). "Structural Requirements for C3d,g/Epstein-Barr Virus Receptor (CR2/CD21) Ligand Binding, Internalization, and Viral Infection," *J. Biol. Chem.* 265(21):12293-12299.

Carroll, M.C. (1998). "The Role of Complement and Complement Receptors in Induction and Regulation of Immunity," *Annu. Rev. Immunol.* 16:545-568.

Carroll, M.C. (2000). "The Role of Complement in B Cell Activation and Tolerance" *Adv. Immunol.* 74:61-88.

Carter, R.H. et al. (Apr. 3, 1992). "CD19: Lowering the Threshold for Antigen Receptor Stimulation of B Lymphocytes," *Science* 256:105-107.

Casasnovas, J.M. et al. (1999). "Crystal Structure of Two CD46 Domains Reveals an Extended Measles Virus-Binding Surface," *EMBO J.* 18(11):2911-2922.

Chen, S. et al. (Jun. 1, 2000). "CD59 Expressed on a Tumor Cell Surface Modulates Decay-accelerating Factor Expression and Enhances Tumor Growth in a Rat Model of Human Neuroblastoma," *Cancer Res.* 60(11):3013-3018.

Christiansen, D. et al. (Mar. 1996). "A Functional Analysis of Recombinant Soluble CD46 in vivo and a Comparison with Recombinant Soluble Forms of CD55 and CD35 in vitro," *Eur. J. Immunol.* 26(3):578-585.

Clemenza, L. et al. (Oct. 1, 2000). "Structure-Guided Identification of C3d Residues Essential for Its Binding to Complement Receptor 2 (CD21)," *J. Immunol.* 165(7):3839-3848.

Davies, A. et al. (Sep. 1, 1989). "CD59, an Ly-6-Like Protein Expressed in Human Lymphoid Cells, Regulates the Action of the Complement Membrane Attack Complex on Homologous Cells," *J. Exp. Med.* 170(3):637-654.

Dempsey, P.W. et al. (Jan. 19, 1996). "C3d of Complement as a Molecular Adjuvant: Bridging Innate and Acquired Immunity,"*Science* 271:348-350.

Diefenbach, R.J. et al. (Mar. 1, 1995). "Mutation of Residues in the C3dg Region of Human Complement Component C3 Corresponding to a Proposed Binding Site for Complement Receptor Type 2 (CR2, CD21) Does Not Abolish Binding of iC3b or C3dg to CR2," *J. Immunol.* 154(5):2303-2320.

Dierich, M.P. et al. (Nov. 1988). "Structural and Functional Relationships Among Receptors and Regulators of the Complement System," *Mol. Immunol.* 25(11):1043-1051.

Dörig, R.E. et al. (Oct. 22, 1993). "The Human CD46 Molecule Is a Receptor for Measles Virus (Edmonston Strain)," *Cell* 75(2):295-305.

Duits, A.J. et al. (1991). "Selective Enhancement of Leu-Cam Expression by Interleukin 6 During Differentiation of Human Promonocytic U937 Cells," *Scand. J. Immunol.* 33(2):151-159.

Fearon, D.T. et al. (1995). "The CD19/CR2/TAPA-1 Complex of B Lymphocytes: Linking Natural to Acquired Immunity," *Annu. Rev. Immunol.*13:127-149.

Fearon, D.T. (Oct. 1998). "The Complement System and Adaptive Immunity," *Semin. Immunol.* 10(5):355-361.

Fingeroth, J.D. et al. (Jul. 1984). "Epstein-Barr Virus Receptor of Human B Lymphocytes is the C3d Receptor CR2," *PNAS* 81(14):4510-4514.

Fingeroth, J.D. et al. (Jan. 1989). "Identification of Murine Complement Receptor Type 2," *PNAS* 86(1):242-246.

Frémeaux-Bacchi, V. et al. (Dec. 1998). "Soluble CD21 Induces Activation and Differentiation of Human Monocytes Through Binding to Membrane CD23," *Eur. J. Immunol.* 28:4268-4274.

Gordon, J. (Sep. 1994). "B-cell Signaling via the C-type Lectins CD23 and CD72," *Immunol. Today* 15(9):411-417.

Guthridge, J.M. et al. (May 22, 2001; e-pub. Apr. 28, 2001). "Structural Studies in Solution of the Recombinant N-Terminal Pair of Short Consensus/Complement Repeat Domains of Complement Receptor Type 2 (CR2/CD21) and Interactions with Its Ligand C3dg," *Biochemistry* 40(20):5931-5941.

Guthridge, J.M. et al. (Nov. 2001). "Epitope Mapping Using the X-Ray Crystallographic Structure of Complement Receptor Type 2 (CR2)/CD21: Identification of a Highly Inhibitory Monoclonal Antibody That Directly Recognizes the CR2-C3d Interface," *J. Immunol.* 167(10):5758-5766.

Harris, C.L. et al. (Nov. 2002). "Tailoring Anti-Complement Therapeutics," *Biochem. Soc. Trans.* 30(6):1019-1026.

Hebell, T. et al. (Oct. 4, 1991). "Suppression of the Immune Response by a Soluble Complement Receptor of B Lymphocytes," *Science* 254:102-105.

Heyman, B. (2000). "Regulation of Antibody Responses via Antibodies, Complement, and Fc Receptors," *Ann. Rev. Immunol.* 18:709-738.

Higgins, P.J. et al. (Mar. 15, 1997). "A Soluble Chimeric Complement Inhibitory Protein That Possesses Both Decay-Accelerating and Factor I Cofactor Activities," *J. Immunol.* 158(6):2872-2881.

Holers, V.M. (1989). "Complement Receptors" *In The Year In Immunology 1988. Cellular, Molecular and Clinical Aspects*, Cruse, J.M. et al. eds., Basel, Karger, 4:231-240.

Hsu, S.I-H. et al. (2003). "Chronic Progression of Tubulointerstitial Damage in Proteinuric Renal Disease Is Mediated by Complement Activation: A Therapeutic Role for Complement Inhibitors?" *J. Am. Soc. Nephrol.* 14:S186-S191.

Hughes, B.J. et al. (Nov. 15, 1989). "Monoclonal Antibody Targeting of Liposomes to Mouse Lung in Vivo," *Cancer Res.* 49(22):6214-6220.

International Search Report mailed Sep. 15, 2004, for PCT Application No. PCT/US03/36459 filed Nov. 13, 2003, two pages.

Kalli, K.R. et al. (Jul. 15, 1991). "Interaction of iC3b With Recombinant Isotypic and Chimeric Forms of CR2," *J. Immunol.* 147(2):590-594.

Kaplan, M. (2002). "Eculizumab Alexion," *Curr. Opin. Investig. Drugs* 3(7):1017-1023.

Khurana, S. et al. (Jun. 9, 1998). "Crystal Structure of 2,5-diketo-D-gluconic Acid Reductase A Complexed with NADPH at 2.1-Å Resolution," *PNAS.* 95(12):6768-6773.

Kroshus, T.J. et al. (Jun. 15, 2000). "A Recombinant Soluble Chimeric Complement Inhibitor Composed of Human CD46 and CD55 Reduces Acute Cardiac Tissue Injury in Models of Pig-to-Human Heart Transplantation," *Transplantation* 69(11):2282-2289.

Lambris, J.D. et al. (Jun. 1985). "Mapping of the C3d Receptor (CR2)-Binding Site and a Neoantigenic Site in the C3d Domain of the Third Component of Complement," *PNAS* 82(12):4235-4239.

Law, S.K. et al. (Mar. 1979). "Action of the C3b-Inactivator on the Cell-Bound C3b," *J. Immunol.* 122(3):759-765.

Law, S.K.A. et al. (1995). "Complement" *In In Focus*, Second Edition, Male, D. ed., IRL Press at Oxford University Press, Inc.: New York, NY, pp. vii-ix. (Table of Contents Only.).

Linton, S.M. et al. (Nov. 2000). "Therapeutic Efficacy of a Novel Membrane-Targeted Complement Regulator in Antigen-Induced Arthritis in the Rat," *Arthritis Rheum.* 43(11):2590-2597.

Lowell, C.A. et al. (Dec. 1, 1989). "Mapping of the Epstein-Barr Virus and C3dg Binding Sites to a Common Domain on Complement Receptor Type 2," *J. Exp. Med.* 170(6):1931-1946.

Martin, D.R. et al. (Dec. 1991). "Determination of the Structural Basis for Selective Binding of Epstein-Barr Virus to Human Complement Receptor Type 2," *J. Exp. Med.* 174:1299-1311.

Martin, D.R. et al. (Aug. 1994). "Determination of the Role for CD21 During Epstein-Barr Virus Infection of B-Lymphoblastoid Cells," *J. Virol.* 68(8):4716-4726.

Matsumoto, A.K. et al. (Jan. 1, 1991). "Intersection of the Complement and Immune Systems: A Signal Transduction Complex of the B Lymphocyte-Containing Complement Receptor Type 2 and CD19," *J. Exp. Med.* 173(1):55-64.

Mendrick, D.L. et al. (1983). "Monoclonal Antibodies Against Rat Glomerular Antigens: Production and Specificity," *Lab. Invest.* 49(1):107-117.

Mendrick, D.L. et al. (1988). "I. Induction of Proteinuria in the Rat by a Monoclonal Antibody Against SGP-115/107," *Kidney Int.* 33:818-830.

Meri, S. et al. (Jun. 15, 1996). "Structural Composition and Functional Characterization of Soluble CD59: Heterogeneity of the Oligosaccharide and Glycophosphoinositol (GPI) Anchor Revealed by Laser-Desorption Mass Spectrometric Analysis," *Biochem. J.* 316(3):923-935.

Moir, S. et al. (Sep. 4, 2000). "B Cells of HIV-1-infected Patients Bind Virions Through CD21-Complement Interactions and Transmit Infectious Virus to Activated T Cells," *J. Exp. Med.* 192(5):637-645.

Molina, H. et al. (Jul. 5, 1991). "Analysis of Epstein-Barr Virus-binding Sites on Complement Receptor 2 (CR2/CD21) Using Human-Mouse Chimeras and Peptides," *J. Biol. Chem.* 266(19):12173-12179.

Molina, H. et al. (Jul. 15, 1994). "Analysis of C3b/C3d Binding Sites and Factor I Cofactor Regions Within Mouse Complement Receptors 1 and 2," *J. Immunol.* 153(2):789-795.

Molina, H. et al. (May 15, 1995). "Characterization of a Complement Receptor 2 (CR2, CD21) Ligand Binding Site for C3. An Initial Model of Ligand Interaction with Two Linked Short Consensus Repeat Modules," *J. Immunol.* 154(10):5426-5435.

Molina, H. et al. (Apr. 1996). "Markedly Impaired Humoral Immune Response in Mice Deficient in Complement Receptors 1 and 2," *PNAS* 93:3357-3361.

Mulligan, M.S. et al. (Apr. 15, 1999). "Endothelial Targeting and Enhanced Antiinflammatory Effects of Complement Inhibitors Possessing Sialyl Lewis$^x$ Moieties," *J. Immunol.* 162(8):4952-4959.

Nagar, B. et al. (May 22, 1998). "X-Ray Crystal Structure of C3d: A C3 Fragment and Ligand for Complement Receptor 2," *Science* 280:1277-1281.

Okano, M. (Jan. 1998). "Epstein-Barr Virus Infection and its Role in the Expanding Spectrum of Human Diseases," *Acta Paediatr.* 87(1):11-18.

Poznansky, M.C. et al. (Aug. 15, 1989). "The Difference Between Human C3F and C3S Results From a Single Amino Acid Change From an Asparagine to an Aspartate Residue at Position 1216 on the α-Chain of the Complement Component, C3," *J. Immunol.* 143(4):1254-1258.

Prodeus, A.P. et al. (Nov. 1998). "A Critical Role for Complement in Maintenance of Self-Tolerance," *Immunity* 9(5):721-731.

Prodinger, W.M. et al. (Nov. 1, 1998). "Characterization of C3dg Binding to a Recess Formed Between Short Consensus Repeats 1 and 2 of Complement Receptor Type 2 (CR2; CD21)," *J. Immunol.* 161(9):4604-4610.

Quigg, R.J. et al. (Jan. 2000). "Production and Functional Analysis of Rat CD59 and Chimeric CD59-Crry as Active Soluble Proteins in *Pichia pastoris*," *Immunology* 99(1):46-53.

Ramm, L.E. et al. (Aug. 1982). "Transmembrane Channel Formation by Complement: Functional Analysis of the Number of C5b6, C7, C8, and C9 Molecules Required for a Single Channel," *PNAS* 79(15):4751-4755.

Rao, P.E. et al. (Jul. 1985). "OKB7, A Monoclonal Antibody That Reacts at or Near the C3d Binding Site of Human CR2," *Cell. Immunol.* 93(2):549-555.

Rioux, P. (2001). "TP-10 AVANT Immunotherapeutics," *Curr. Opin. Investig. Drugs* 2(3):364-371.

Rittershaus, C.W. et al. (Apr. 16, 1999). "Recombinant Glycoproteins That Inhibit Complement Activation and Also Bind the Selectin Adhesion Molecules," *J. Biol. Chem.* 274(16):11267-11244.

Ross, G.D. et al. (Feb. 1992). "Macrophage Cytoskeleton Association with CR3 and CR4 Regulates Receptor Mobility and Phagocytosis of iC3b-opsonized Erythrocytes," *J. Leukoc. Biol.* 51(2):109-117.

Rothlein, R. et al. (May 1, 1986). "The Requirement for Lymphocyte Function-Associated Antigen 1 in Homotypic Leukocyte Adhesion Stimulated by Phorbol Ester," *J. Exp. Med.* 163(5):1132-1149.

Rushmere, N.K. et al. (Feb. 2000). "Production and Functional Characterization of a Soluble Recombinant Form of Mouse CD59," *Immunology* 99(2):326-332.

Salerno, C.T. et al. (Mar. 2002). "A Soluble Chimeric Inhibitor of C3 and C5 Convertases, Complement Activation Blocker-2, Prolongs Graft Survival in Pig-to-Rhesus Monkey Heart Transplantation," *Xenotransplantation* 9(2):125-134.

Seya, T. et al. (1985). "Limited Proteolysis of Complement Protein C3b by Regulatory Enzyme C3b Inactivator: Isolation and Characterization of a Biologically Active Fragment, C3d,g," *J. Biochem.* 97(1):373-382.

Sheerin, N.S. et al. (Oct. 2002). "Leaked Protein and Interstitial Damage in the Kidney: Is Complement the Missing Link?" *Clin. Exp. Immunol.* 130(1):1-3.

Smith, G.P. et al. (2001). "Membrane-Targeted Complement Inhibitors," *Mol. Immunol.* 38:249-255.

Song, H. et al. (Jun. 2003). "Complement Receptor 2-Mediated Targeting of Complement Inhibitors to Sites of Complement Activation," *J. Clin. Invest.* 111(12):1875-1885.

Sugita, Y. et al. (May 1994). "Recombinant Soluble CD59 Inhibits Reactive Haemolysis with Complement," *Immunology* 82(1):34-41.

Supplementary European Search Report mailed Jul. 3, 2006, for EP Application No. 03796403.8 filed Nov. 13, 2003, three pages.

Supplementary Partial European Search Report mailed Apr. 3, 2006, for EP Application No. 03796403.8 filed Nov. 13, 2003, two pages.

Szakonyi, G. et al. (Jun. 1, 2001). "Structure of Complement Receptor 2 in Complex with Its C3d Ligand," *Science* 292(5522):1725-1728.

Takeda, J. et al. (1986). "Number of Hits Necessary for Complement-Mediated Hemolysis," *Microbiol. Immunol.* 30(5):461-468.

Ten, R.M. et al. (Oct. 1, 1999). "The Signal Transduction Pathway of CD23 (FcεRIIb) Targets IκB Kinase," *J. Immunol.* 163(7):3851-3857.

Ward, T. et al. (Nov. 1, 1994). "Decay-Accelerating Factor CD55 is Identified as the Receptor for Echovirus 7 Using CELICS, a Rapid Immuno-Focal Cloning Method," *EMBO J.* 13(21):5070-5074.

Whiss, P.A. (2002). "Pexelizumab Alexion," *Curr. Opin. Investig. Drugs* 3(6):870-877.

Wiles, A.P. et al. (1997). "NMR Studies of a Viral Protein that Mimics the Regulators of Complement Activation," *J. Mol. Biol.* 272(2):253-265.

Yu, J. et al. (Jan. 1999). "Protection of Human Breast Cancer Cells from Complement-mediated Lysis by Expression of Heterologous CD59," *Clin. Exp. Immunol.* 115(1):13-18.

Zhang, H-F. et al. (Jan. 1999). "Targeting of Functional Antibody-CD59 Fusion Proteins to a Cell Surface," *J. Clin. Invest.* 103(1):55-61.

Zhang, H-F. et al. (Jul. 20, 2001). "Targeting of Functional Antibody-Decay-Accelerating Factor Fusion Proteins to a Cell Surface," *J. Biol. Chem.* 276(29):27290-27295.

Atkinson, C. et al. (Sep. 2007). "Targeted Inhibition of the Alternative Complement Pathway Delays the Onset of Antibody-Mediated Rejection in a Mouse Heterotopic Heart Transplant Model," *Molecular Immunology* 44(16):3944, Abstract No. P24.

Huang, Y. et al. (Sep. 2007). "A Novel Targeted Inhibitor of the Alternative Pathway of Complement," *Molecular Immunology* 44(16):3947, Abstract No. P31.

International Search Report mailed on Mar. 6, 2008, for PCT Application No. PCT/US2007/014602, five pages.

Krushkal J. et al. (2000). "Evolutionary Relationships Among Proteins Encoded by the Regulator of Complement Activation Gene Cluster," *Molecular Biology and Evolution* 17(11):1718-1730.

Liszewski, M.K. et al. (1997). "Complement Inhibitors as Therapeutic Agents," *Clinical Immunology Newsletter* 17(12):168-173.

Ferreira, V.P. et al. (Sep. 15, 2007, e-pub. Jun. 6, 2007). "Factor H-Mediated Cell Surface Protection from Complement is Critical for the Survival of PNH Erythrocytes," *Blood* 110(6):2190-2192.

\* cited by examiner

CR2-FH expression plasmid

CR2-FH protein with signal peptide

Mature CR2-FH Protein

Figure 2.

Amino acid sequence of human CR2 (SEQ ID NO:1)

MGAAGLLGVFLALVAPGVLGISCGSPPPILNGRISYYSTPIAVGTVIRYSCSGTFRLIGEKSLLCITKD
KVDGTWDKPAPKCEYFNKYSSCPEPIVPGGYKIRGSTPYRHGDSVTFACKTNFSMNGNKSVWCQ
ANNMWGPTRLPTCVSVFPLECPALPMIHNGHHTSENVGSIAPGLSVTYSCESGYLLVGEKIINCLSS
GKWSAVPPTCEEARCKSLGRFPNGKVKEPPILRVGVTANFFCDEGYRLQGPPSSRCVIAGQGVAW
TKMPVCEEIFCPSPPPILNGRHIGNSLANVSYGSIVTYTCDPDPEEGVNFILIGESTLRCTVDSQKTGT
WSGPAPRCELSTSAVQCPHPQILRGRMVSGQKDRYTYNDTVIFACMFGFTLKGSKQIRCNAQGTW
EPSAPVCEKECQAPPNILNGQKEDRHMVRFDPGTSIKYSCNPGYVLVGEESIQCTSEGVWTPPVPQ
CKVAACEATGRQLLTKPQHQFVRPDVNSSCGEGYKLSGSVYQECQGTIPWFMEIRLCKEITCPPPP
VIYNGAHTGSSLEDFPYGTTVTYTCNPGPERGVEFSLIGESTIRCTSNDQERGTWSGPAPLCKLSLL
AVQCSHVHIANGYKISGKEAPYFYNDTVTFKCYSGFTLKGSSQIRCKRDNTWDPEIPVCEKGCQPP
PGLHHGRHTGGNTVFFVSGMTVDYTCDPGYLLVGNKSIHCMPSGNWSPSAPRCEETCQHVRQSL
QELPAGSRVELVNTSCQDGYQLTGHAYQMCQDAENGIWFKKIPLCKVIHCHPPPVIVNGKHTGM
MAENFLYGNEVSYECDQGFYLLGEKNCSAEVILKAWILERAFPQCLRSLCPNPEVKHGYKLNKTH
SAYSHNDIVYVDCNPGFIMNGSRVIRCHTDNTWVPGVPTCIKKAFIGCPPPPKTPNGNHTGGNIARF
SPGMSILYSCDQGYLVVGEPLLLCTHEGTWSQPAPHCKEVNCSSPADMDGIQKGLEPRKMYQYG
AVVTLECEDGYMLEGSPQSQCQSDHQWNPPLAVCRSRSLAPVLCGIAAGLILLTFLIVITLYVISKH
RERNYYTDTSQKEAFHLEAREVYSVDPYNPAS

Amino acid sequence of human FH (SEQ ID NO:2)

MRLLAKIICLMLWAICVAEDCNELPPRRNTEILTGSWSDQTYPEGTQAIYKCRPGYRSLGNVIMVC
RKGEWVALNPLRKCQKRPCGHPGDTPFGTFTLTGGNVFEYGVKAVYTCNEGYQLLGEINYRECD
TDGWTNDIPICEVVKCLPVTAPENGKIVSSAMEPDREYHFGQAVRFVCNSGYKIEGDEEMHCSDD
GFWSKEKPKCVEISCKSPDVINGSPISQKIIYKENERFQYKCNMGYEYSERGDAVCTESGWRPLPSC
EEKSCDNPYIPNGDYSPLRIKHRTGDEITYQCRNGFYPATRGNTAKCTSTGWIPAPRCTLKPCDYPD
IKHGGLYHENMRRPYFPVAVGKYYSYYCDEHFETPSGSYWDHIHCTQDGWSPAVPCLRKCYFPY
LENGYNQNHGRKFVQGKSIDVACHPGYALPKAQTTVTCMENGWSPTPRCIRVKTCSKSSIDIENGF
ISESQYTYALKEKAKYQCKLGYVTADGETSGSIRCGKDGWSAQPTCIKSCDIPVFMNARTKNDFT
WFKLNDTLDYECHDGYESNTGSTTGSIVCGYNGWSDLPICYERECELPKIDVHLVPDRKKDQYKV
GEVLKFSCKPGFTIVGPNSVQCYHFGLSPDLPICKEQVQSCGPPPELLNGNVKEKTKEEYGHSEVV
EYYCNPRFLMKGPNKIQCVDGEWTTLPVCIVEESTCGDIPELEHGWAQLSSPPYYYGDSVEFNCSE
SFTMIGHRSITCIHGVWTQLPQCVAIDKLKKCKSSNLIILEEHLKNKKEFDHNSNIRYRCRGKEGWI
HTVCINGRWDPEVNCSMAQIQLCPPPPQIPNSHNMTTTLNYRDGEKVSVLCQENYLIQEGEEITCK
DGRWQSIPLCVEKIPCSQPPQIEHGTINSSRSSQESYAHGTKLSYTCEGGFRISEENETTCYMGKWSS
PPQCEGLPCKSPPEISHGVVAHMSDSYQYGEEVTYKCFEGFGIDGPAIAKCLGEKWSHPPSCIKTDC
LSLPSFENAIPMGEKKDVYKAGEQVTYTCATYYKMDGASNVTCINSRWTGRPTCRDTSCVNPPTV
QNAYIVSRQMSKYPSGERVRYQCRSPYEMFGDEEVMCLNGNWTEPPQCKDSTGKCGPPPPIDNG
DITSFPLSVYAPASSVEYQCQNLYQLEGNKRITCRNGQWSEPPKCLHPCVISREIMENYNIALRWTA
KQKLYSRTGESVEFVCKRGYRLSSRSHTLRTTCWDGKLEYPTCAKR

Figure 3.

Amino acid sequence of human CR2-FH (SEQ ID NO:3)

ISCGSPPPILNGRISYYSTPIAVGTVIRYSCSGTFRLIGEKSLLCITKDKVDGTWDKPAPKCEYFNKYS
SCPEPIVPGGYKIRGSTPYRHGDSVTFACKTNFSMNGNKSVWCQANNINNMWGPTRLPTCVSVFP
LECPALPMIHNGHHTSENVGSIAPGLSVTYSCESGYLLVGEKIINCLSSGKWSAVPPTCEEAXCKSL
GRFPNGKVKEPPILRVGVTANFFCDEGYRLQGPPSSRCVIAGQGVAWTKMPVCGGGGSGGGGSC
VAEDCNELPPRRNTEILTGSWSDQTYPEGTQAIYKCRPGYRSLGNVIMVCRKGEWVALNPLRKCQ
KRPCGHPGDTPFGTFTLTGGNVFEYGVKAVYTCNEGYQLLGEINYRECDTDGWTNDIPICEVVKC
LPVTAPENGKIVSSAMEPDREYHFGQAVRFVCNSGYKIEGDEEMHCSDDGFWSKEKPKCVEISCK
SPDVINGSPISQKIIYKENERFQYKCNMGYEYSERGDAVCTESGWRPLPSCEEKSCDNPYIPNGDYS
PLRIKHRTGDEITYQCRNGFYPATRGNTAKCTSTGWIPAPRCT

Nucleic acid sequence of human CR2-FH (SEQ ID NO:4)

ATTTCTTGTGGCTCTCCTCCGCCTATCCTAAATGGCCGGATTAGTTATTATTCTACCCCCATTGC
TGTTGGTACCGTGATAAGGTACAGTTGTTCAGGTACCTTCCGCCTCATTGGAGAAAAAGTCT
ATTATGCATAACTAAAGACAAAGTGGATGGAACCTGGGATAAACCTGCTCCTAAATGTGAAT
ATTTCAATAAATATTCTTCTTGCCCTGAGCCCATAGTACCAGGAGGATACAAAATTAGAGGCT
CTACACCCTACAGACATGGTGATTCTGTGACATTTGCCTGTAAAACCAACTTCTCCATGAACG
GAAACAAGTCTGTTTGGTGTCAAGCAAATAATATAAATAATATGTGGGGGCCGACACGACTA
CCAACCTGTGTAAGTGTTTTCCCTCTCGAGTGTCCAGCACTTCCTATGATCCACAATGGACATC
ACACAAGTGAGAATGTTGGCTCCATTGCTCCAGGATTGTCTGTGACTTACAGCTGTGAATCTG
GTTACTTGCTTGTTGGAGAAAAGATCATTAACTGTTTGTCTTCGGGAAAATGGAGTGCTGTCC
CCCCCACATGTGAAGAGGCACSCTGTAAATCTCTAGGACGATTTCCCAATGGGAAGGTAAAGG
AGCCTCCAATTCTCCGGGTTGGTGTAACTGCAAACTTTTTCTGTGATGAAGGGTATCGACTGC
AAGGCCCACCTTCTAGTCGGTGTGTAATTGCTGGACAGGGAGTTGCTTGGACCAAAATGCCAG
TATGTGGCGGAGGTGGGTCGGGTGGCGGCGGATCTTGTGTAGCAGAAGATTGCAATGAACTT
CCTCCAAGAAGAAATACAGAAATTCTGACAGGTTCCTGGTCTGACCAAACATATCCAGAAGG
CACCCAGGCTATCTATAAATGCCGCCCTGGATATAGATCTCTTGGAAATGTAATAATGGTATG
CAGGAAGGGAGAATGGGTTGCTCTTAATCCATTAAGGAAATGTCAGAAAAGGCCCTGTGGAC
ATCCTGGAGATACTCCTTTTGGTACTTTTACCCTTACAGGAGGAAATGTGTTTGAATATGGTGT
AAAAGCTGTGTATACATGTAATGAGGGGTATCAATTGCTAGGTGAGATTAATTACCGTGAATG
TGACACAGATGGATGGACCAATGATATTCCTATATGTGAAGTTGTGAAGTGTTTACCAGTGAC
AGCACCAGAGAATGGAAAAATTGTCAGTAGTGCAATGGAACCAGATCGGGAATACCATTTTG
GACAAGCAGTACGGTTTGTATGTAACTCAGGCTACAAGATTGAAGGAGATGAAGAAATGCAT
TGTTCAGACGATGGTTTTTGGAGTAAAGAGAAACCAAAGTGTGTGGAAATTTCATGCAAATCC
CCAGATGTTATAAATGGATCTCCTATATCTCAGAAGATTATTTATAAGGAGAATGAACGATTT
CAATATAAATGTAACATGGGTTATGAATACAGTGAAAGAGGAGATGCTGTATGCACTGAATC
TGGATGGCGTCCGTTGCCTTCATGTGAAGAAAAATCATGTGATAATCCTTATATTCCAAATGG
TGACTACTCACCTTTAAGGATTAAACACAGAACTGGAGATGAAATCACGTACCAGTGTAGAA
ATGGTTTTTATCCTGCAACCCGGGGAAATACAGCCAAATGCACAAGTACTGGCTGGATACCTG
CTCCGAGATGTACCT

Figure 4.

SEQ ID NO:5, nnn = optional linker

ISCGSPPPILNGRISYYSTPIAVGTVIRYSCSGTFRLIGEKSLLCITKDKVDGTWDKPAPKCEYFNKYS
SCPEPIVPGGYKIRGSTPYRHGDSVTFACKTNFSMNGNKSVWCQANNMWGPTRLPTCVSVFPLEC
PALPMIHNGHHTSENVGSIAPGLSVTYSCESGYLLVGEKIINCLSSGKWSAVPPTCEEARCKSLGRF
PNGKVKEPPILRVGVTANFFCDEGYRLQGPPSSRCVIAGQGVAWTKMPVCnnnCVAEDCNELPPRR
NTEILTGSWSDQTYPEGTQAIYKCRPGYRSLGNVIMVCRKGEWVALNPLRKCQKRPCGHPGDTPF
GTFTLTGGNVFEYGVKAVYTCNEGYQLLGEINYRECDTDGWTNDIPICEVVKCLPVTAPENGKIVS
SAMEPDREYHFGQAVRFVCNSGYKIEGDEEMHCSDDGFWSKEKPKCVEISCKSPDVINGSPISQKII
YKENERFQYKCNMGYEYSERGDAVCTESGWRPLPSCEEKSCDNPYIPNGDYSPLRIKHRTGDEITY
QCRNGFYPATRGNTAKCTSTGWIPAPRCT SEQ ID NO:6, nnn = optional linker ISCGSPPPILNGRISYYSTPIAVGTVIRYSCSGTFRLIGEKSLLCITKDKVDGTWDKPAPKCEYFNKYS
SCPEPIVPGGYKIRGSTPYRHGDSVTFACKTNFSMNGNKSVWCQANNMWGPTRLPTCVSVFPLEC
PALPMIHNGHHTSENVGSIAPGLSVTYSCESGYLLVGEKIINCLSSGKWSAVPPTCEEARCKSLGRF
PNGKVKEPPILRVGVTANFFCDEGYRLQGPPSSRCVIAGQGVAWTKMPVCnnnCVAEDCNELPPRR
NTEILTGSWSDQTYPEGTQAIYKCRPGYRSLGNIIMVCRKGEWVALNPLRKCQKRPCGHPGDTPF
GTFTLTGGNVFEYGVKAVYTCNEGYQLLGEINYRECDTDGWTNDIPICEVVKCLPVTAPENGKIVS
SAMEPDREYHFGQAVRFVCNSGYKIEGDEEMHCSDDGFWSKEKPKCVEISCKSPDVINGSPISQKII
YKENERFQYKCNMGYEYSERGDAVCTESGWRPLPSCEEKSCDNPYIPNGDYSPLRIKHRTGDEITY
QCRNGFYPATRGNTAKCTSTGWIPAPRCT

Figure 5.

SEQ ID NO:7, nnn = optional linker

ISCGSPPPILNGRISYYSTPIAVGTVIRYSCSGTFRLIGEKSLLCITKDKVDGTWDKPAPKCEYFNKYS
SCPEPIVPGGYKIRGSTPYRHGDSVTFACKTNFSMNGNKSVWCQANNINNMWGPTRLPTCVSVFP
LECPALPMIHNGHHTSENVGSIAPGLSVTYSCESGYLLVGEKIINCLSSGKWSAVPPTCEEAXCKSL
GRFPNGKVKEPPILRVGVTANFFCDEGYRLQGPPSSRCVIAGQGVAWTKMPVCnnnEDCNELPPRR
NTEILTGSWSDQTYPEGTQAIYKCRPGYRSLGNVIMVCRKGEWVALNPLRKCQKRPCGHPGDTPF
GTFTLTGGNVFEYGVKAVYTCNEGYQLLGEINYRECDTDGWTNDIPICEVVKCLPVTAPENGKIVS
SAMEPDREYHFGQAVRFVCNSGYKIEGDEEMHCSDDGFWSKEKPKCVEISCKSPDVINGSPISQKII
YKENERFQYKCNMGYEYSERGDAVCTESGWRPLPSCEEKSCDNPYIPNGDYSPLRIKHRTGDEITY
QCRNGFYPATRGNTAKCTSTGWIPAPRCT SEQ ID NO:8, nnn = optional linker ISCGSPPPILNGRISYYSTPIAVGTVIRYSCSGTFRLIGEKSLLCITKDKVDGTWDKPAPKCEYFNKYS
SCPEPIVPGGYKIRGSTPYRHGDSVTFACKTNFSMNGNKSVWCQANNINNMWGPTRLPTCVSVFP
LECPALPMIHNGHHTSENVGSIAPGLSVTYSCESGYLLVGEKIINCLSSGKWSAVPPTCEEAXCKSL
GRFPNGKVKEPPILRVGVTANFFCDEGYRLQGPPSSRCVIAGQGVAWTKMPVCnnnEDCNELPPRR
NTEILTGSWSDQTYPEGTQAIYKCRPGYRSLGNIIMVCRKGEWVALNPLRKCQKRPCGHPGDTPF
GTFTLTGGNVFEYGVKAVYTCNEGYQLLGEINYRECDTDGWTNDIPICEVVKCLPVTAPENGKIVS
SAMEPDREYHFGQAVRFVCNSGYKIEGDEEMHCSDDGFWSKEKPKCVEISCKSPDVINGSPISQKII
YKENERFQYKCNMGYEYSERGDAVCTESGWRPLPSCEEKSCDNPYIPNGDYSPLRIKHRTGDEITY
QCRNGFYPATRGNTAKCTSTGWIPAPRCT

Figure 6.

SEQ ID NO:9, nnn = optional linker

ISCGSPPPILNGRISYYSTPIAVGTVIRYSCSGTFRLIGEKSLLCITKDKVDGTWDKPAPKCEYFNKYS
SCPEPIVPGGYKIRGSTPYRHGDSVTFACKTNFSMNGNKSVWCQANNMWGPTRLPTCVSVFPLEC
PALPMIHNGHHTSENVGSIAPGLSVTYSCESGYLLVGEKIINCLSSGKWSAVPPTCEEARCKSLGRF
PNGKVKEPPILRVGVTANFFCDEGYRLQGPPSSRCVIAGQGVAWTKMPVCnnnEDCNELPPRRNTE
ILTGSWSDQTYPEGTQAIYKCRPGYRSLGNVIMVCRKGEWVALNPLRKCQKRPCGHPGDTPFGTF
TLTGGNVFEYGVKAVYTCNEGYQLLGEINYRECDTDGWTNDIPICEVVKCLPVTAPENGKIVSSA
MEPDREYHFGQAVRFVCNSGYKIEGDEEMHCSDDGFWSKEKPKCVEISCKSPDVINGSPISQKIIYK
ENERFQYKCNMGYEYSERGDAVCTESGWRPLPSCEEKSCDNPYIPNGDYSPLRIKHRTGDEITYQC
RNGFYPATRGNTAKCTSTGWIPAPRCT SEQ ID NO:10, nnn = optional linker ISCGSPPPILNGRISYYSTPIAVGTVIRYSCSGTFRLIGEKSLLCITKDKVDGTWDKPAPKCEYFNKYS
SCPEPIVPGGYKIRGSTPYRHGDSVTFACKTNFSMNGNKSVWCQANNMWGPTRLPTCVSVFPLEC
PALPMIHNGHHTSENVGSIAPGLSVTYSCESGYLLVGEKIINCLSSGKWSAVPPTCEEARCKSLGRF
PNGKVKEPPILRVGVTANFFCDEGYRLQGPPSSRCVIAGQGVAWTKMPVCnnnEDCNELPPRRNTE
ILTGSWSDQTYPEGTQAIYKCRPGYRSLGNIIMVCRKGEWVALNPLRKCQKRPCGHPGDTPFGTFT
LTGGNVFEYGVKAVYTCNEGYQLLGEINYRECDTDGWTNDIPICEVVKCLPVTAPENGKIVSSAM
EPDREYHFGQAVRFVCNSGYKIEGDEEMHCSDDGFWSKEKPKCVEISCKSPDVINGSPISQKIIYKE
NERFQYKCNMGYEYSERGDAVCTESGWRPLPSCEEKSCDNPYIPNGDYSPLRIKHRTGDEITYQCR
NGFYPATRGNTAKCTSTGWIPAPRCT

Figure 7.

CD5 peptide sequence (SEQ ID NO:11)

MPMGSLQPLATLYLLGMLVAS

CD5 nucleotide sequence (SEQ ID NO:12)

ATGCCCATGGGGTCTCTGCAACCGCTGGCCACCTTGTACCTGCTGGGGATGCTGGTCGCTTCCT
GCCTCGGA

CR2 peptide sequence (SEQ ID NO:13)

MGAAGLLGVFLALVAPG

CR2 nucleotide sequence (SEQ ID NO:14)

ATGGGCGCCGCGGGCCTGCTCGGGGTTTTCTTGGCTCTCGTCGCACCGGGGGTCCTCGGG

CR2 peptide sequence (SEQ ID NO:25)

MGAAGLLGVFLALVAPGVLG

CR2 nucleotide sequence (SEQ ID NO:26)

ATGGGAGCCGCTGGTCTGCTCGGCGTGTTCCTCGCCTTGGTGGCACCTGGCGTCCTGGGC

Figure 8.

Mouse CR2 amino acid sequence (SEQ ID NO:15)

MLTWFLFYFSEISCDPPPEVKNARKPYYSLPIVPGTVLRYTCSPSYRLIGEKAIFCISENQVHATWDK
APPICESVNKTISCSDPIVPGGFMNKGSKAPFRHGDSVTFTCKANFTMKGSKTVWCQANEMWGPT
ALPVCESDFPLECPSLPTIHNGHHTGQHVDQFVAGLSVTYSCEPGYLLTGKKTIKCLSSGDWDGVI
PTCKEAQCEHPGKFPNGQVKEPLSLQVGTTVYFSCNEGYQLQGGQPSSQCVIVEQKAIWTKKPVCK
EILCPPPPPVRNGSHTGSFSENVPYGSTVTYTCDPSPEKGVSFTLIGEKTINCTTGSQKTGIWSGPAP
YCVLSTSAVLCLQPKIKRGQILSILKDSYSYNDTVAFSCEPGFTLKGNRSIRCNAHGTWEPPVPVCE
KGCQAPPKIINGQKEDSYLLNFDPGTSIRYSCDPGYLLVGEDTIHCTPEGKWTPITPQCTVAECKPV
GPHLFKRPQNQFIRTAVNSSCDEGFQLSESAYQLCQGTIPWFIEIRLCKEITCPPPPVIHNGTHTWSSS
EDVPYGTVVTYMCYPGPEEGVKFKLIGEQTIHCTSDSRGRGSWSSPAPLCKLSLPAVQCTDVHVE
NGVKLTDNKAPYFYNDSVMFKCDDGYILSGSSQIRCKANNTWDPEKPLCKKEGCEPMRVHGLPD
DSHIKLVKRTCQNGYQLTGYTYEKCQNAENGTWFKKIEVCTVILCQPPPKIANGGHTGMMAKHF
LYGNEVSYECDEGFYLLGEKSLQCVNDSKGHGSWSGPPPQCLQSSPLTHCPDPEVKHGYKLNKTH
SAFSHNDIVHFVCNQGFIMNGSHLIRCHTNNTWLPGVPTCIRKASLGCQSPSTIPNGNHTGGSIARF
PPGMSVMYSCYQGFLMAGEARLICTHEGTWSQPPPFCKEVNCSFPEDTNGIQKGFQPGKTYRFGA
TVTLECEDGYTLEGSPQSQCQDDSQWNPPLALCKYRRWSTIPLICGISVGSALIILMSVGFCMILKH
RESNYYTKTRPKEGALHLETREVYSIDPYNPAS

Mouse FH amino acid sequence (SEQ ID NO:16)

MRLSARIIWLILWTVCAAEDCKGPPPRENSEILSGSWSEQLYPEGTQATYKCRPGYRTLGTIVKVC
KNGKWVASNPSRICRKKPCGHPGDTPFGSFRLAVGSQFEFGAKVVYTCDDGYQLLGEIDYRECGA
DGWINDIPLCEVVKCLPVTELENGRIVSGAAETDQEYYFGQVVRFECNSGFKIEGHKEIHCSENGL
WSNEKPRCVEILCTPPRVENGDGINVKPVYKENERYHYKCKHGYVPKERGDAVCTGSGWSSQPF
CEEKRCSPPYILNGIYTPHRIIHRSDDEIRYECNYGFYPVTGSTVSKCTPTGWIPVPRCTLKPCEFPQF
KYGRLYYEESLRPNFPVSIGNKYSYKCDNGFSPPSGYSWDYLRCTAQGWEPEVPCVRKCVFHYVE
NGDSAYWEKVYVQGQSLKVQCYNGYSLQNGQDTMTCTENGWSPPPKCIRIKTCSASDIHIDNGFL
SESSSIYALNRETSYRCKQGYVTNTGEISGSITCLQNGWSPQPSCIKSCDMPVFENSITKNTRTWFKL
NDKLDYECLVGFENEYKHTKGSITCTYYGWSDTPSCYERECSVPTLDRKLVVSPRKEKYRVGDLL
EFSCSHSGHRVGPDSVQCYHFGWSPGFPTCKGQVASCAPPLEILNGEINGAKKVEYSHGEVVKYDC
KPRFLLKGPNKIQCVDGNWTTLPVCIEEERTCGDIPELEHGSAKCSVPPYHHGDSVEFICEENFTMI
GHGSVSCISGKWTQLPKCVATDQLEKCRVLKSTGIEAIKPKLTEFTHNSTMDYKCRDKQEYERSIC
INGKWDPEPNCTSKTSCPPPPQIPNTQVIETTVKYLDGEKLSVLCQDNYLTQDSEEMVCKDGRWQS
LPRCIEKIPCSQPPTIEHGSINLPRSSEERRDSIESSSHEHGTTFSYVCDDGFRIPEENRITCYMGKWST
PPRCVGLPCGPPPSIPLGTVSLELESYQHGEEVTYHCSTGFGIDGPAFIICEGGKWSDPPKCIKTDCD
VLPTVKNAIIRGKSKKSYRTGEQVTFRCQSPYQMNGSDTVTCVNSRWIGQPVCKDNSCVDPPHVP
NATIVTRTKNKYLHGDRVRYECNKPLELFGQVEVMCENGIWTEKPKCRGL*FDLSLKPSNVFSLD
STGKCGPPPPIDNGDITSLSLPVYEPLSSVEYQCQKYYLLKGKKTITCTNGKWSEPPTCLHACVIPE
NIMESHNIILKWRHTEKIYSHSGEDIEFGCKYGYYKARDSPPFRTKCINGTINYPTCV

Figure 9.

SEQ ID NO:17 (MOUSE CR2-FH)

ISCDPPPEVKNARKPYYSLPIVPGTVLRYTCSPSYRLIGEKAIFCISENQVHATWDKAPPICESVNKTI
SCSDPIVPGGFMNKGSKAPFRHGDSVTFTCKANFTMKGSKTVWCQANEMWGPTALPVCESDFPL
ECPSLPTIHNGHHTGQHVDQFVAGLSVTYSCEPGYLLTGKKTIKCLSSGDWDGVIPTCKEAQCEHP
GKFPNGQVKEPLSLQVGTTVYFSCNEGYQLQGQPSSQCVIVEQKAIWTKKPVCKEILEDCKGPPPR
ENSEILSGSWSEQLYPEGTQATYKCRPGYRTLGTIVKVCKNGKWVASNPSRICRKKPCGHPGDTPF
GSFRLAVGSQFEFGAKVVYTCDDGYQLLGEIDYRECGADGWINDIPLCEVVKCLPVTELENGRIVS
GAAETDQEYYFGQVVRFECNSGFKIEGHKEIHCSENGLWSNEKPRCVEILCTPPRVENGDGINVKP
VYKENERYHYKCKHGYVPKERGDAVCTGSGWSSQPFCEEKRCSPPYILNGIYTPHRIIHRSDDEIR
YECNYGFYPVTGSTVSKCTPTGWIPVPRCT

SEQ ID NO:18 (MOUSE CR2-FH DNA)

ATGCCCATGGGGTCTCTGCAACCGCTGGCCACCTTGTACCTGCTGGGGATGCTGGTCGCTTCC
GTGCTAGCGATTTCTTGTGACCCTCCTCCTGAAGTCAAAAATGCTCGGAAACCCTATTATTCTC
TTCCCATAGTTCCTGGAACTGTTCTGAGGTACACTTGTTCACCTAGCTACCGCCTCATTGGAGA
AAAGGCTATCTTTTGTATAAGTGAAAATCAAGTGCATGCCACCTGGGATAAAGCTCCTCCTAT
ATGTGAATCTGTGAATAAAACCATTTCTTGCTCAGATCCCATAGTACCAGGGGGATTCATGAA
TAAAGGATCTAAGGCACCATTCAGACATGGTGATTCTGTGACATTTACCTGTAAAGCCAACTT
CACCATGAAAGGAAGCAAAACTGTCTGGTGCCAGGCAAATGAAATGTGGGGACCAACAGCTC
TGCCAGTCTGTGAGAGTGATTTCCCTCTGGAGTGCCCATCACTTCCAACGATTCATAATGGAC
ACCACACAGGACAGCATGTTGACCAGTTTGTTGCGGGGTTGTCTGTGACATACAGTTGTGAAC
CTGGCTATTTGCTCACTGGAAAAAAGACAATTAAGTGCTTATCTTCAGGAGACTGGGATGGTG
TCATCCCGACATGCAAAGAGGCCCAGTGTGAACATCCAGGAAAGTTTCCCAATGGGCAGGTA
AAGGAACCTCTGAGCCTTCAGGTTGGCACAACTGTGTACTTCTCCTGTAATGAAGGGTACCAA
TTACAAGGACAACCCTCTAGTCAGTGTGTAATTGTTGAACAGAAAGCCATCTGGACTAAGAAG
CCAGTATGTAAAGAAATTCTCGAAGATTGTAAAGGTCCTCCTCCAAGAGAAAATTCAGAAATT
CTCTCAGGCTCGTGGTCAGAACAACTATATCCAGAAGGCACCCAGGCTACCTACAAATGCCGC
CCTGGATACCGAACACTTGGCACTATTGTAAAAGTATGCAAGAATGGAAAATGGGTGGCGTC
TAACCCATCCAGGATATGTCGGAAAAAGCCTTGTGGGCATCCCGGAGACACACCCTTTGGGTC
CTTTAGGCTGGCAGTTGGATCTCAATTTGAGTTTGGTGCAAAGGTTGTTTATACCTGTGATGAT
GGGTATCAACTATTAGGTGAAATTGATTACCGTGAATGTGGTGCAGATGGCTGGATCAATGAT
ATTCCACTATGTGAAGTTGTGAAGTGTCTACCTGTGACAGAACTCGAGAATGGAAGAATTGTG
AGTGGTGCAGCAGAAACAGACCAGGAATACTATTTTGGACAGGTGGTGCGGTTTGAATGCAA
TTCAGGCTTCAAGATTGAAGGACATAAGGAAATTCATTGCTCAGAAAATGGCCTTTGGAGCAA
TGAAAAGCCACGATGTGTGGAAATTCTCTGCACACCACCGCGAGTGGAAAATGGAGATGGTA
TAAATGTGAAACCAGTTTACAAGGAGAATGAAAGATACCACTATAAGTGTAAGCATGGTTAT
GTGCCCAAAGAAGAGGGGATGCCGTCTGCACAGGCTCTGGATGGAGTTCTCAGCCTTTCTGT
GAAGAAAAGAGATGCTCACCTCCTTATATTCTAAATGGTATCTACACACCTCACAGGATTATA
CACAGAAGTGATGATGAAATCAGATATGAATGTAATTATGGCTTCTATCCTGTAACTGGATCA
ACTGTTTCAAAGTGTACACCCACTGGCTGGATCCCTGTTCCAAGATGTACCT

Figure 10.

```
GAATTCGCCGCCACCATGCCCATGGGGTCTCTGCAACCGCTGGCCACCTTGTACCTGCTGGGG
ATGCTGGTCGCTTCCGTGCTAGCGATTTCTTGTGACCCTCCTCCTGAAGTCAAAAATGCTCGGA
AACCCTATTATTCTCTTCCCATAGTTCCTGGAACTGTTCTGAGGTACACTTGTTCACCTAGCTA
CCGCCTCATTGGAGAAAAGGCTATCTTTTGTATAAGTGAAAATCAAGTGCATGCCACCTGGGA
TAAAGCTCCTCCTATATGTGAATCTGTGAATAAAACCATTTCTTGCTCAGATCCCATAGTACCA
GGGGGATTCATGAATAAAGGATCTAAGGCACCATTCAGACATGGTGATTCTGTGACATTTACC
TGTAAAGCCAACTTCACCATGAAAGGAAGCAAAACTGTCTGGTGCCAGGCAAATGAAATGTG
GGGACCAACAGCTCTGCCAGTCTGTGAGAGTGATTTCCCTCTGGAGTGCCCATCACTTCCAAC
GATTCATAATGGACACCACACAGGACAGCATGTTGACCAGTTTGTTGCGGGGTTGTCTGTGAC
ATACAGTTGTGAACCTGGCTATTTGCTCACTGGAAAAAAGACAATTAAGTGCTTATCTTCAGG
AGACTGGGATGGTGTCATCCCGACATGCAAAGAGGCCCAGTGTGAACATCCAGGAAAGTTTC
CCAATGGGCAGGTAAAGGAACCTCTGAGCCTTCAGGTTGGCACAACTGTGTACTTCTCCTGTA
ATGAAGGGTACCAATTACAAGGACAACCCTCTAGTCAGTGTGTAATTGTTGAACAGAAAGCC
ATCTGGACTAAGAAGCCAGTATGTAAAGAAATTCTCGAAGATTGTAAAGGTCCTCCTCCAAGA
GAAAATTCAGAATTCTCTCAGGCTCGTGGTCAGAACAACTATATCCAGAAGGCACCCAGGCT
ACCTACAAATGCCGCCCTGGATACCGAACACTTGGCACTATTGTAAAAGTATGCAAGAATGG
AAAATGGGTGGCGTCTAACCCATCCAGGATATGTCGGAAAAAGCCTTGTGGGCATCCCGGAG
ACACACCCTTTGGGTCCTTTAGGCTGGCAGTTGGATCTCAATTTGAGTTTGGTGCAAAGGTTGT
TTATACCTGTGATGATGGGTATCAACTATTAGGTGAAATTGATTACCGTGAATGTGGTGCAGA
TGGCTGGATCAATGATATTCCACTATGTGAAGTTGTGAAGTGTCTACCTGTGACAGAACTCGA
GAATGGAAGAATTGTGAGTGGTGCAGCAGAAACAGACCAGGAATACTATTTTGGACAGGTGG
TGCGGTTTGAATGCAATTCAGGCTTCAAGATTGAAGGACATAAGGAAATTCATTGCTCAGAAA
ATGGCCTTTGGAGCAATGAAAAGCCACGATGTGTGGAAATTCTCTGCACACCACCGCGAGTG
GAAAATGGAGATGGTATAAATGTGAAACCAGTTTACAAGGAGAATGAAAGATACCACTATAA
GTGTAAGCATGGTTATGTGCCCAAAGAAAGAGGGGATGCCGTCTGCACAGGCTCTGGATGGA
GTTCTCAGCCTTTCTGTGAAGAAAAGAGATGCTCACCTCCTTATATTCTAAATGGTATCTACAC
ACCTCACAGGATTATACACAGAAGTGATGATGAAATCAGATATGAATGTAATTATGGCTTCTA
TCCTGTAACTGGATCAACTGTTTCAAAGTGTACACCCACTGGCTGGATCCCTGTTCCAAGATGT
ACCGAAGATTGTAAAGGTCCTCCTCCAAGAGAAAATTCAGAAATTCTCTCAGGCTCGTGGTCA
GAACAACTATATCCAGAAGGCACCCAGGCTACCTACAAATGCCGCCCTGGATACCGAACACT
TGGCACTATTGTAAAAGTATGCAAGAATGGAAAATGGGTGGCGTCTAACCCATCCAGGATAT
GTCGGAAAAAGCCTTGTGGGCATCCCGGAGACACACCCTTTGGGTCCTTTAGGCTGGCAGTTG
GATCTCAATTTGAGTTTGGTGCAAAGGTTGTTTATACCTGTGATGATGGGTATCAACTATTAGG
TGAAATTGATTACCGTGAATGTGGTGCAGATGGCTGGATCAATGATATTCCACTATGTGAAGT
TGTGAAGTGTCTACCTGTGACAGAACTCGAGAATGGAAGAATTGTGAGTGGTGCAGCAGAAA
CAGACCAGGAATACTATTTTGGACAGGTGGTGCGGTTTGAATGCAATTCAGGCTTCAAGATTG
AAGGACATAAGGAAATTCATTGCTCAGAAAATGGCCTTTGGAGCAATGAAAAGCCACGATGT
GTGGAAATTCTCTGCACACCACCGCGAGTGGAAAATGGAGATGGTATAAATGTGAAACCAGT
TTACAAGGAGAATGAAAGATACCACTATAAGTGTAAGCATGGTTATGTGCCCAAAGAAAGAG
GGGATGCCGTCTGCACAGGCTCTGGATGGAGTTCTCAGCCTTTCTGTGAAGAAAAGAGATGCT
CACCTCCTTATATTCTAAATGGTATCTACACACCTCACAGGATTATACACAGAAGTGATGATG
AAATCAGATATGAATGTAATTATGGCTTCTATCCTGTAACTGGATCAACTGTTTCAAAGTGTA
CACCCACTGGCTGGATCCCTGTTCCAAGATGTACCTAA
```

Figure 11.

```
GAATTCGCCGCCACCATGCCCATGGGGTCTCTGCAACCGCTGGCCACCTTGTACCTGCTGGGG
ATGCTGGTCGCTTCCGTGCTAGCGATTTCTTGTGACCCTCCTCCTGAAGTCAAAAATGCTCGGA
AACCCTATTATTCTCTTCCCATAGTTCCTGGAACTGTTCTGAGGTACACTTGTTCACCTAGCTA
CCGCCTCATTGGAGAAAAGGCTATCTTTTGTATAAGTGAAAATCAAGTGCATGCCACCTGGGA
TAAAGCTCCTCCTATATGTGAATCTGTGAATAAAACCATTTCTTGCTCAGATCCCATAGTACCA
GGGGGATTCATGAATAAAGGATCTAAGGCACCATTCAGACATGGTGATTCTGTGACATTTACC
TGTAAAGCCAACTTCACCATGAAAGGAAGCAAAACTGTCTGGTGCCAGGCAAATGAAATGTG
GGGACCAACAGCTCTGCCAGTCTGTGAGAGTGATTTCCCTCTGGAGTGCCCATCACTTCCAAC
GATTCATAATGGACACCACACAGGACAGCATGTTGACCAGTTTGTTGCGGGGTTGTCTGTGAC
ATACAGTTGTGAACCTGGCTATTTGCTCACTGGAAAAAAGACAATTAAGTGCTTATCTTCAGG
AGACTGGGATGGTGTCATCCCGACATGCAAAGAGGCCCAGTGTGAACATCCAGGAAAGTTTC
CCAATGGGCAGGTAAAGGAACCTCTGAGCCTTCAGGTTGGCACAACTGTGTACTTCTCCTGTA
ATGAAGGGTACCAATTACAAGGACAACCCTCTAGTCAGTGTGTAATTGTTGAACAGAAAGCC
ATCTGGACTAAGAAGCCAGTATGTAAAGAAATTCTCGGCGGAGGTGGGTCGGGTGGCGGCGG
ATCTGAAGATTGTAAAGGTCCTCCTCCAAGAGAAAATTCAGAAATTCTCTCAGGCTCGTGGTC
AGAACAACTATATCCAGAAGGCACCCAGGCTACCTACAAATGCCGCCCTGGATACCGAACAC
TTGGCACTATTGTAAAAGTATGCAAGAATGGAAAATGGGTGGCGTCTAACCCATCCAGGATAT
GTCGGAAAAAGCCTTGTGGGCATCCCGGAGACACACCCTTTGGGTCCTTTAGGCTGGCAGTTG
GATCTCAATTTGAGTTTGGTGCAAAGGTTGTTTATACCTGTGATGATGGGTATCAACTATTAGG
TGAAATTGATTACCGTGAATGTGGTGCAGATGGCTGGATCAATGATATTCCACTATGTGAAGT
TGTGAAGTGTCTACCTGTGACAGAACTCGAGAATGGAAGAATTGTGAGTGGTGCAGCAGAAA
CAGACCAGGAATACTATTTTGGACAGGTGGTGCGGTTTGAATGCAATTCAGGCTTCAAGATTG
AAGGACATAAGGAAATTCATTGCTCAGAAAATGGCCTTTGGAGCAATGAAAAGCCACGATGT
GTGGAAATTCTCTGCACACCACCGCGAGTGGAAAATGGAGATGGTATAAATGTGAAACCAGT
TTACAAGGAGAATGAAAGATACCACTATAAGTGTAAGCATGGTTATGTGCCCAAAGAAAGAG
GGGATGCCGTCTGCACAGGCTCTGGATGGAGTTCTCAGCCTTTCTGTGAAGAAAAGAGATGCT
CACCTCCTTATATTCTAAATGGTATCTACACACCTCACAGGATTATACACAGAAGTGATGATG
AAATCAGATATGAATGTAATTATGGCTTCTATCCTGTAACTGGATCAACTGTTTCAAAGTGTA
CACCCACTGGCTGGATCCCTGTTCCAAGATGTACCGAAGATTGTAAAGGTCCTCCTCCAAGAG
AAAATTCAGAAATTCTCTCAGGCTCGTGGTCAGAACAACTATATCCAGAAGGCACCCAGGCTA
CCTACAAATGCCGCCCTGGATACCGAACACTTGGCACTATTGTAAAAGTATGCAAGAATGGA
AAATGGGTGGCGTCTAACCCATCCAGGATATGTCGGAAAAAGCCTTGTGGGCATCCCGGAGA
CACACCCTTTGGGTCCTTTAGGCTGGCAGTTGGATCTCAATTTGAGTTTGGTGCAAAGGTTGTT
TATACCTGTGATGATGGGTATCAACTATTAGGTGAAATTGATTACCGTGAATGTGGTGCAGAT
GGCTGGATCAATGATATTCCACTATGTGAAGTTGTGAAGTGTCTACCTGTGACAGAACTCGAG
AATGGAAGAATTGTGAGTGGTGCAGCAGAAACAGACCAGGAATACTATTTTGGACAGGTGGT
GCGGTTTGAATGCAATTCAGGCTTCAAGATTGAAGGACATAAGGAAATTCATTGCTCAGAAA
ATGGCCTTTGGAGCAATGAAAAGCCACGATGTGTGGAAATTCTCTGCACACCACCGCGAGTG
GAAAATGGAGATGGTATAAATGTGAAACCAGTTTACAAGGAGAATGAAAGATACCACTATAA
GTGTAAGCATGGTTATGTGCCCAAAGAAAGAGGGGATGCCGTCTGCACAGGCTCTGGATGGA
GTTCTCAGCCTTTCTGTGAAGAAAAGAGATGCTCACCTCCTTATATTCTAAATGGTATCTACAC
ACCTCACAGGATTATACACAGAAGTGATGATGAAATCAGATATGAATGTAATTATGGCTTCTA
TCCTGTAACTGGATCAACTGTTTCAAAGTGTACACCCACTGGCTGGATCCCTGTTCCAAGATGT
ACCTAA
```

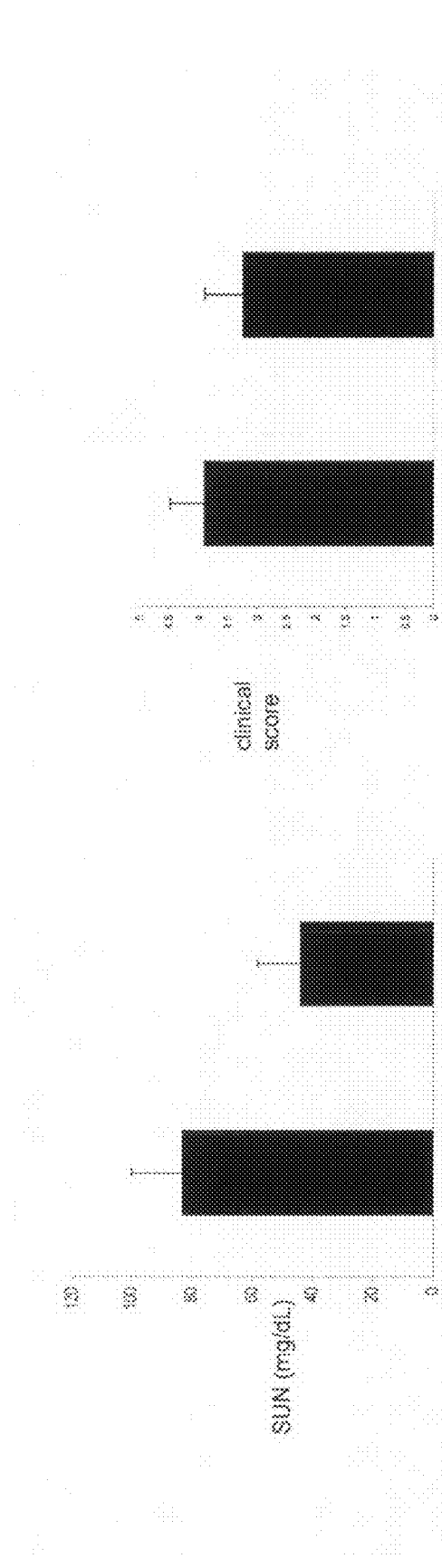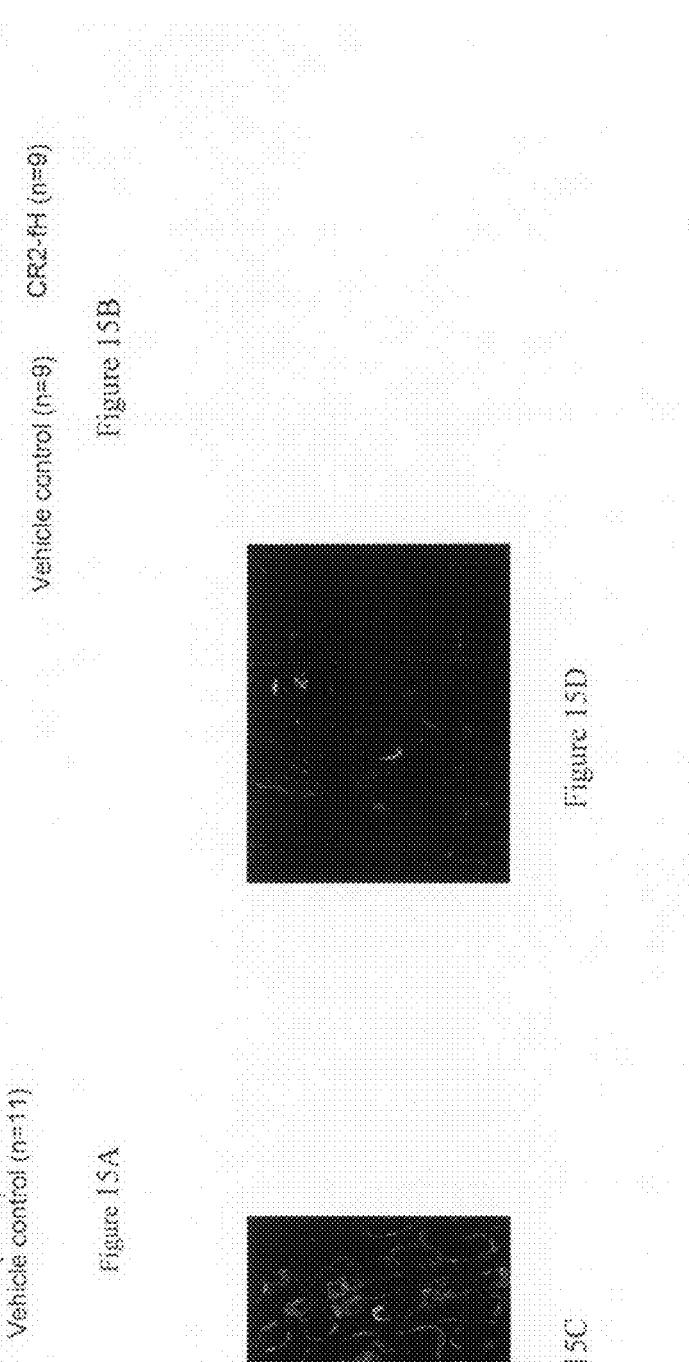

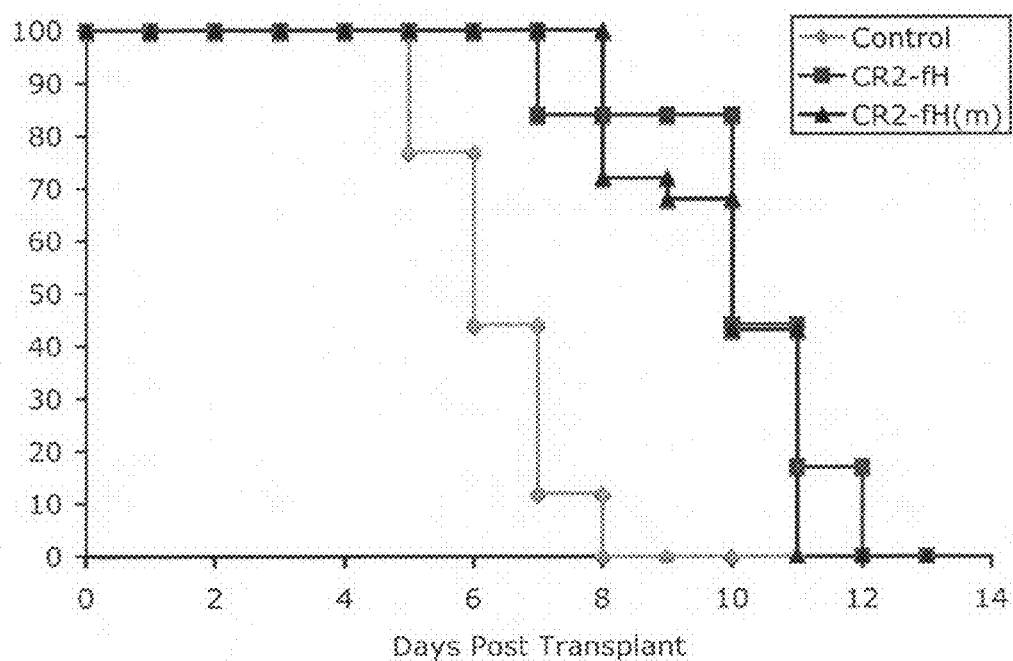

Figure 20

SEQ ID NO:21. human CR2-FH amino acid sequence

ISCGSPPPILNGRISYYSTPIAVGTVIRYSCSGTFRLIGEKSLLCITKDKVDGTWDKPAPKCEYFNKYS
SCPEPIVPGGYKIRGSTPYRHGDSVTFACKTNFSMNGNKSVWCQANNMWGPTRLPTCVSVFPLEC
PALPMIHNGHHTSENVGSIAPGLSVTYSCESGYLLVGEKIINCLSSGKWSAVPPTCEEARCKSLGRF
PNGKVKEPPILRVGVTANFFCDEGYRLQGPPSSRCVIAGQGVAWTKMPVCEEIFEDCNELPPRRNT
EILTGSWSDQTYPEGTQAIYKCRPGYRSLGNVIMVCRKGEWVALNPLRKCQKRPCGHPGDTPFGT
FTLTGGNVFEYGVKAVYTCNEGYQLLGEINYRECDTDGWTNDIPICEVVKCLPVTAPENGKIVSSA
MEPDREYHFGQAVRFVCNSGYKIEGDEEMHCSDDGFWSKEKPKCVEISCKSPDVINGSPISQKIIYK
ENERFQYKCNMGYEYSERGDAVCTESGWRPLPSCEEKSCDNPYIPNGDYSPLRIKHRTGDEITYQC
RNGFYPATRGNTAKCTSTGWIPAPRCTLK

SEQ ID NO:22. human CR2-FH DNA sequence (including signal peptide)
GCCGCcaCCATGGGAGCCGCTGGTCTGCTCGGCGTGTTCCTCGCCTTGGTGGCACCTGGCGTCC
TGGGCATCAGCTGCGGTTCCCCTCCACCAATCCTGAATGGCAGAATCTCCTATTACTCCACAC
CAATCGCCGTCGGCACTGTGATCAGATACAGCTGTTCAGGGACTTTTCGGCTGATCGGCGAGA
AAAGCCTCCTCTGCATTACCAAGGATAAGGTCGATGGGACATGGGATAAACCAGCTCCTAAG
TGCGAGTACTTCAATAAGTATAGTTCATGTCCAGAGCCCATTGTTCCTGGTGGCTACAAGATT
CGGGGGAGCACACCCTATCGCCACGGTGACTCAGTGACCTTTGCTTGTAAAACCAACTTCTCA
ATGAACGGTAATAAGTCAGTGTGGTGTCAGGCCAATAATATGTGGGGTCCTACACGACTCCCC
ACCTGTGTGTCCGTGTTCCCCTTGGAATGCCCCGCCCTGCCCATGATCCATAATGGACACCAC
ACCAGCGAGAATGTCGGGAGTATCGCACCTGGATTGAGTGTCACCTACTCATGCGAGTCTGGC
TACCTGCTTGTAGGTGAAAAAATTATTAATTGCTTGTCCTCCGGCAAATGGAGTGCCGTTCCCC
CAACTTGTGAAGAGGCCCGGTGCAAATCCCTCGGCCGCTTCCCTAATGGTAAAGTTAAAGAGC
CTCCAATCCTCAGAGTGGGGGTGACCGCTAACTTCTTCTGTGATGAAGGCTACCGGTTGCAGG
GACCACCCAGTAGCCGGTGTGTCATAGCTGGGCAGGGAGTGGCTTGGACAAAGATGCCCGTT
TGTGAGGAAATCTTCGAAGACTGTAATGAGCTGCCCCCAAGACGGAATACAGAGATCCTCAC
AGGCTCTTGGTCCGATCAAACTTATCCAGAGGGTACCCAGGCAATTTACAAGTGCAGACCTGG
ATACAGGAGCCTGGGCAATGTGATTATGGTGTGCCGCAAGGGGGAGTGGGTGGCCCTTAATC
CTCTCCGGAAGTGTCAGAAAAGACCATGCGGACACCCTGGAGATACACCTTTCGGTACCTTTA
CCCTTACCGGCGGCAATGTCTTCGAGTATGGCGTCAAGGCCGTGTACACTTGTAACGAGGGAT
ACCAGCTGCTGGGGGAAATAAACTATCGTGAGTGTGACACTGACGGGTGGACTAACGACATC
CCCATTTGCGAGGTGGTCAAGTGCCTTCCTGTAACCGCTCCCGAAAATGGTAAGATCGTATCT
TCCGCAATGGAGCCTGaTCGGGAATACcaCTTTGGACAAGCCGTTCGGTTCGTATGTAATTCAG
GGTATAAAATTGAGGGCGATGAGGAGATGCACTGCAGTGATGACGGCTTTTGGTCAAAGGAA
AAGCCAAAGTGCGTAGAGATCAGTTGTAAGTCTCCTGACGTTATTAACGGGAGTCCCATCAGT
CAGAAGATCATTTACAAGGAAAACGAGAGGTTCCAGTATAAATGCAATATGGGATATGAGTA
CTCCGAAAGAGGGGACGCCGTGTGCACAGAGTCCGGATGGCGACCTTTGCCATCTTGTGAAG
AAAAGTCTTGTGACAACCCCTATATTCCTAACGGAGATTACTCCTCTGCGCATCAAGCACC
GAACTGGGGACGAGATCACTTACCAATGTCGAAACGGCTTCTACCCTGCTACCAGAGGTAAC
ACTGCCAAGTGTACCAGCACCGGTTGGATTCCCGCCCCCAGATGCACACTTAAATGATAA

Figure 21.

SEQ ID NO: 23. human CR2-FH2 amino acid sequence

ISCGSPPPILNGRISYYSTPIAVGTVIRYSCSGTFRLIGEKSLLCITKDKVDGTWDKPAPKCEYFNKYSSCPEPIVP
GGYKIRGSTPYRHGDSVTFACKTNFSMNGNKSVWCQANNMWGPTRLPTCVSVFPLECPALPMIHNGHHTSE
NVGSIAPGLSVTYSCESGYLLVGEKIINCLSSGKWSAVPPTCEEARCKSLGRFPNGKVKEPPILRVGVTANFFC
DEGYRLQGPPSSRCVIAGQGVAWTKMPVCEEIFEDCNELPPRRNTEILTGSWSDQTYPEGTQAIYKCRPGYRS
LGNVIMVCRKGEWVALNPLRKCQKRPCGHPGDTPFGTFTLTGGNVFEYGVKAVYTCNEGYQLLGEINYREC
DTDGWTNDIPICEVVKCLPVTAPENGKIVSSAMEPDREYHFGQAVRFVCNSGYKIEGDEEMHCSDDGFWSKE
KPKCVEISCKSPDVINGSPISQKIIYKENERFQYKCNMGYEYSERGDAVCTESGWRPLPSCEEKSCDNPYIPNGD
YSPLRIKHRTGDEITYQCRNGFYPATRGNTAKCTSTGWIPAPRCTEDCNELPPRRNTEILTGSWSDQTYPEGTQ
AIYKCRPGYRSLGNVIMVCRKGEWVALNPLRKCQKRPCGHPGDTPFGTFTLTGGNVFEYGVKAVYTCNEGY
QLLGEINYRECDTDGWTNDIPICEVVKCLPVTAPENGKIVSSAMEPDREYHFGQAVRFVCNSGYKIEGDEEMH
CSDDGFWSKEKPKCVEISCKSPDVINGSPISQKIIYKENERFQYKCNMGYEYSERGDAVCTESGWRPLPSCEEK
SCDNPYIPNGDYSPLRIKHRTGDEITYQCRNGFYPATRGNTAKCTSTGWIPAPRCTLK

SEQ ID NO:24. human CR2-FH2 DNA sequence (including signal peptide)

CGCCGCCACC<u>ATGGGCGCAGCAGGCTTGTTGGGCGTGTTCCTGGCATTGGTGGCACCCGGCGTATTGGGC</u>
ATTTCATGCGGCTCTCCTCCACCCATTCTCAATGGAAGGATCTCCTACTACAGCACCCCCATAGCTGTCGG
CACCGTTATCCGATACAGTTGTTCCGGTACTTTCCGGCTTATCGGCGAAAAGTCTTTGCTGTGCATTACCA
AGGATAAAGTGGACGGGACTTGGGACAAACCCGCACCTAAGTGCGAGTATTTTAACAAATATAGCAGCT
GCCCTGAGCCTATAGTACCCGGGGGGTATAAAATCCGGGGCTCTACTCCCTATCGTCATGGCGATTCTGT
GACCTTCGCATGTAAAACTAATTTTTCAATGAATGGCAACAAGTCTGTATGGTGTCAAGCAAATAACATG
TGGGGACCTACCCGCCTGCCAACCTGTGTGTCAGTGTTTCCCCTGGAATGTCCAGCCCTCCCTATGATCCA
CAACGGACATCACACCAGCGAAAACGTTGGATCCATCGCACCAGGGCTCTCTGTGACTTACTCTTGCGAG
TCCGGGTACCTGCTCGTGGGTGAAAAGATCATCAACTGCCTCAGTAGTGGTAAATGGTCCGCCGTGCCTC
CCACATGTGAAGAGGCCCGGTGCAAGAGCCTGGGCCGGTTCCCCAACGGAAAAGTGAAGGAACCTCCTA
TCTTGAGGGTTGGTGTGACCGCTAACTTTTTCTGCGACGAGGGGTACAGGCTCCAAGGGCCTCCCTCTAG
TCGGTGCGTAATCGCCGGTCAAGGAGTCGCATGGACTAAGATGCCTGTGTGTGAGGAGATTTTCGAGGAT
TGTAATGAATTGCCACCCAGGAGAAATACTGAAATCCTGACAGGCTCTTGGTCTGATCAGACTTATCCAG
AAGGCACCCAGGCCATTTACAAGTGTCGGCCTGGATACAGATCTCTGGGAAATGTGATCATGGTATGTAG
GAAAGGAGAGTGGGTGGCTTTGAACCCCCTCCGCAAGTGTCAGAAAAGACCATGCGGGCATCCTGGAGA
CACCCCATTCGGGACATTTACACTGACAGGCGGAAACGTATTTGAGTACGGAGTCAAGGCCGTTTATACA
TGTAACGAAGGGTATCAACTGCTGGGAGAAATCAACTATAGGGAGTGCGACACTGACGGATGGACAAAC
GACATTCCAATCTGCGAAGTGGTGAAATGTCTTCCAGTTACAGCCCCTGAAAACGGGAAAATCGTGTCCT
CCGCTATGGAGCCTGACCGGGAATATCATTTCGGCCAGGCCGTTAGATTCGTGTGTAATAGCGGCTACAA
AATCGAGGGCGACGAAGAAATGCATTGCAGCGATGACGGGTTCTGGAGCAAGGAGAAGCCTAAATGCGT
CGAAATTTCATGCAAGAGTCCCGACGTCATAAACGGTTCTCCAATTTCCCAGAAGATCATTTATAAGGAG
AATGAGCGGTTCCAGTATAAGTGTAATATGGGCTACGAGTACAGCGAACGCGGTGACGCCGTGTGTACC
GAAAGTGGCTGGAGACCACTGCCTAGTTGCGAGGAGAAATCCTGCGACAACCCTTATATTCCCAACGGG
GACTACTCTCCTCTGAGAATCAAGCATCGGACTGGCGACGAGATTACTTACCAATGCAGGAACGGATTCT
ATCCAGCAACTCGGGGCAATACCGCTAAGTGTACCTCCACAGGCTGGATACCCGCTCCTAGATGTACAGA
GGACTGCAATGAACTGCCACCTCGGCGCAATACAGAAATTTTGACTGGATCATGGTCTGACCAGACTTAC
CCCGAGGGCACCCAGGCCATCTACAAATGTAGGCCCGGTTATCGAAGTTTGGGTAACGTGATTATGGTGT
GTCGAAAAGGTGAATGGGTAGCACTCAATCCCCTCCGTAAATGCCAGAAGCGTCCTTGTGGGCACCCAG
GCGATACCCCTTTTGGAACTTTCACCCTGACTGGAGGAAACGTCTTTGAATATGGTGTGAAAGCCGTGTA
CACATGCAATGAAGGGTACCAACTGCTCGGAGAGATAAACTATCGGGAGTGCGATACAGATGGATGGAC
CAATGATATACCAATCTGCGAGGTGGTGAAGTGTCTCCCAGTCACCGCTCCTGAGAACGGAAAGATCGTC
AGTTCTGCTATGGAACCTGACAGGGAATACCACTTTGGGCAAGCCGTCCGCTTCGTGTGCAATTCAGGGT
ACAAGATAGAAGGCGACGAAGAGATGCACTGTTCCGACGATGGTTTCTGGTCTAAGGAGAAGCCTAAAT
GTGTCGAGATTAGCTGCAAGTCTCCCGATGTTATTAACGGCTCTCCCATCTCTCAAAAAAATTATTTATAAG
GAAAACGAAAGATTTCAGTACAAGTGCAATATGGGTTATGAGTACAGTGAACGTGGGAGACGCCGTGTGC
ACAGAGTCCGGGTGGCGTCCACTGCCCAGCTGCGAAGAAAAATCCTGTGACAACCCCTACATCCCCAAT
GGCGACTATTCCCCCCTGCGCATCAAACATCGTACTGGCGATGAAATTACTTACCAGTGCCGCAACGGGT
TCTACCCTGCCACCCGGGGTAACACAGCCAAATGCACCTCCACCGGATGGATCCCCGCCCCACGCTGTAC
CTTGAAATGATGA

TARGETING COMPLEMENT FACTOR H FOR TREATMENT OF DISEASES

RELATED APPLICATIONS

This application claims priority benefit to provisional patent application No. 60/815,748, filed on Jun. 21, 2006, the content of which is incorporated by reference in its entirety.

STATEMENT REGARDING FEDERALLY SPONSORED RESEARCH OR DEVELOPMENT

This invention was made with Government support under Grant (Contract) Nos.: AI47469, AI31105, and EY13520 awarded by the National Institutes of Health.

TECHNICAL FIELD

This application pertains to compositions and methods of treating diseases in which the alternative complement pathway is implicated. Specifically, the application pertains to a CR2-FH molecule and uses thereof for treating diseases in which the alternative complement pathway is implicated.

BACKGROUND

Complement is the collective term for a series of blood proteins and is a major effector mechanism of the immune system. Complement plays an important role in the pathology of many autoimmune, inflammatory, and ischemic diseases, and is also responsible for many disease states associated with bioincompatibility. Inappropriate complement activation and its deposition on host cells can lead to complement-mediated cell lysis of target structures, as well as tissue destruction due to the generation of powerful mediators of inflammation.

Complement can be activated by one of the three pathways, the classical, lectin, and alternative pathways. The classical pathway is activated through the binding of the complement system protein C1q to antigen-antibody complexes, pentraxins, or apoptotic cells. The pentraxins include C-reactive protein and serum amyloid P component. The lectin pathway is initiated by microbial saccharides via the mannose-binding lectin. The alternative pathway is activated on surfaces of pathogens that have neutral or positive charge characteristics and do not express or contain complement inhibitors. This is due to the process termed "tickover" of C3 that occurs spontaneously, involving the interaction of conformationally altered C3 with factor B, and results in the fixation of active C3b on pathogens or other surfaces. The alternative pathway can also be initiated when certain antibodies block endogenous regulatory mechanisms, by IgA-containing immune complexes, or when expression of complement regulatory proteins is decreased. In addition, the alternative pathway is activated by a mechanism called the "amplification loop" when C3b that is deposited onto targets via the classical or lectin pathway then binds factor B. Muller-Eberhard, 1988, *Ann. Rev. Biochem.* 57:321. For example, Holers and collaborators have shown that the alternative pathway is amplified at sites of local injury when inflammatory cells are recruited following initial complement activation. Girardi et al., *J. Clin. Invest.* 2003, 112:1644. Dramatic complement amplification through the alternative pathway then occurs through a mechanism that involves either the additional generation of injured cells that fix complement, local synthesis of alternative pathway components, or more likely because these infiltrating inflammatory cells that carry preformed C3 and properdin greatly increase activation specifically at that site.

Alternative pathway activation is initiated when circulating factor B binds to activated C3. This complex is then cleaved by circulating factor D to yield an enzymatically active fragment, C3bBb. C3bBb cleaves C3 generating C3b, which drives inflammation and also further amplifies the activation process, generating a positive feedback loop. Factor H (FH) is a key regulator (inhibitor) of the alternative complement pathway. It functions by competing with factor B for binding to C3b. Binding of C3b to Factor H also leads to degradation of C3b by factor I to the inactive form C3bi (also designated iC3b), thus exerting a further check on complement activation. The actual plasma concentration of factor H is approximately 500 μg/ml, providing complement regulation in the fluid phase, but its binding to cells is a regulated phenomenon that is enhanced by the presence of a negatively charged surface as well as fixed C3b, C3bi, or C3d. Jozsi et al., *Histopathol* (2004) 19:251-258.

The down-regulation of complement activation has been demonstrated to be effective in treating several disease indications in animal models and in ex vivo studies, e.g. systemic lupus erythematosus and glomerulonephritis (Y. Wang et al., *Proc. Natl. Acad. Sci.;* 1996, 93: 8563-8568), rheumatoid arthritis (Y. Wang et al., *Proc. Natl. Acad. Sci.,* 1995; 92: 8955-8959), cardiopulmonary bypass and hemodialysis (C. S. Rinder, *J. Clin. Invest.,* 1995; 96: 1564-1572), hypercute rejection in organ transplantation (T. J. Kroshus et al., *Transplantation,* 1995; 60: 1194-1202), myocardial infarction (J. W. Homeister et al., *J. Immunol,* 1993; 150: 1055-1064; H. F. Weisman et al., *Science,* 1990; 249: 146-151), reperfusion injury (E. A. Amsterdam et al., *Am. J. Physiol.,* 1995; 268: H448-H457), and adult respiratory distress syndrome (R. Rabinovici et al., *J. Immunol.,* 1992; 149: 1744-1750). In addition, other inflammatory conditions and autoimmune/immune complex diseases are also closely associated with complement activation (B. P. Morgan. *Eur. J Clin. Invest.,* 1994: 24: 219-228), including thermal injury, severe asthma, anaphylactic shock, bowel inflammation, urticaria, angioedema, vasculitis, multiple sclerosis, myasthenia gravis, membranoproliferative glomerulonephritis, and Sjogren's syndrome. Complement inhibitors and uses thereof are also disclosed in WO04/045520 and U.S. Pat. No. 6,521, 450.

The disclosures of all publications, patents, patent applications and published patent applications referred to herein are hereby incorporated herein by reference in their entirety.

BRIEF SUMMARY OF THE INVENTION

The invention in one aspect provides a CR2-FH molecule comprising: a) a CR2 portion comprising a CR2 or a fragment thereof, and b) a FH portion comprising a FH or a fragment thereof. In some embodiments, there is provided a CR2-FH molecule comprising: a) a CR2 portion comprising a CR2 or a fragment thereof, and b) a FH portion comprising a FH or a fragment thereof, wherein the CR2-FH molecule is capable of binding to a CR2 ligand and wherein the CR2-FH molecule is capable of inhibiting complement activation of the alternative pathway. In some embodiments, there is provided an isolated CR2-FH molecule. In some embodiments, there is provided a composition (such as a pharmaceutical composition) comprising a CR2-FH molecule. In some embodiments, the CR2 portion and the FH portion are directly or indirectly fused to each other in the form of a fusion protein. In some embodiments, the CR2 portion and the FH portion are linked via a chemical crosslinker. In some embodiments, the CR2 portion and the FH portion are non-covalently linked.

In some embodiments, there is provided a CR2-FH fusion protein comprising: a) a CR2 portion comprising a CR2 or a fragment thereof, and b) a FH portion comprising a FH or a fragment thereof. In some embodiments, there is provided a CR2-FH molecule comprising: a) a CR2 portion comprising a CR2 or a fragment thereof, and b) a FH portion comprising a FH or a fragment thereof, wherein the CR2-FH molecule is capable of binding to a CR2 ligand and wherein the CR2-FH molecule is capable of inhibiting complement activation of the alternative pathway. In some embodiments, the CR2 portion and the FH portion are directly fused (i.e., linked) to each other. In some embodiments, the CR2 portion and the FH portion are linked via an amino acid linker sequence. In some embodiments, the C-terminus of the CR2 portion is linked (directly or indirectly) to the N-terminus of the FH portion. In some embodiments, the N-terminus of the CR2 portion is linked (directly or indirectly) to the C-terminus of the FH portion.

In some embodiments, the CR2-FH molecule comprises two or more (such as any of two, three, four, five, or more) CR2 portions. These CR2 portions may be the same or different, for example in terms of amino acid sequences, structures, and/or functions. For example, in some embodiments, the CR2-FH molecule (such as a CR2-FH fusion protein) comprises: 1) two or more CR2 portions comprising a CR2 or a fragment thereof, and 2) an FH portion comprising a FH or a fragment thereof. In some embodiments, the CR2-FH molecule (such as a CR2-FH fusion protein) comprises: 1) two or more CR2 portions comprising a CR2 or a fragment thereof, and 2) an FH portion comprising a FH or a fragment thereof, wherein the CR2-FH molecule is capable of binding to a CR2 ligand and wherein the CR2-FH molecule is capable of inhibiting complement activation of the alternative pathway.

In some embodiments, the CR2-FH molecule comprises two or more (such as any of two, three, four, five, or more) FH portions. These FH portions may be the same or different, for example in terms of amino acid sequences, structures, and/or functions. For example, in some embodiments, the CR2-FH molecule (such as a CR2-FH fusion protein) comprises: 1) a CR2 portion comprising a CR2 or a fragment thereof, and 2) two or more FH portions comprising a FH or a fragment thereof. In some embodiments, the CR2-FH molecule (such as a CR2-FH fusion protein) comprises: 1) a CR2 portion comprising a CR2 or a fragment thereof, and 2) two or more (such as two) FH portions comprising a FH or a fragment thereof, wherein the CR2-FH molecule is capable of binding to a CR2 ligand and wherein the CR2-FH molecule is capable of inhibiting complement activation of the alternative pathway.

In some embodiments, the CR2-FH molecule (such as a CR2-FH fusion protein) comprises: 1) two or more CR2 portions comprising a CR2 or a fragment thereof, and 2) two or more FH portions comprising a FH or a fragment thereof. In some embodiments, the CR2-FH molecule (such as a CR2-FH fusion protein) comprises: 1) two or more CR2 portions comprising a CR2 or a fragment thereof, and 2) two or more (such as two) FH portions comprising a FH or a fragment thereof, wherein the CR2-FH molecule is capable of binding to a CR2 ligand and wherein the CR2-FH molecule is capable of inhibiting complement activation of the alternative pathway.

In some embodiments, the CR2-FH molecule (such as a CR2-FH fusion protein) comprises: 1) full length CR2; and 2) a FH portion comprising a FH or a fragment thereof. In some embodiments, the CR2-FH molecule (such as a CR2-FH fusion protein) comprises: 1) a fragment of CR2, and 2) a FH portion comprising a FH or a fragment thereof. In some embodiments, the CR2-FH molecule (such as a CR2-FH fusion protein) comprises: 1) a CR2 portion comprising at least the first two N-terminal SCR domains of CR2, and b) a FH portion comprising a FH or a fragment thereof. In some embodiments, the CR2-FH molecule (such as a CR2-FH fusion protein) comprises: 1) a CR2 portion comprising at least the first four N-terminal SCR domains of CR2, and b) a FH portion comprising a FH or a fragment thereof. In some embodiments, the CR2-FH molecule is capable of binding to a CR2 ligand and inhibiting complement activation of the alternative pathway. In some embodiments, the CR2-FH molecule comprises two or more FH portions. In some embodiments, the FH portion comprises a full length FH. In some embodiments, the FH portion comprises a fragment of FH. In some embodiments, the FH portion comprises at least the first four N-terminal SCR domains of FH. In some embodiments, the FH portion comprises at least the first five N-terminal SCR domains of FH. In some embodiments, the FH portion lacks a heparin binding site. In some embodiments, the FH portion comprises a FH or a fragment thereof having a polymorphism that is protective against age-related macular degeneration.

In some embodiments, there is provided a CR2-FH molecule (such as a CR2-FH fusion protein) comprising: a) CR2 portion comprising a ligand binding site that is any of (and in some embodiments selected from the group consisting of) (1) a site on strand B and the B-C loop of CR2 SCR comprising the segment G98-G99-Y100-K101-I1102-R103-G104-S105-T106-P107-Y108 with respect to SEQ ID NO:1, (2) a site on the B strand of CR2 SCR2 comprising position K119 with respect to SEQ ID NO:1, (3) a segment comprising V149-F150-P151-L152 with respect to SEQ ID NO:1, and (4) a segment of CR2 SCR2 comprising T120-N121-F122 with respect to SEQ ID NO:1; and (b) a FH portion comprising a FH or a fragment thereof. In some embodiments, the CR2-FH molecule is capable of binding to a CR2 ligand and inhibiting complement activation of the alternative pathway. In some embodiments, the CR2 portion further comprises sequences required to maintain the three dimensional structure of the ligand binding site. In some embodiments, the CR2-FH molecule comprises two or more FH portions. In some embodiments, the FH portion comprises a full length FH. In some embodiments, the FH portion comprises a fragment of FH. In some embodiments, the FH portion comprises at least the first four N-terminal SCR domains of FH. In some embodiments, the FH portion comprises at least the first five N-terminal SCR domains of FH. In some embodiments, the FH portion lacks a heparin binding site. In some embodiments, the FH portion comprises a FH or a fragment thereof having a polymorphism that is protective against age-related macular degeneration.

In some embodiments, there is provided a CR2-FH molecule (such as a CR2-FH fusion protein) comprising: a) a CR2 portion comprising at least the first two N-terminal SCR domains of CR2, and b) a FH portion comprising at least the first four N-terminal SCR domains of FH. In some embodiments, the CR2-FH molecule is capable of binding to a CR2 ligand and inhibiting complement activation of the alternative pathway. In some embodiments, the CR2 portion comprises at least the first 3, 4, 5, 6, 7, or more N-terminal SCR domains of CR2. In some embodiments, the FH portion comprises at least the first 5, 6, 7, 8, 9, 10, 11, 12, 13, 14, or more N-terminal SCR domains of FH. In some embodiments, the CR2-FH molecule (such as a CR2-FH fusion protein) comprises (and in some embodiments consists of or consists essentially of): a) a CR2 portion comprising the first four N-terminal SCR domains of CR2, and b) a FH portion comprising the first five N-terminal SCR domains of FH. In some embodiments, the CR2-FH molecule (such as a CR2-FH fusion protein) comprises (and in some embodiments consists of or consists essentially of): a) a CR2 portion comprising the first four N-terminal SCR domains of CR2, and b) two or more (such as two) FH portions comprising the first five N-terminal SCR domains of FH. In some embodiments, the CR2-FH molecule comprises (and in some embodiments consists of or consists essentially of): a) a CR2 portion comprising amino acids 23 to 271 of SEQ ID NO:1, and b) a FH portion comprising amino acids 21 to 320 of SEQ ID NO:2. In some embodiments, the CR2-FH molecule comprises (and in some embodiments consists of or consists essentially of): a) a CR2 portion comprising amino acids 23 to 271 of SEQ ID NO:1, and b) two or more (such as two) FH portions comprising amino acids 21 to 320 of SEQ ID NO:2.

In some embodiments, the CR2-FH is a fusion protein having an amino acid sequence of any of SEQ ID NO:3, SEQ ID NO:21, and SEQ ID NO:23. In some embodiments, the CR2-FH molecule is a fusion protein having amino acid sequence that is at least about any of 50%, 60%, 70%, 80%, 90%, 91%, 92%, 93%, 94%, 95%, 96%, 97%, 98%, or 99% identical to that of any of SEQ ID NO:3, SEQ ID NO:21, and SEQ ID NO:23. In some embodiments, the CR2-FH is a fusion protein comprising at least about 400, 450, 500, 550, or more contiguous amino acids of any of SEQ ID NO:3, SEQ ID NO:21, and SEQ ID NO:23. In some embodiments, the CR2-FH molecule is a fusion protein encoded by a polynucleotide having nucleic acid sequence of any of SEQ ID NO:4, SEQ ID NO:22, and SEQ ID NO:24. In some embodiments, the CR2-FH molecule is a fusion protein encoded by a polynucleotide having a nucleic acid sequence that is at least about any of 50%, 60%, 70%, 80%, 90%, 91%, 92%, 93%, 94%, 95%, 96%, 97%, 98%, or 99% identical to that of any of SEQ ID NO:4, SEQ ID NO:22, and SEQ ID NO:24. Also encompassed herein are polynucleotides encoding a CR2-FH fusion protein described herein. For example, in some embodiments, there is provided a polynucleotide encoding a fusion protein comprising a CR2 portion comprising CR2 or a fragment thereof and a FH portion comprising a FH or a fragment thereof. In some embodiments, the polynucleotide also comprises a sequence encoding a signal peptide operably linked at the 5' end of the sequence encoding the CR2-FH fusion protein. In some embodiments, a linker sequence is used for linking the CR2 portion and the FH portion. In some embodiments, the polynucleotide encodes a CR2-FH fusion protein having an amino acid sequence of any of SEQ ID NO:3, SEQ ID NO:21, and SEQ ID NO:23. In some embodiments, the polynucleotide encodes a CR2-FH fusion protein having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the nucleic acid sequence of any of SEQ ID NO:3, SEQ ID NO:22, and SEQ ID NO:24. Also provided are vectors comprising a polynucleotide encoding a CR2-FH fusion protein, host cells comprising the polynucleotide, and methods of producing a CR2-FH fusion protein comprising culturing the host cells under suitable conditions to express the fusion protein and recovering the fusion protein from the host cell culture.

In another aspect, there is provided a pharmaceutical composition comprising a CR2-FH molecule and a pharmaceutically acceptable carrier. In some embodiments, the pharmaceutical composition comprises a CR2-FH molecule and a pharmaceutically acceptable carrier suitable for administration to a human. In some embodiments, the pharmaceutical composition comprises a CR2-FH molecule and a pharmaceutically acceptable carrier suitable for intraocular injection. In some embodiments, the pharmaceutical composition comprises a CR2-FH molecule and a pharmaceutically acceptable carrier suitable for topical application to the eye. In some embodiments, the pharmaceutical composition comprises a CR2-FH molecule and a pharmaceutically acceptable carrier suitable for intravenous injection. In some embodiments, the pharmaceutical composition comprises a CR2-FH molecule and a pharmaceutically acceptable carrier suitable for injection into the arteries (such as renal arteries), liver, or kidney.

In some embodiments, the pharmaceutical composition comprises a CR2-FH molecule (such as a CR2 fusion protein) comprising: a) a CR2 portion comprising a CR2 or a fragment thereof, and b) a FH portion comprising a FH or a fragment thereof, and a pharmaceutically acceptable carrier. In some embodiments, the CR2-FH molecule is capable of binding to a CR2 ligand and inhibiting complement activation of the alternative pathway. In some embodiments, the pharmaceutical composition comprises a CR2-FH molecule comprising: a CR2-FH molecule (such as a CR2-FH fusion protein) comprising: a) a CR2 portion comprising at least the first two N-terminal SCR domains of CR2, and b) a FH portion comprising at least the first four N-terminal SCR domains of FH, and a pharmaceutically acceptable carrier. In some embodiments, the pharmaceutical composition comprises a CR2-FH molecule (such as a CR2-FH fusion protein) comprising (and in some embodiments consists of or consists essentially of): a) a CR2 portion comprising the first four N-terminal SCR domains of CR2, and b) a FH portion comprising the first five N-terminal SCR domains of FH, and a pharmaceutically acceptable carrier. In some embodiments, the pharmaceutical composition comprises a CR2-FH molecule (such as a CR2-FH fusion protein) comprising (and in some embodiments consists of or consists essentially of): a) a CR2 portion comprising amino acids 23 to 271 of SEQ ID NO:1, and b) a FH portion comprising amino acids 21 to 320 of SEQ ID NO:2, and a pharmaceutically acceptable carrier. In some embodiments, the pharmaceutical composition comprises a CR2-FH fusion protein having an amino acid sequence that is at least about 50%, 60%, 70%, 80%, 90%, 91%, 92%, 93%, 94%, 95%, 96%, 97%, 98%, or 99% identical to that of any of SEQ ID NO:3, SEQ ID NO:21, and SEQ ID NO:23, and a pharmaceutically acceptable carrier. In some embodiments, the pharmaceutical composition is suitable for delivery to the eye (for example by intraocular injection or by topical delivery to the eye). In some embodiments, the pharmaceutical composition is suitable for intravenous injection. In some embodiments, the pharmaceutical composition is suitable for injection into arteries (such as renal arteries), liver, or kidney. In some embodiments, the composition is suitable for intraocular, intravenous, intraarterial, sub-cutaneous, intratracheal, or inhalational administration.

In another aspect, the invention provides a method of treating a disease in which the alternative complement pathway is implicated in an individual, comprising administering to the individual an effective amount of a composition (such as a pharmaceutical composition) described herein. In some embodiments, the method comprises administering to the individual an effective amount of a composition comprising a CR2-FH molecule comprising: a) a CR2 portion comprising a CR2 or a fragment thereof, and b) a FH portion comprising a FH or a fragment thereof. In some embodiments, the method comprises administering to the individual an effective amount of a composition comprising a CR2-FH molecule comprising: a) a CR2 portion comprising a CR2 or a fragment thereof, and b) a FH portion comprising a FH or a fragment thereof, wherein the CR2-FH molecule is capable of binding to a CR2 ligand and wherein the CR2-FH molecule is capable of inhibiting complement activation of the alternative pathway. In some embodiments, the disease to be treated is a disease that involves local inflammation. In some embodiments, the disease to be treated is a disease that is associated with FH deficiencies (including for example decrease in level of FH, decrease in activity of FH, or lacking wildtype or protective FH). In some embodiments, the disease to be treated is not a disease that is associated with FH deficiencies. In some embodiments, the disease to be treated is a drusen-associated disease. In some embodiments, the disease to be treated does not involve the classical complement pathway.

In some embodiments, there is provided a method of treating macular degeneration (such as age-related macular degeneration or AMD) in an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, the disease to be treated is a dry form of AMD. In some embodiments, the disease to be treated is a wet form of AMD. In some embodiments, the CR2-FH molecule is administered by intravenous administration. In some embodiments, the CR2-FH molecule is administered by intraocular injection. In some embodiments, the CR2-FH molecule is administered by topical administration to the eye (for example in the form of eye drops).

In some embodiments, one or more aspects of AMD are treated by methods of the present invention. For example, in some embodiments, there is provided a method of treating (such as reducing, delaying, eliminating, or preventing) formation of drusen in the eye of an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there is provided a method of treating (such as reducing, delaying, eliminating, or preventing) inflammation in the eye of an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there is provided a method of treating (such as reducing, delaying, eliminating, or preventing) loss of photoreceptors cells in an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there is provided a method of improving (including for example decreasing, delaying, or blocking loss of) visual acuity or visual field in the eye of an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there is provided a method of treating neovascularization (such as choroidal neovascularization or CNV), comprising administering to the individual an effective amount of a composition comprising a CR2-FH molecule comprising: a) a CR2 portion comprising a CR2 or a fragment thereof, and b) a FH portion comprising a FH or a fragment thereof. Treatments of other aspects of AMD are also contemplated.

The methods described herein are also useful for treatment of certain renal diseases. For example, in some embodiments, there is provided a method of treating membranoproliferative glomerulonephritis type II (MPGN II), comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there is provided a method of treating hemolytic-uremic syndrome (HUS), comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there is provided a method of treating lupus nephritis, comprising administering to the individual an effective amount of a composition comprising a CR2-FH molecule comprising: a) a CR2 portion comprising a CR2 or a fragment thereof, and b) a FH portion comprising a FH or a fragment thereof.

In some embodiments, there is provided a method of treating ischemia reperfusion (including for example renal ischemia reperfusion and intestinal ischemia reperfusion), comprising administering to the individual an effective amount of a composition comprising a CR2-FH molecule comprising: a) a CR2 portion comprising a CR2 or a fragment thereof, and b) a FH portion comprising a FH or a fragment thereof.

Also provided are methods of treating organ transplant rejections. For example, in some embodiments, there is provided a method of delaying onset of acute vascular rejection (such as antibody-mediated rejection of heart transplant) in an individual, comprising administering to the individual an effective amount of a composition comprising a CR2-FH molecule comprising: a) a CR2 portion comprising a CR2 or a fragment thereof, and b) a FH portion comprising a FH or a fragment thereof.

In some embodiments, there is provided a method of improving organ transplant survival in an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there is provided a method of improving organ transplant survival in an individual, the method comprises perfusing the organ to be transplanted to an individual with a composition comprising a CR2-FH molecule comprising: a) a CR2 portion comprising a CR2 or a fragment thereof, and b) a FH portion comprising a FH or a fragment thereof. In some embodiments, there is provided a method of improving survival of an organ transplant donor, comprising administering to the organ transplant donor an effective amount of a composition comprising a CR2-FH molecule comprising: a) a CR2 portion comprising a CR2 or a fragment thereof, and b) a FH portion comprising a FH or a fragment thereof.

In some embodiments, there is provided a method of treating rheumatoid arthritis, comprising administering to the individual an effective amount of a composition comprising a CR2-FH molecule comprising: a) a CR2 portion comprising a CR2 or a fragment thereof, and b) a FH portion comprising a FH or fragment thereof.

Also provided are unit dosage forms, kits, and articles of manufacture that are useful for methods described herein.

It is to be understood that one, some, or all of the properties of the various embodiments described herein may be combined to form other embodiments of the present invention.

FH expression plasmid, k refers to Kozak sequence, 5 refers to CD5 signal peptide, l refers to an optional linker, s refers to stop codon and poly A signal. For the CR2-FH proteins (with or without signal peptide), 5 refers to the CD5 signal peptide, l refers to an optional linker.

FIG. 2 provides the amino acid sequence of human CR2 (SEQ ID NO:1) and the amino acid sequence of human FH (SEQ ID NO:2).

FIG. 3 provides the amino acid sequence of an exemplary human CR2-FH fusion protein (SEQ ID NO:3) and an exemplary polynucleotide sequence encoding a human CR2-FH fusion protein (SEQ ID NO:4).

FIGS. 4-6 provide exemplary amino acid sequences of CR2-FH molecules described herein (SEQ ID NOs: 5-10). "nnn" represents an optional linker.

FIG. 7 provides exemplary amino acid sequences of signaling peptides described herein (SEQ ID NOs: 11, 13, and 25) and exemplary polynucleotide sequences encoding the signaling peptides (SEQ ID NOs:12, 14, and 26).

FIG. 8 provides amino acid sequence of mouse CR2 (SEQ ID NO:15) and amino acid sequence of mouse FH (SEQ ID NO:16).

FIG. 9 provides amino acid sequence of an exemplary mouse CR2-FH fusion protein (SEQ ID NO:17) and an exemplary polynucleotide sequence that encodes a mouse CR2-FH plus the signal peptide (SEQ ID NO:18).

FIG. 10 provides an exemplary DNA sequence of CR2NLFHFH, a mouse CR2-FH fusion protein containing a CR2 portion and two FH portions without a linker sequence (SEQ ID NO:19).

FIG. 11 provides an exemplary DNA sequence of CR2LFHFH, a mouse CR2-FH fusion protein containing a CR2 portion linked to two FH portions via a linker sequence (SEQ ID NO:20).

Figure 1:
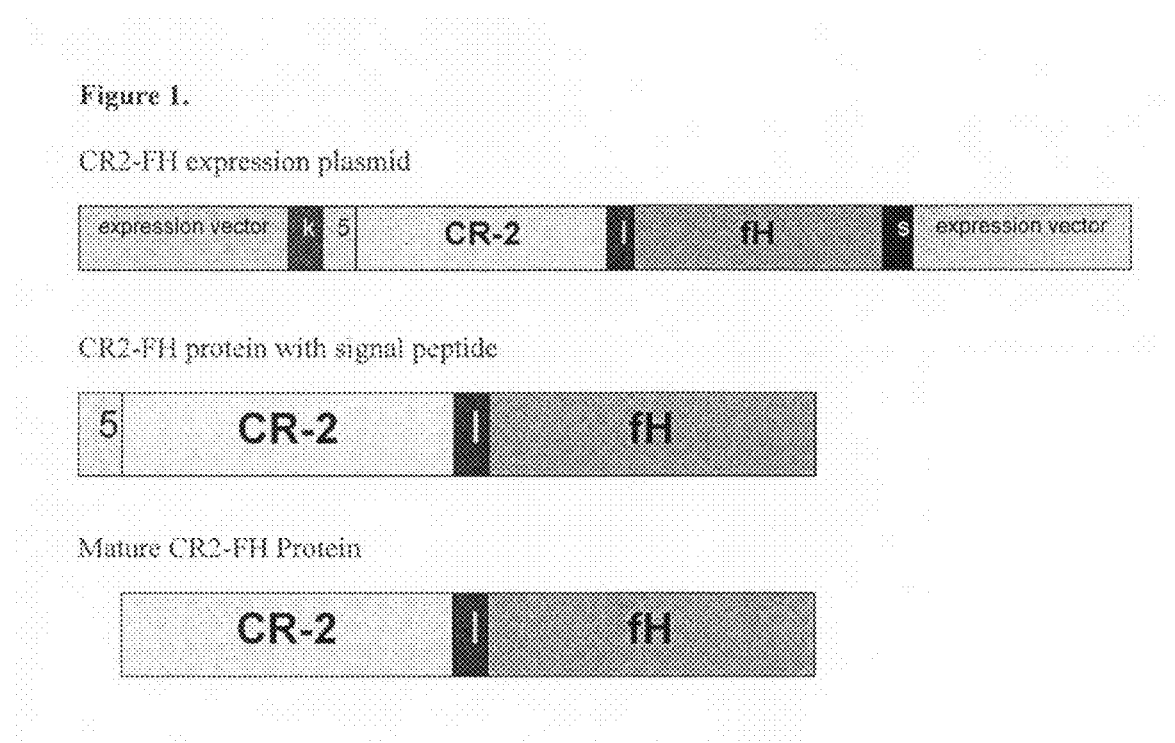
FIG. 1 provides schematic diagrams of an exemplary CR2-FH expression plasmid and CR2-FH proteins. For the CR2-
Figure 12A:
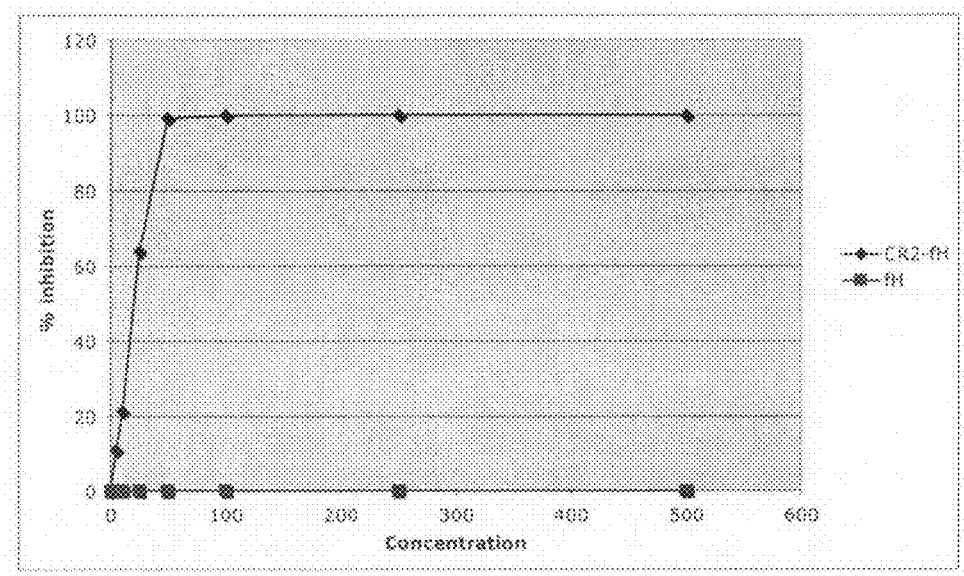
Figure 12B:
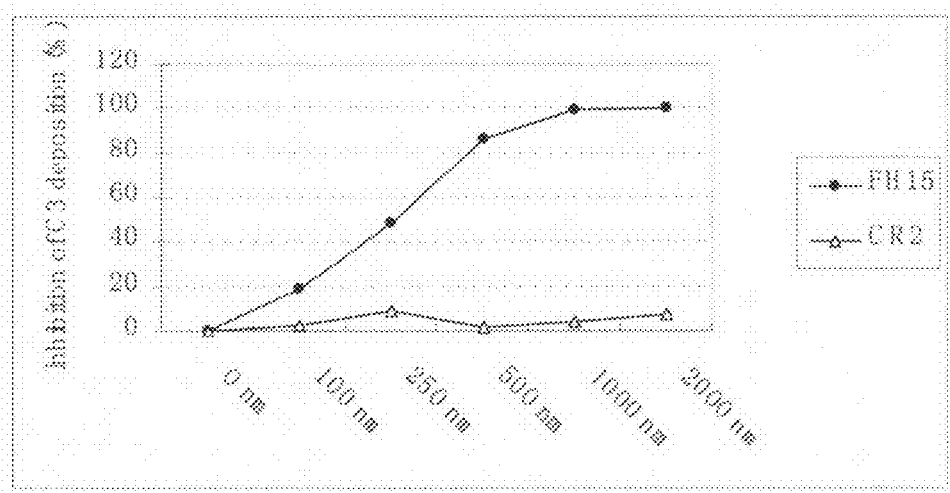

FIG. 12A provides a graphic representation of data obtained in an in vitro zymosan complement assay using a mouse CR2-FH fusion protein (CR2-H) and factor H alone (fH). FIG. 12B provides a graphic representation of data obtained in an in vitro zymosan complement assay using the first five SCR domains of FH (FH 15) and the first four domains of CR2 (CR2).

Figure 13:
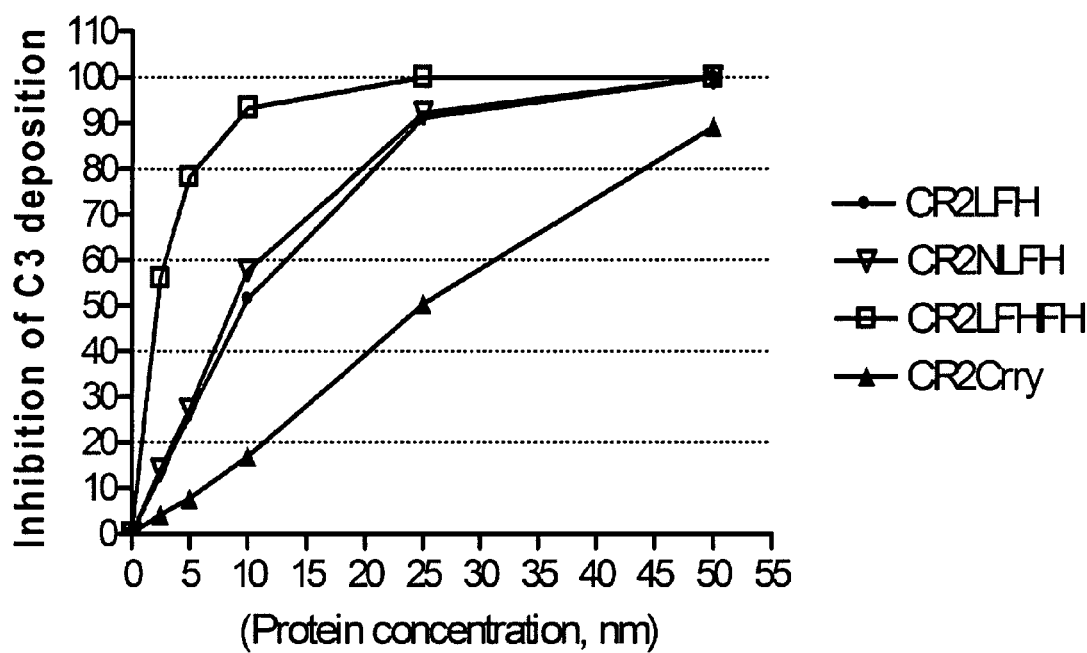

FIG. 13 provides a graphic representation of data obtained in an in vitro zymosan complement assay using mouse CR2-FH fusion protein with linker (CR2LFH), CR2-FH fusion protein without linker (CR2NLFH), CR2-FH-FH with linker (CR2LFHFH), and CR2-Crry.

Figure 14A:
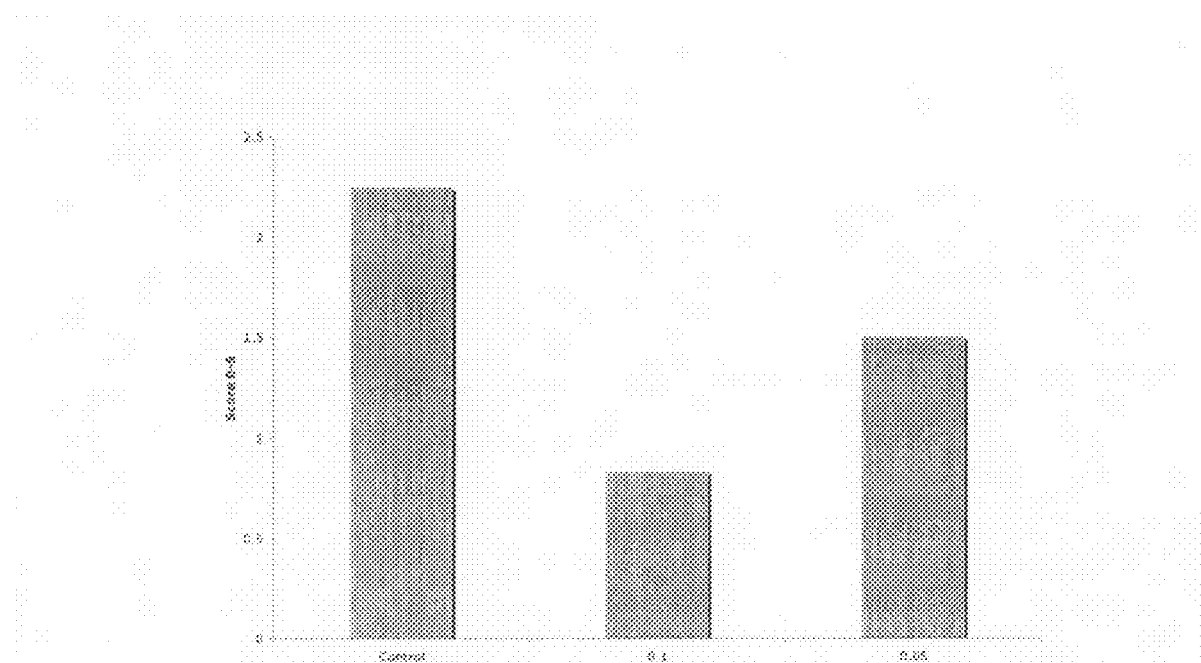
Figure 14B:
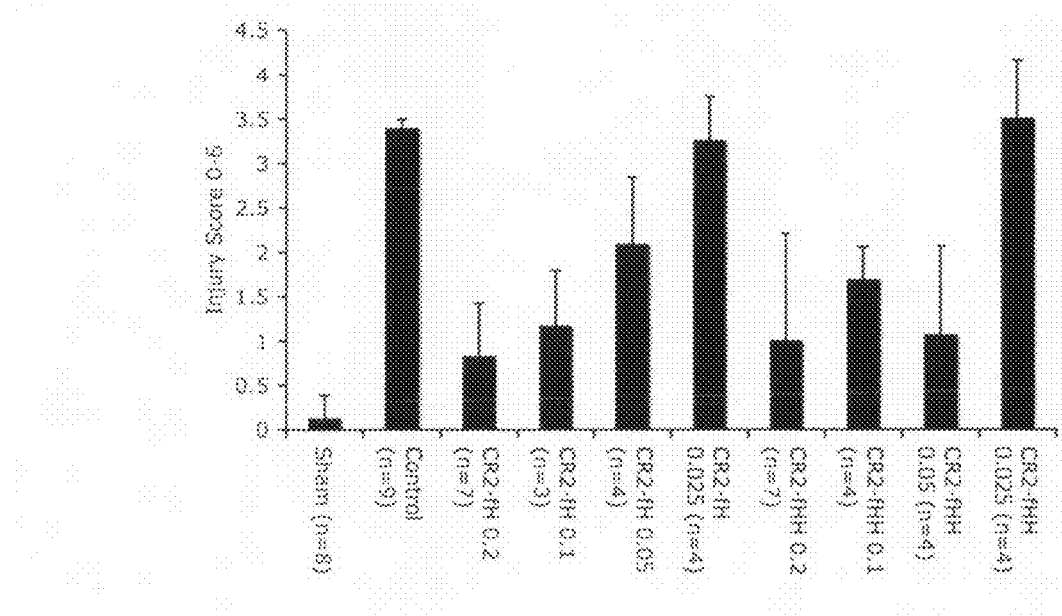

FIGS. 14A and 14B provide graphic representations of data obtained in an animal model of intestine ischemia and reperfusion injury using mouse CR2-FH fusion protein having one FH portion (CR2-fH) or two FH portions (CR2-fHH).

FIG. 15A provides a graphic representation of effects of CR2-fH on kidney function as measured by serum urea nitrogen (SUN). FIG. 15B provides a graphic representation of effects of CR2-fH on renal morphology. FIGS. 15C and 15D provide immunofluorescence staining results of control mouse (15C) and CR2-fH treated mouse (15D) kidney sections incubated with FTIC-conjugated antibody to mouse C3.

Figure 16:
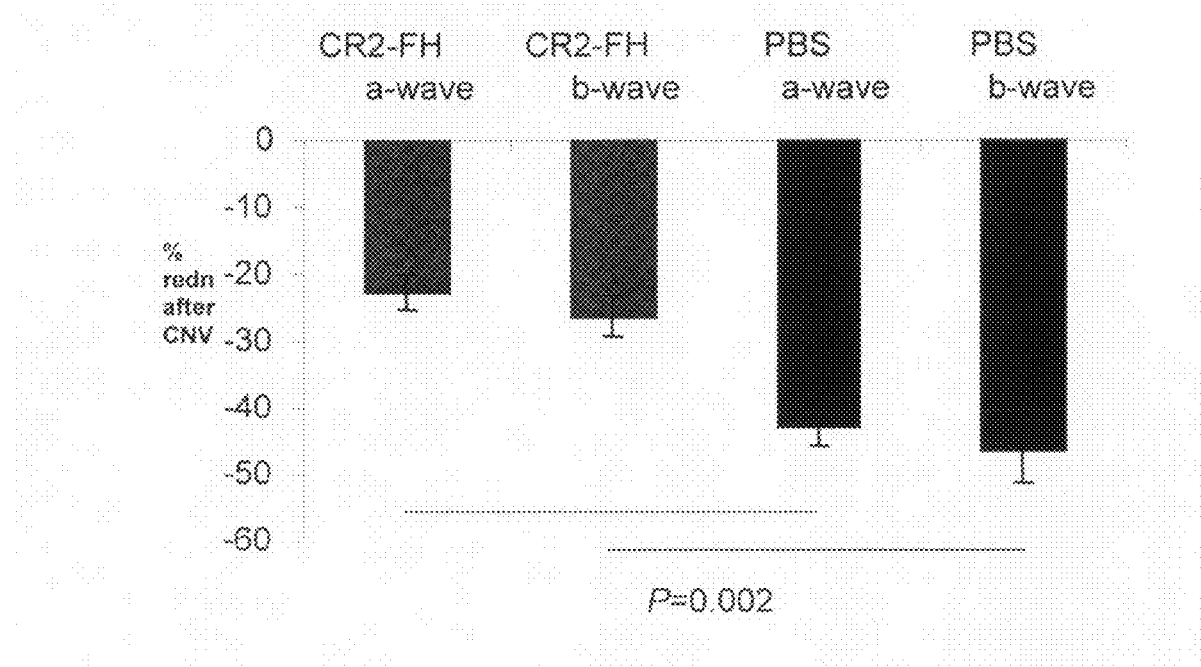

FIG. 16 provides a- and b-wave retinal response results in mice treated with or without CR2-fH.

Figures 17A, 17B:
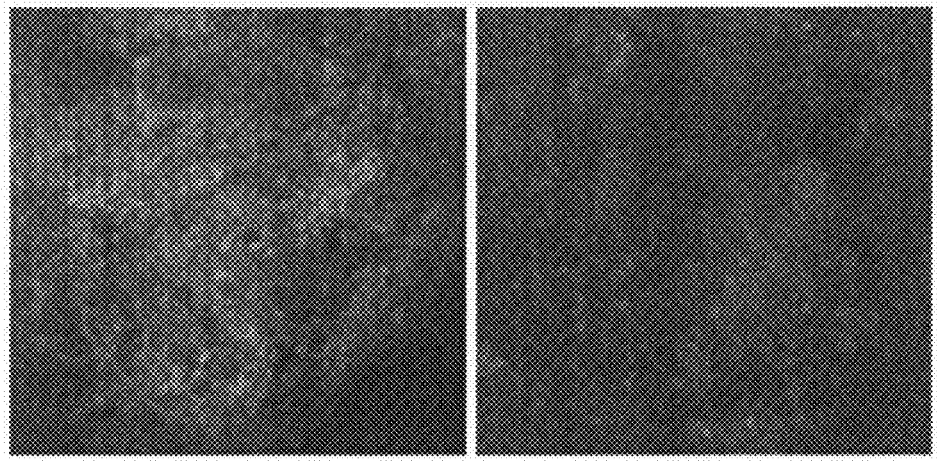
Figure 17C:
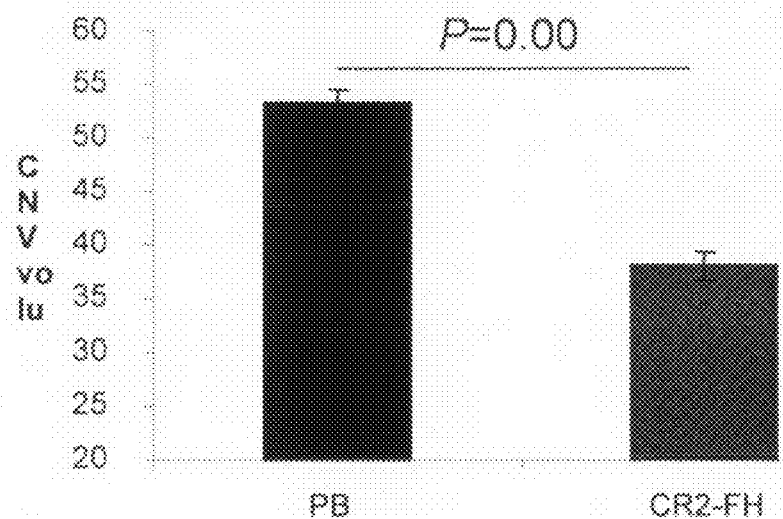

FIGS. 17A and 17B provides isolectin-b staining of lesions of mouse retina from control mouse (17A) and mouse treated with CR2-fH by intravenous injection (17B). FIG. 17C show quantification of lesion sizes based on the isolectin-b staining of FIGS. 17A and 17B.

Figures 18A, 18B:
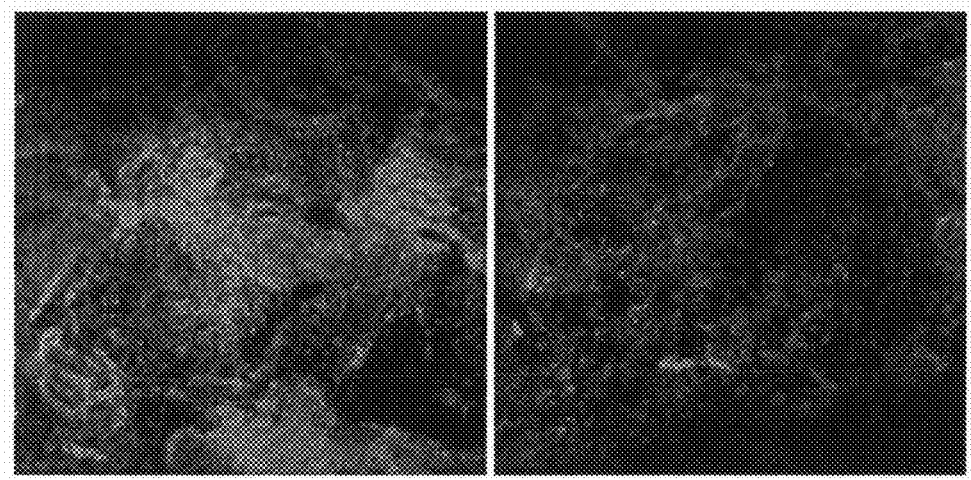
Figure 18C:
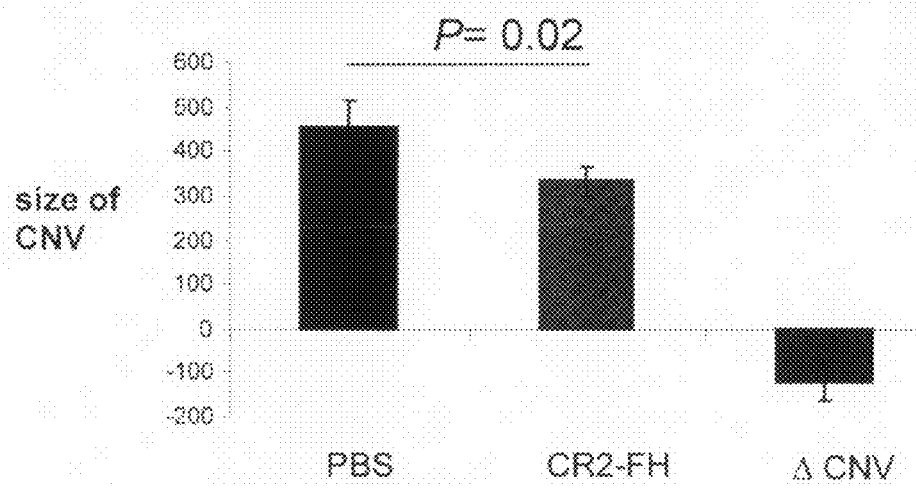

FIGS. 18A and 18B provides isolectin-b staining of lesions of mouse retina from control mouse (18A) and mouse treated with CR2-fH by intraoptical injection (18B). FIG. 18C provides quantification of lesion sizes based on the isolectin-b staining of FIGS. 18A and 18B.

FIG. 19 provides a survival curve of mouse heart transplant recipient treated with single dose of CR2-fH (CR2-fH), multiple doses of CR2-fH (CR2-fH (m)), and control buffer (PBS).

FIG. 20 provides amino acid sequence of an exemplary human CR2-FH fusion protein (designated as human CR2-fH or CR2fH) (SEQ ID NO:21) and an exemplary polynucleotide sequence that encodes a human CR2-fH plus the signal peptide (SEQ ID NO:22). Sequence encoding the signal peptide is underlined.

FIG. 21 provides an exemplary amino acid sequence of a human CR2-FH fusion protein containing two FH portions (designated as human CR2-FH2 or human CR2fH2) (SEQ ID NO:23) and an exemplary polynucleotide sequence that encodes a human CR2-FH2 plus the signal peptide (SEQ ID NO:24). Sequence encoding the signal peptide is underlined.

Figure 22A:
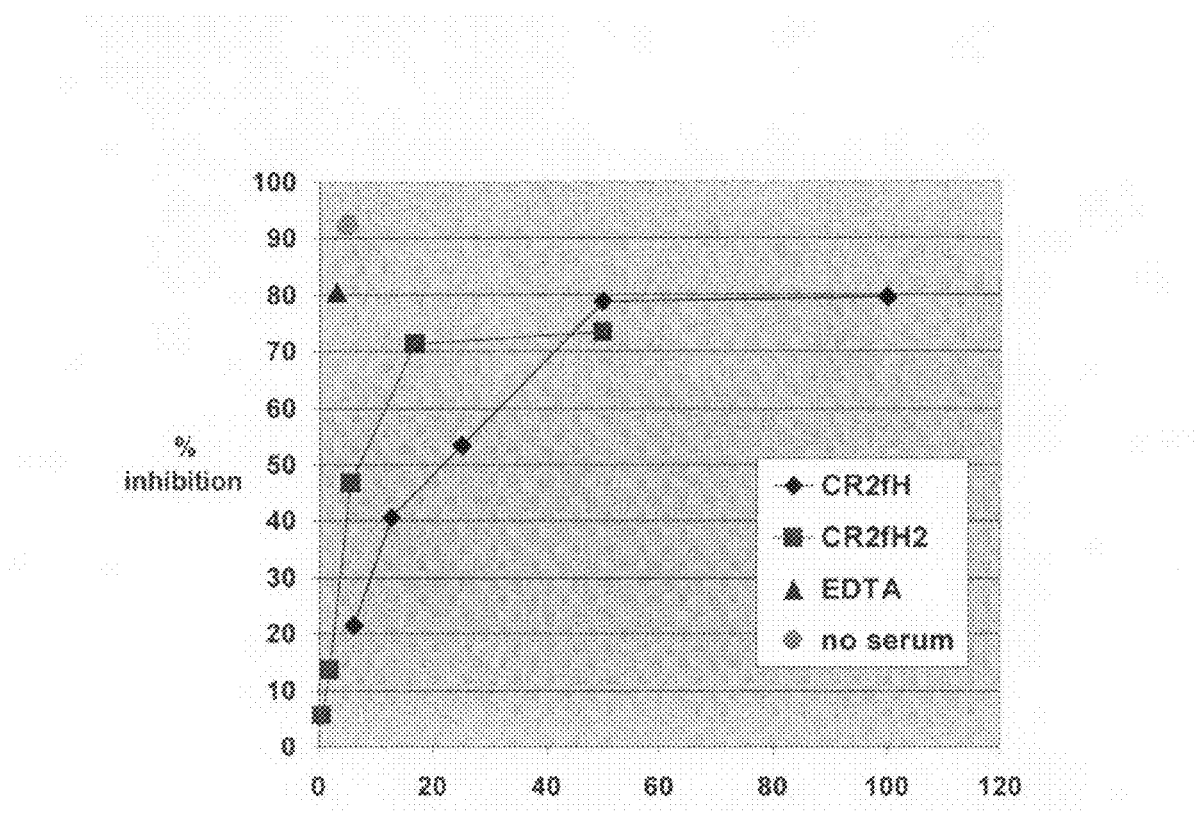
Figure 22B:
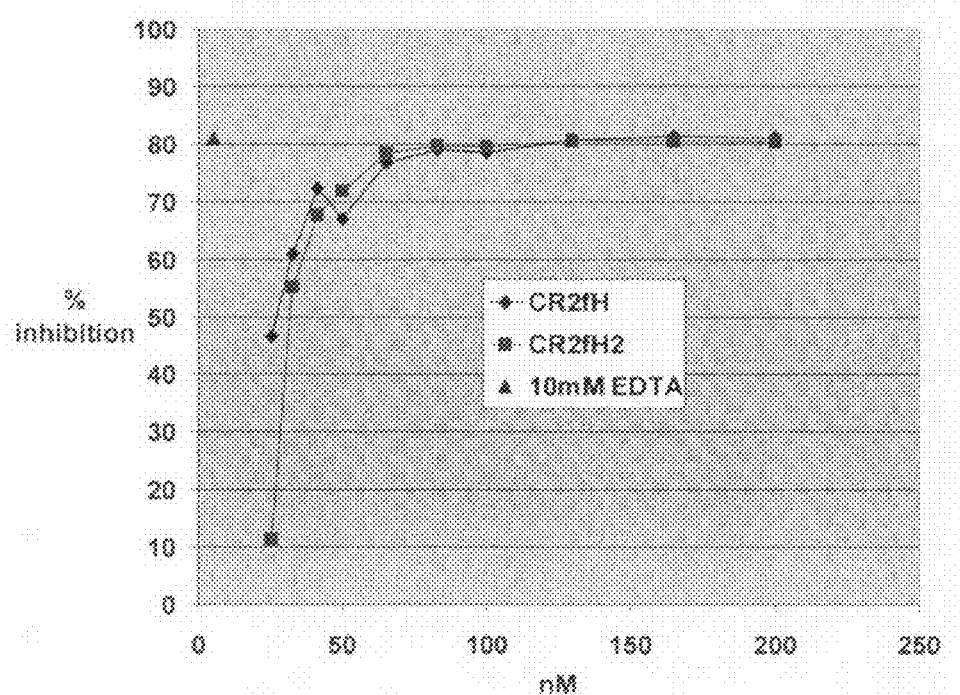

FIG. 22A shows inhibition of human CR2fH and CR2fH2 on alternative pathway specific C3b deposition onto zymosan particles. FIG. 22B shows inhibition of alternative pathway-mediated erythrocyte lysis by human CR2fH and human CR2fH2.

Figure 23:
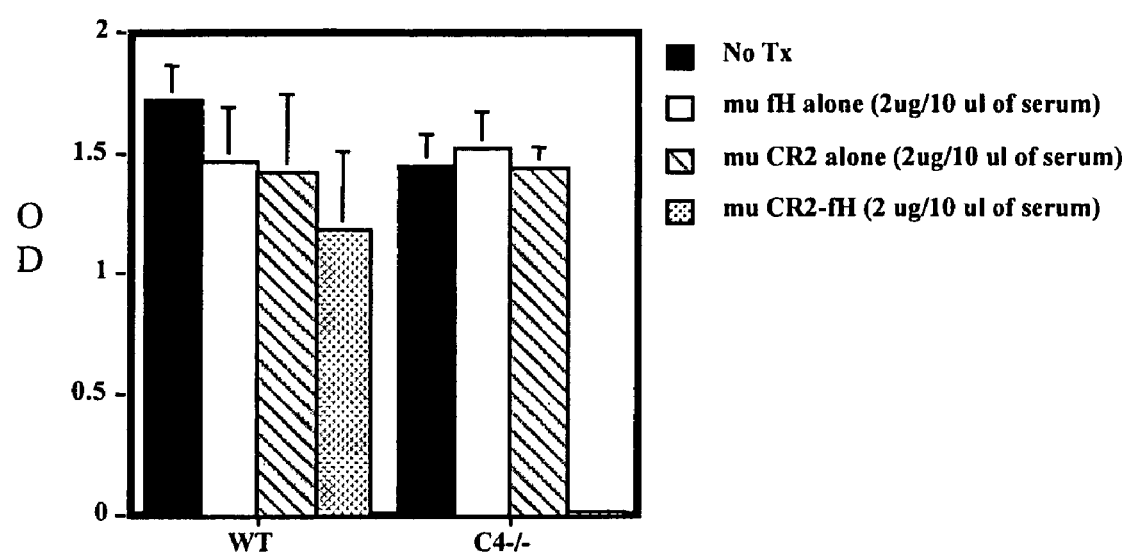

FIG. 23 shows the effects of mouse CR2-FH on C3 activation induced by immune-complexes of collagen-anti-collage antibodies. The Y-axis shows mean OD values.

Figure 24:
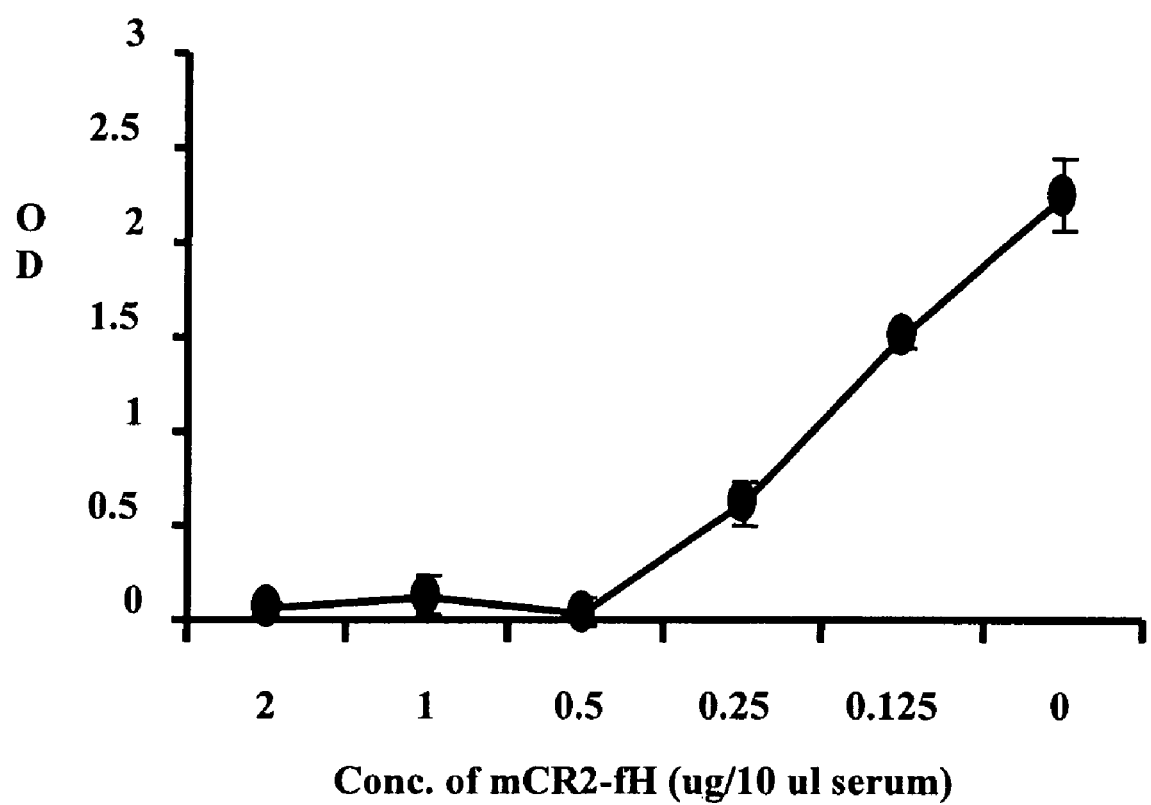

FIG. 24 shows titration of mouse CR2-FH in calcium sufficient buffer using serum from C4-/C4-knockout mouse. The Y-axis shows mean OD values.

DETAILED DESCRIPTION OF THE INVENTION

The present invention provides a CR2-FH molecule, compositions (such as pharmaceutical compositions) comprising a CR2-FH molecule, and methods of treating a disease in which the alternative complement pathway is implicated by administering the composition. The CR2-FH molecule comprises a CR2 portion and a FH portion. The CR2 portion is responsible for targeted delivery of the molecule to the sites of complement activation, and the FH portion is responsible for specifically inhibiting complement activation of the alternative pathway. Preliminary studies have shown that a CR2-FH molecule, specifically, a CR2-FH fusion protein containing the first four N-terminal SCR domains of the CR2 protein and the first five N-terminal SCR domains the factor H protein, has both targeting activity and complement inhibitory activity in vitro. This molecule is significantly more effective than a factor H molecule lacking the CR2 portion, suggesting that targeting FH to complement activation sites will be an effective therapeutic tool in treating disease in which the alternative complement pathway is implicated, such as macular degeneration (for example age-related macular degeneration). This observation is surprising because of the relatively high concentration of FH in the plasma and the long-held belief that cells which are in direct contact with plasma are already completely covered with FH. Jozsi et al., *Histopathol.* (2004) 19:251-258.

Accordingly, in one aspect, there is provided a CR2-FH molecule comprising: a) a CR2 portion comprising a CR2 or a fragment thereof, and b) a FH portion comprising a FH or a fragment thereof. In some embodiments, there is provided an isolated CR2-FH molecule. In some embodiments, there is provided a composition (such as a pharmaceutical composition) comprising a CR2-FH molecule. For example, in some embodiments, there is provided a pharmaceutical composition comprising a CR2-FH molecule and a pharmaceutically acceptable carrier suitable for administration to an individual systemically (such as intravenous injection), or locally (such as intraocular injection or injection into arteries including renal arteries).

In another aspect, there is provided a method of treating a disease in which the alternative complement pathway is implicated in an individual, comprising administering to the individual an effective amount of a composition comprising a CR2-FH molecule comprising: a) a CR2 portion comprising a CR2 or a fragment thereof, and b) a FH portion comprising a FH or a fragment thereof. Suitable diseases that can be treated by methods of the present invention include, for example, macular degeneration (such as age-related macular degeneration), rheumatoid arthritis, ischemia reperfusion, organ transplant rejection, and renal diseases such as MPGN II, HUS, and lupus nephritis.

Also provided are unit dosage forms, kits, and articles of manufacture that are useful for methods described herein.

General reference to "the composition" or "compositions" includes and is applicable to compositions of the invention.

As used herein, the singular form "a", "an", and "the" includes plural references unless indicated otherwise. For example, "a" FH portion includes one or more FH portions.

Reference to "about" a value or parameter herein includes (and describes) embodiments that are directed to that value or parameter per se. For example, description referring to "about X" includes description of "X".

It is understood that aspects and embodiments of the invention described herein include "consisting" and/or "consisting essentially of" aspects and embodiments.

CR2-FH Molecules and Compositions Comprising a CR2-FH Molecule

Provided herein are CR2-FH molecules and compositions (such as pharmaceutical compositions) comprising a CR2-FH molecule.

"CR2-FH molecule" used herein refers to a non-naturally occurring molecule comprising a CR2 or a fragment thereof (the "CR2 portion") and a FH or a fragment thereof (the "FH portion"). The CR2 portion is capable of binding to one or more natural ligands of CR2 and is thus responsible for targeted delivery of the molecule to the sites of complement activation. The FH portion is responsible for specifically inhibiting complement activation of the alternative complement pathway. The CR2 portion and the FH portion of the CR2-FH molecule can be linked together by any methods known in the art, as long as the desired functionalities of the two portions are maintained.

The CR2-FH molecule described herein thus generally has the dual functions of binding to a CR2 ligand and inhibiting complement activation of the alternative pathway. "CR2 ligand" refers to any molecule that binds to a naturally occurring CR2 protein, which include, but are not limited to, C3d, iC3b, C3dg, C3d, and cell-bound fragments of C3b that bind to the two N-terminal SCR domains of CR2. The CR2-FH molecule may, for example, bind to a CR2 ligand with a binding affinity that is about any of 10%, 20%, 30%, 40%, 50%, 60%, 70%, 80%, 90%, or 100% of the CR2 protein. Binding affinity can be determined by any method known in the art, including for example, surface plasmon resonance, calorimetry titration, ELISA, and flow cytometry. In some embodiments, the CR2-FH molecule has one or more of the following properties of CR2: (1) binding to C3d, (2) binding to iC3b, (3) binding to C3dg, (4) binding to C3d, and (5) binding to cell-bound fragment(s) of C3b that bind to the two N-terminal SCR domains of CR2.

The CR2-FH molecule described herein is generally capable of inhibiting complement activation of the alternative pathway. The CR2-FH molecule may be a more potent complement inhibitor than the naturally occurring FH protein. For example, in some embodiments, the CR2-FH molecule has a complement inhibitory activity that is about any of 1.5, 2, 2.5, 3, 3.5, 4, 5, 6, 7, 8, 9, 10, 12, 14, 16, 18, 20, 25, 30, 40, or more fold of that of the FH protein. In some embodiments, the CR2-FH molecule has an EC50 of less than about any of 100 nM, 90 nM, 80 nM, 70 nM, 60 nM, 50 nM, 40 nM, 30 nM, 20 nM, or 10 nM. In some embodiments, the CR2-FH molecule has an EC50 of about 5-60 nM, including for example any of 8-50 nM, 8-20 nM, 10-40 nM, and 20-30 nM. In some embodiments, the CR2-FH molecule has complement inhibitory activity that is about any of 50%, 60%, 70%, 80%, 90%, or 100% of that of the FH protein.

Complement inhibition can be evaluated based on any methods known in the art, including for example, in vitro zymosan assays, assays for lysis of erythrocytes, immune complex activation assays, and mannan activation assays. In some embodiments, the CR2-FH has one or more of the following properties of FH: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

In some embodiments, the CR2-FH molecule is a fusion protein. "Fusion protein" used herein refers to two or more peptides, polypeptides, or proteins operably linked to each other. In some embodiments, the CR2 portion and the FH portion are directly fused to each other. In some embodiments, the CR2 portion and the FH portion are linked by an amino acid linker sequence. Examples of linker sequences are known in the art, and include, for example, (Gly$_4$Ser), (Gly$_4$Ser)$_2$, (Gly$_4$Ser)$_3$, (Gly$_3$Ser)$_4$, (SerGly$_4$), (SerGly$_4$)$_2$, (SerGly$_4$)$_3$, and (SerGly$_4$)$_4$. Linking sequences can also comprise "natural" linking sequences found between different domains of complement factors. For example, VSVFPLE, the linking sequence between the first two N-terminal short consensus repeat domains of human CR2, can be used. In some embodiments, the linking sequence between the fourth and the fifth N-terminal short consensus repeat domains of human CR2 (EEIF) is used. The order of CR2 portion and FH portion in the fusion protein can vary. For example, in some embodiments, the C-terminus of the CR2 portion is fused (directly or indirectly) to the N-terminus of the FH portion of the molecule. In some embodiments, the N-terminus of the CR2 portion is fused (directly or indirectly) to the C-terminus of the FH portion of the molecule.

In some embodiments, the CR2-FH molecule is a CR2-FH fusion protein having an amino acid sequence of any of SEQ ID NO:3, SEQ ID NO:21, and SEQ ID NO:23. In some embodiments, the CR2-FH molecule is a fusion protein having an amino acid sequence that is at least about 50%, 60%, 70%, 80%, 90%, 91%, 92%, 93%, 94%, 95%, 96%, 97%, 98%, or 99% identical to that of any of SEQ ID NO:3, SEQ ID NO:21, or SEQ ID NO:23. In some embodiments, the CR2-FH molecule comprises at least about 400, 450, 500, 550, or more contiguous amino acids of any of SEQ ID NO:3, SEQ ID NO:21, and SEQ ID NO:23.

In some embodiments, the CR2-FH molecule is a CR2-FH fusion protein having an amino acid sequence of any of SEQ ID NOs:5-10. In some embodiments, the CR2-FH molecule is a fusion protein having an amino acid sequence that is at least about 50%, 60%, 70%, 80%, 90%, 91%, 92%, 93%, 94%, 95%, 96%, 97%, 98%, or 99% identical to that of any of SEQ ID NOs:5-10. In some embodiments, the CR2-FH molecule comprises at least about 400, 450, 500, 550, or more contiguous amino acids any of SEQ ID NOs:5-10.

In some embodiments, the CR2-FH molecule is encoded by a polynucleotide having nucleic acid sequence of any of SEQ ID NO:4, SEQ ID NO:22, and SEQ ID NO:24. In some embodiments, the CR2-FH molecule is encoded by a polynucleotide having a nucleic acid sequence that is at least about 50%, 60%, 70%, 80%, 90%, 91%, 92%, 93%, 94%, 95%, 96%, 97%, 98%, or 99% identical to that of any of SEQ ID NO:4, SEQ ID NO:22, and SEQ ID NO:24.

In some embodiments, the CR2-FH molecule comprises a CR2 portion and a FH portion linked via a chemical crosslinker. Linking of the two portions can occur on reactive groups located on the two portions. Reactive groups that can be targeted using a crosslinker include primary amines, sulfhydryls, carbonyls, carbohydrates, and carboxylic acids, or active groups that can be added to proteins. Examples of chemical linkers are well known in the art and include, but are not limited to, bismaleimidohexane, maleimidobenzoyl-N-hydroxysuccinimide ester, NHS-Esters-Maleimide Crosslinkers such as SPDP, carbodiimide, glutaraldehyde, MBS, Sulfo-MBS, SMPB, sulfo-SMPB, GMBS, Sulfo-GMBS, EMCS, Sulfo-EMCS, imidoester crosslinkers such as DMA, DMP, DMS, DTBP, EDC and DTME.

In some embodiments, the CR2 portion and the FH portion are non-covalently linked. For example, the two portions may be brought together by two interacting bridging proteins (such as biotin and streptavidin), each linked to a CR2 portion or a FH portion.

In some embodiments, the CR2-FH molecule comprises two or more (same or different) CR2 portions described herein. In some embodiments, the CR2-FH molecule comprises two or more (same or different) FH portions described herein. These two or more CR2 (or FH) portions may be tandemly linked (such as fused) to each other. In some embodiments, the CR2-FH molecule (such a CR2-FH fusion protein) comprises a CR2 portion and two or more (such as three, four, five, or more) FH portions. In some embodiments, the CR2-FH molecule (such a CR2-FH fusion protein) comprises a FH portion and two or more (such as three, four, five, or more) CR2 portions. In some embodiments, the CR2-FH molecule (such a CR2-FH fusion protein) comprises two or more CR2 portions and two or more FH portions.

In some embodiments, there is provided an isolated CR2-FH molecule. In some embodiments, the CR2-FH molecules form dimers or multimers.

The CR2 portion and the FH portion in the molecule can be from the same species (such as human or mouse), or from different species. CR2 portion The CR2 portion described herein comprises a CR2 or a fragment thereof. CR2 is a transmembrane protein expressed predominantly on mature B cells and follicular dendritic cells. CR2 is a member of the C3 binding protein family. Natural ligands for CR2 include, for example, iC3b, C3dg, and C3d, and cell-bound breakdown fragments of C3b that bind to the two N-terminal SCR domains of CR2. Cleavage of C3 results initially in the generation of C3b and the covalent attachment of this C3b to the activating cell surface. The C3b fragment is involved in the generation of enzymatic complexes that amplify the complement cascade. On a cell surface, C3b is rapidly converted to inactive iC3b, particularly when deposited on a host surface containing regulators of complement activation (i.e., most host tissue). Even in absence of membrane bound complement regulators, substantial levels of iC3b are formed. iC3b is subsequently digested to the membrane bound fragments C3dg and then C3d by serum proteases, but this process is relatively slow. Thus, the C3 ligands for CR2 are relatively long lived once they are generated and will be present in high concentrations at sites of complement activation. CR2 therefore can serve as a potent targeting vehicle for bringing molecules to the site of complement activation.

CR2 contains an extracellular portion having 15 or 16 repeating units known as short consensus repeats (SCR domains). The SCR domains have a typical framework of highly conserved residues including four cysteines, two prolines, one tryptophane and several other partially conserved glycines and hydrophobic residues. SEQ ID NO:1 represents the full-length human CR2 protein sequence. Amino acids 1-20 comprise the leader peptide, amino acids 23-82 comprise SCR1, amino acids 91-146 comprise SCR2, amino acids 154-210 comprise SCR3, amino acids 215-271 comprise SCR4. The active site (C3d binding site) is located in SCR1-2 (the first two N-terminal SCR domains). These SCR domains are separated by short sequences of variable length that serve as spacers. The full-length mouse CR2 protein sequence is represented herein by SEQ ID NO:15. The SCR1 and SCR2 domains of the mouse CR2 protein are located with the mouse CR2 amino sequence at positions 14-73 of SEQ ID NO:15 (SCR1) and positions 82-138 of SEQ ID NO:15 (SCR2). Human and mouse CR2 are approximately 66% identical over the full length amino acid sequences represented by SEQ ID NO:1 and SEQ ID NO:15, and approximately 61% identical over the SCR1-SCR2 regions of SEQ ID NO:1 and SEQ ID NO:15. Both mouse and human CR2 bind to C3 (in the C3d region). It is understood that species and strain variations exist for the disclosed peptides, polypeptides, and proteins, and that the CR2 or a fragment thereof described herein encompasses all species and strain variations.

The CR2 portion disclosed herein refers to a polypeptide that contains some or all of the ligand binding sites of the CR2 protein, and includes, but is not limited to, full-length CR2 proteins (such as human CR2 as shown in SEQ ID NO:1 or mouse CR2 as shown in SEQ ID NO:15), soluble CR2 proteins (such as a CR2 fragment comprising the extracellular domain of CR2), other biologically active fragments of CR2, a CR2 fragment comprising SCR1 and SCR2, or any homologue of a naturally occurring CR2 or fragment thereof, as described in detail below. In some embodiments, the CR2 portion has one of the following properties or CR2: (1) binding to C3d, (2) binding to iC3b, (3) binding to C3dg, (4) binding to C3d, and (5) binding to cell-bound fragment(s) of C3b that bind to the two N-terminal SCR domains of CR2.

In some embodiments, the CR2 portion comprises the first two N-terminal SCR domains of CR2. In some embodiments, the CR2 portion comprises the first three N-terminal SCR domains of CR2. In some embodiments, the CR2 portion comprises the first four N-terminal SCR domains of CR2. In some embodiments, the CR2 portion comprises (and in some embodiments consists of or consists essentially of) at least the first two N-terminal SCR domains of CR2, including for example at least any of the first 3, 4, 5, 6, 7, 8, 9, 10, 11, 12, 13, 14, 15, or 16 SCR domains of CR2.

A homologue of a CR2 protein or a fragment thereof includes proteins which differ from a naturally occurring CR2 (or CR2 fragment) in that at least one or a few amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). In some embodiments, a CR2 homologue has an amino acid sequence that is at least about 70% identical to the amino acid sequence of a naturally occurring CR2 (e.g., SEQ ID NO:1, or SEQ ID NO:15), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring CR2 (e.g., SEQ ID NO:1, or SEQ ID NO:15). A CR2 homologue or a fragment thereof preferably retains the ability to bind to a naturally occurring ligand of CR2 (e.g., C3d or other C3 fragments with CR2-binding ability). For example, the CR2 homologue (or fragment thereof) may have a binding affinity for C3d that is at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of that of CR2 (or a fragment thereof).

In some embodiments, the CR2 portion comprises at least the first two N-terminal SCR domains of a human CR2, such as a CR2 portion having an amino acid sequence containing at least amino acids 23 through 146 of the human CR2 (SEQ ID NO:1). In some embodiments, the CR2 portion comprises at least the first two SCR domains of human CR2 having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 23 through 146 of the human CR2 (SEQ ID NO:1).

In some embodiments, the CR2 portion comprises at least the first four N-terminal SCR domains of a human CR2, such as a CR2 portion having an amino acid sequence containing at least amino acids 23 through 271 of the human CR2 (SEQ ID NO:1). In some embodiments, the CR2 portion comprises at least the first four SCR domains of human CR2 having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 23 through 271 of the human CR2 (SEQ ID NO:1).

An amino acid sequence that is at least about, for example, 95% identical to a reference sequence (such as SEQ ID NO:1) is intended that the amino acid sequence is identical to the reference sequence except that the amino acid sequence may include up to five point alterations per each 100 amino acids of the reference sequence. These up to five point alterations may be deletions, substitutions, additions, and may occur anywhere in the sequence, interspersed either individually among amino acids in the reference sequence or in one or more continuous groups within the reference sequence.

In some embodiments, the CR2 portion comprises part or all of the ligand binding sites of the CR2 protein. In some embodiments, the CR2 portion further comprises sequences required to maintain the three dimensional structure of the binding site. Ligand binding sites of CR2 can be readily determined based on the crystal structures of CR2, such as the human and mouse CR2 crystal structures disclosed in U.S. Patent Application Publication No. 2004/0005538. For example, in some embodiments, the CR2 portion comprises the B strand and B-C loop of SCR2 of CR2. In some embodiments, the CR2 portion comprises a site on strand B and the B-C loop of CR2 SCR comprising the segment G98-G99-Y100-K101-I102-R103-G104-S105-T106-P107-Y108 with respect to SEQ ID NO:1. In some embodiments, the CR2 portion comprises a site on the B strand of CR2 SCR2 comprising position K119 with respect to SEQ ID NO:1. In some embodiments, the CR2 portion comprises a segment comprising V149-F150-P151-L152, with respect to SEQ ID NO:1. In some embodiments, the CR2 portion comprises a segment of CR2 SCR2 comprising T120-N121-F122. In some embodiments, the CR2-FH molecule has two or more of these sites. For example, in some embodiments, the CR2 portion comprises a portion comprising G98-G99-Y100-K101-I102-R103-G104-S105-T106-P107-Y108 and K119 with respect to SEQ ID NO:1. Other combinations of these sites are also contemplated.

Factor H Portion

The FH portion of the CR2-FH molecule described herein comprises a FH or a fragment thereof.

Complement factor H (FH) is a single polypeptide chain plasma glycoprotein. The protein is composed of 20 repetitive SCR domains of approximately 60 amino acids, arranged in a continuous fashion like a string of 20 beads. Factor H binds to C3b, accelerates the decay of the alternative pathway C3-convertase (C3Bb), and acts as a cofactor for the proteolytic inactivation of C3b. In the presence of factor H, C3b proteolysis results in the cleavage of C3b. Factor H has at least three distinct binding domains for C3b, which are located within SCR 1-4, SCR 5-8, and SCR 19-20. Each site of factor H binds to a distinct region within the C3b protein: the N-terminal sites bind to native C3b; the second site, located in the middle region of factor H, binds to the C3c fragment and the sited located within SCR19 and 20 binds to the C3d region. In addition, factor H also contains binding sites for heparin, which are located within SCR 7, SCR 5-12, and SCR20 of factor H and overlap with that of the C3b binding site. Structural and functional analyses have shown that the domains for the complement inhibitory activity of FH are located within the first four N-terminal SCR domains.

SEQ ID NO:2 represents the full-length human FH protein sequence. Amino acids 1-18 correspond to the leader peptide, amino acids 21-80 correspond to SCR1, amino acids 85-141 correspond to SCR2, amino acids 146-205 correspond to SCR3, amino acids 210-262 correspond to SCR4, amino acids 267-320 correspond to SCR5. The full-length mouse FH protein sequence is represented herein by SEQ ID NO:16. The SCR1 and SCR2 domains of the mouse FH protein are located with the mouse FH amino sequence at positions 21-27 of SEQ ID NO:16 (SCR1) and positions 82-138 of SEQ ID NO:16 (SCR2). Human and mouse FH are approximately 61% identical over the full length amino acid sequences represented by SEQ ID NO:2 and SEQ ID NO:16. It is understood that species and strain variations exist for the disclosed peptides, polypeptides, and proteins, and that the FH or a fragment thereof encompasses all species and strain variations.

The FH portion described herein refers to any portion of a FH protein having some or all the complement inhibitory activity of the FH protein, and includes, but is not limited to, full-length FH proteins, biologically active fragments of FH proteins, a FH fragment comprising SCR1-4, or any homologue of a naturally occurring FH or fragment thereof, as described in detail below. In some embodiments, the FH portion has one or more of the following properties: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

In some embodiments, the FH portion comprises the first four N-terminal SCR domains of FH. In some embodiments, the construct comprises the first five N-terminal SCR domains of FH. In some embodiments, the construct comprises the first six N-terminal SCR domains of FH. In some embodiments, the FH portion comprises (and in some embodiments consists of or consisting essentially of) at least the first four N-terminal SCR domains of FH, including for example, at least any of the first 5, 6, 7, 8, 9, 10, 11, 12, 13, 14, or more N-terminal SCR domains of FH.

In some embodiments, the FH is a wildtype FH. In some embodiments, the FH is a protective variant of FH.

In some embodiments, the FH portion lacks a heparin binding site. This can be achieved, for example, by mutation of the heparin binding site on FH, or by selecting FH fragments that do not contain a heparin binding site. In some embodiments, the FH portion comprises a FH or a fragment thereof having a polymorphism that is protective to age-related macular degeneration. Hageman et al., *Proc. Natl. Acad. Sci. USA* 102(20):7227. One example of a CR2-FH molecule comprising such a sequence is provided in FIG. 4 (SEQ ID NO:6).

A homologue of a FH protein or a fragment thereof includes proteins which differ from a naturally occurring FH (or FH fragment) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). For example, a FH homologue may have an amino acid sequence that is at least about 70% identical to the amino acid sequence of a naturally occurring FH (e.g., SEQ ID NO:2, or SEQ ID NO:16), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring FH (e.g., SEQ ID NO:2, or SEQ ID NO:16). In some embodiment, a homologue of FH (or a fragment thereof) retains all the complement inhibition activity of FH (or a fragment thereof). In some embodiments, the homologue of FH (or a fragment thereof) retains at least about 50%, for example, at least about any of 60%, 70%, 80%, 90%, or 95% of the complement inhibition activity of FH (or a fragment thereof).

In some embodiments, the FH portion comprises at least the first four N-terminal SCR domains of a human FH, such as a FH portion having an amino acid sequence containing at least amino acids 21 through 262 of the human FH (SEQ ID NO:2). In some embodiments, the FH portion comprises at least the first four N-terminal SCR domains of human FH having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 21 through 262 of the human FH (SEQ ID NO:2).

In some embodiments, the FH portion comprises at least the first five N-terminal SCR domains of a human FH, such as a FH portion having an amino acid sequence containing at least amino acids 21 through 320 of the human FH (SEQ ID NO:2). In some embodiments, the FH portion comprises at least the first five N-terminal SCR domains of human FH having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 21 through 320 of the human FH (SEQ ID NO:2).

In some embodiments, the FH portion comprises a full length or a fragment of factor-H like 1 molecule (FHL-1), a protein encoded by an alternatively spliced transcript of the factor H gene. The mature FHL-1 contains 431 amino acids. The first 427 amino acids organize seven SCR domains and are identical to the N-terminal SCR domains of FH. The remaining four amino acid residues Ser-Phe-Thr-Leu (SFTL) at the C-terminus are specific to FHL-1. FHL-1 has been characterized functionally and shown to have factor H complement regulatory activity. The term "FH portion" also encompasses full length or fragments of factor H related molecules, including, but are not limited to, proteins encoded by the FHR1, FHR2, FHR3, FHR4, FHR5 genes. These factor H related proteins are disclosed, for example, in de Cordoba et al., *Molecular Immunology* 2004, 41:355-367.

Variants of CR2-FH Molecules

Also encompassed are variants of the CR2-FH molecules (such as the CR2-FH fusion proteins). A variant of the CR2-FH molecule described herein may be: (i) one in which one or more of the amino acid residues of the CR2 portion and/or the FH portion are substituted with a conserved or non-conserved amino acid residue (preferably a conserved amino acid residue) and such substituted amino acid residue may or may not be one encoded by the genetic code; or (ii) one in which one or more of the amino acid residues in the CR2 portion and/or FH portion includes a substituent group, or (iii) one in which the CR2-FH molecule (such as the CR2-FH fusion protein) is fused with another compound, such as a compound to increase the half-life of the CR2-FH molecule (for example, polyethylene glycol), or (iv) one in which additional amino acids are fused to the CR2-FH molecule (such as the CR2-FH fusion protein), such as a leader or secretory sequence or a sequence which is employed for purification of the CR2-FH molecule (such as the CR2-FH fusion protein), or (v) one in which the CR2-FH molecule (such as the CR2-FH fusion protein) is fused with a larger polypeptide, i.e., human albumin, an antibody or Fc, for increased duration of effect. Such variants are deemed to be within the scope of those skilled in the art from the teachings herein.

In some embodiments, the variant of the CR2-FH molecule contains conservative amino acid substitutions (defined further below) made at one or more predicted, preferably nonessential amino acid residues. A "nonessential" amino acid residue is a residue that can be altered from the wild-type sequence of a protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Amino acid substitutions in the CR2 or FH portions of the CR2-FH molecule can be introduced to improve the functionality of the molecule. For example, amino acid substitutions can be introduced into the CR2 portion of the molecule to increase binding affinity of the CR2 portion to its ligand(s), increase binding specificity of the CR2 portion to its ligand(s), improve targeting of the CR2-FH molecule to desired sites, increase dimerization or multimerization of CR2-FH molecules, and improve pharmacokinetics of the CR2-FH molecule. Similarly, amino acid substitutions can be introduced into the FH portion of the molecule to increase the functionality of the CR2-FH molecule and improve pharmacokinetics of the CR2-FH molecule.

In some embodiments, the CR2-FH molecule (such as the CR2-FH fusion protein) is fused with another compound, such as a compound to increase the half-life of the polypeptide and/or to reduce potential immunogenicity of the polypeptide (for example, polyethylene glycol, "PEG"). The PEG can be used to impart water solubility, size, slow rate of kidney clearance, and reduced immunogenicity to the fusion protein. See e.g., U.S. Pat. No. 6,214,966. In the case of PEGylations, the fusion of the CR2-FH molecule (such as the CR2-FH fusion protein) to PEG can be accomplished by any means known to one skilled in the art. For example, PEGylation can be accomplished by first introducing a cysteine mutation into the CR2-FH fusion protein, followed by site-specific derivatization with PEG-maleimide. The cysteine can be added to the C-terminus of the CR2-FH fusion protein. See, e.g., Tsutsumi et al. (2000) *Proc. Natl. Acad. Sci. USA* 97(15):8548-8553. Another modification which can be made to the CR2-FH molecule (such as the CR2-FH fusion protein) involves biotinylation. In certain instances, it may be useful to have the CR2-FH molecule (such as the CR2-FH fusion protein) biotinylated so that it can readily react with streptavidin. Methods for biotinylation of proteins are well known in the art. Additionally, chondroitin sulfate can be linked with the CR2-FH molecule (such as the CR2-FH fusion protein).

In some embodiments, the CR2-FH molecule is fused to another targeting molecule or targeting moiety which further increases the targeting efficiency of the CR2-FH molecule. For example, the CR2-FH molecule can be fused to a ligand (such as an amino acid sequence) that has the capability to bind or otherwise attach to an endothelial cell of a blood vessel (referred to as "vascular endothelial targeting amino acid ligand"). Exemplary vascular endothelial targeting ligands include, but are not limited to, VEGF, FGF, integrin, fibronectin, I-CAM, PDGF, or an antibody to a molecule expressed on the surface of a vascular endothelial cell.

In some embodiments, the CR2-FH molecule is conjugated (such as fused) to a ligand for intercellular adhesion molecules. For example, the CR2-FH molecule can be conjugated to one or more carbohydrate moieties that bind to an intercellular adhesion molecule. The carbohydrate moiety facilitates localization of the CR2-FH molecule to the site of injury. The carbohydrate moiety can be attached to the CR2-FH molecule by means of an extracellular event such as a chemical or enzymatic attachment, or can be the result of an intracellular processing event achieved by the expression of appropriate enzymes. In some embodiments, the carbohydrate moiety binds to a particular class of adhesion molecules such as integrins or selectins, including E-selectin, L-selectin or P-selectin. In some embodiments, the carbohydrate moiety comprises an N-linked carbohydrate, for example the complex type, including fucosylated and sialylated carbohydrates. In some embodiments, the carbohydrate moiety is related to the Lewis X antigen, for example the sialylated Lewis X antigen.

For treatment of eye diseases such as AMD, the CR2-FH can be conjugated (such as fused) to an antibody that recognizes a neoepitope of the drusen. Other targeting molecules such as small targeting peptide can also be used. Other modifications of the CR2-FH molecule include, for example, glycosylation, acetylation, phosphorylation, amidation, derivatization by known protecting/blocking groups, and the like.

The CR2-FH molecule may include the addition of an immunologically active domain, such as an antibody epitope or other tag, to facilitate targeting or purification of the polypeptide. The use of 6× His and GST (glutathione S transferase) as tags is well known. Inclusion of a cleavage site at or near the fusion junction will facilitate removal of the extraneous polypeptide after purification. Other amino acid sequences that may be included in the CR2-FH molecule include functional domains, such as active sites from enzymes such as a hydrolase, glycosylation domains, and cellular targeting signals.

Variants of the CR2-FH molecule (such as the CR2-FH fusion protein) include polypeptides having an amino acid sequence sufficiently similar to the amino acid sequence of the CR2-FH molecule. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that contain a common structural domain that is at least about 45%, preferably about 75% through 98%, identical are defined herein as sufficiently similar. Variants include variants of fusion proteins encoded by a polynucleotide that hybridizes to a polynucleotide of this invention or a complement thereof under stringent conditions. Such variants generally retain the functional activity of the fusion proteins of this invention. Libraries of fragments of the polynucleotides can be used to generate a variegated population of fragments for screening and subsequent selection. For example, a library of fragments can be generated by treating a double-stranded PCR fragment of a polynucleotide with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the fusion proteins of this invention.

Variants include fusion proteins that differ in amino acid sequence due to mutagenesis. In addition, bioequivalent analogs of the CR2-FH molecule (such as fusion protein) may also be constructed by making various substitutions on residues or sequences in the CR2 portion and/or the FH portion.

In some embodiments, the CR2-FH molecule, particularly the CR2-FH fusion protein, is fused at its N-terminus a signal peptide. Such signal peptides are useful for the secretion of the CR2-FH molecule. Suitable signal peptides include, for example, the signal peptide of the CD5 protein (such as signal peptide of the human CD5 protein MPMGSLQPLATLYLLGMLVAS, SEQ ID NO:11). In some embodiments, the signal peptide of the CR2 protein is used. For example, in some embodiments, the signal peptide of the human CR2 protein (MGAAGLLGVFLALVAPG, SEQ ID NO:13 or MGAAGLLGVFLALVAPGVLG, SEQ ID NO:25) is used.

Preparation of CR2-FH Molecules

The CR2-FH molecules (or the two portions of the CR2-FH molecules) described herein may be made by chemical synthesis methods, or by linkage of a polynucleotide encoding the CR2 portion and a polynucleotide encoding the FH portion (with or without a linker sequence), and introducing the resulting polynucleotide molecule in a vector for transfecting host cells that are capable of expressing the molecule. Chemical synthesis, especially solid phase synthesis, is preferred for short peptides or those containing unnatural or unusual amino acids such as D-Tyr, Ornithine, and the like. Recombinant procedures are preferred for longer polypeptides. The CR2-FH molecule can be isolated in vitro by protein purification methods. The CR2-FH molecule can also be provided "in situ" by introduction of a gene therapy system to the tissue of interest which then expresses the CR2-FH fusion.

Recombinant DNA techniques for making a CR2-FH fusion protein involves, in simplified form, taking the a CR2-FH encoding polynucleotide, inserting it into an appropriate vector, inserting the vector into an appropriate host cell, and recovering or isolating the fusion protein produced thereby.

Provided herein are polynucleotides that encode a CR2-FH molecule (i.e., a CR2-FH fusion protein). Such polynucleotide may also be used for delivery and expression of CR2-FH. For example, in some embodiments, there is provided a polynucleotide encoding a fusion protein comprising a CR2 portion comprising a CR2 or a fragment thereof and a FH portion comprising a FH or a fragment thereof. In some embodiments, the polynucleotide also comprises a sequence encoding a signal peptide operably linked at the 5' end of the sequence encoding the CR2-FH fusion protein. Exemplary nucleotide sequences of signal peptides are provided in FIG. 7 (SEQ ID NO:12, 14, and 25). In some embodiments, a linker sequence is used for linking the CR2 portion and the FH portion. In some embodiments, the polynucleotide encodes a CR2-FH fusion protein having an amino acid sequence of SEQ ID NO:3. In some embodiments, the polynucleotide encodes a CR2-FH fusion protein having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of any of SEQ ID NO:3, SEQ ID NO:21, and SEQ ID NO:23. In some embodiments, the polynucleotide encodes a CR2-FH molecule comprising at least about any of 400, 450, 500, 550, or more contiguous nucleotides of any of SEQ ID NO:4, SEQ ID NO:22, and SEQ ID NO:24. In some embodiments, the polynucleotide comprises a sequence any of SEQ ID NO:4, SEQ ID NO:22, and SEQ ID NO:24. In some embodiments, the polynucleotide comprises a sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the nucleic acid sequence any of SEQ ID NO:4, SEQ ID NO:22, and SEQ ID NO:24. In some embodiments, the polynucleotide comprises least about any of 1200, 1300, 1400, 1500, 1600, or more contiguous nucleotides any of SEQ ID NO:4, SEQ ID NO:22, and SEQ ID NO:24. The polynucleotide may further include a sequence encoding a secretory signal sequence to secret the fusion protein into a medium. The polynucleotide encoding a secretory signal sequence include, for example, a polynucleotide encoding the signal sequence of CD5 or a polynucleotide sequence encoding the signal sequence of CR2.

Also provided are expression vectors comprising a polynucleotide described herein for expression of the CR2-FH fusion protein. The expression vector can be used to direct expression of a CR2-FH fusion protein in vitro or in vivo. The vector may include any element to establish a conventional function of a vector, for example, promoter, terminator, selection marker, and origin of replication. The promoter can be constitutive or regulative, and is selected from, for example, promoters of genes for galactokinase (GAL1), uridylyltransferase (GAL7), epimerase (GAL10), phosphoglycerate kinase (PGK), glyceraldehydes-3-phosphate dehydrogenase (GPD), alcohol dehydrogenase (ADH), and the like.

Many expression vectors are known to those of skill in the art. For example, *E. coli* may be transformed using pBR322, a plasmid derived from an *E. coli* species (Mandel et al., J. Mol. Biol., 53:154(1970)). Plasmid pBR322 contains genes for ampicillin and tetracycline resistance, and thus provides easy means for selection. Other vectors include different features such as different promoters, which are often important in expression. For example, plasmids pKK223-3 (Pharmacia Fine Chemicals, Uppsala, Sweden), pKK233-2 (Clontech, Palo Alto, Calif., USA), and pGEM1 (Promega Biotech, Madison, Wis., USA), are all commercially available. Other vectors that can be used in the present invention include, but are not limited to, pET21a (Studier et al., Methods Enzymol., 185: 60-89 (1990)), pR1T5, and pR1T2T (Pharmacia Biotechnology), and pB0475 (Cunningham et al., Science, 243: 1330-1336 (1989); U.S. Pat. No. 5,580,723). Mammalian expression vectors may contain non-transcribed elements such as an origin of replication, promoter and enhancer, and 5' or 3' nontranslated sequences such as ribosome binding sites, a polyadenylation site, acceptor site and splice donor, and transcriptional termination sequences. Promoters for use in mammalian expression vectors usually are for example viral promoters such as Polyoma, Adenovirus, HTLV, Simian Virus 40 (SV 40), and human cytomegalovirus (CMV). Vectors can also be constructed using standard techniques by combining the relevant traits of the vectors described above.

Also provided are host cells (such as isolated cells, transient cell lines, and stable cell lines) for expressing a CR2-FH fusion protein. The host cell may be prokaryotic or eukaryotes. Exemplary prokaryote host cells include *E. coli* K12 strain 294 (ATCC No. 31446), *E. coli* B, *E. coli* X1776 (ATCC No. 31537), *E. coli* W3110 (F-, gamma-, prototrophic/ATCC No. 27325), bacilli such as *Bacillus subtilis*, and other enterobacteriaceae such as *Salmonella typhimurium* or *Serratia marcesans*, and various *Pseudomonas* species. One suitable prokaryotic host cell is *E. coli* BL21 (Stratagene), which is deficient in the OmpT and Lon proteases, which may interfere with isolation of intact recombinant proteins, and useful with T7 promoter-driven vectors, such as the pET vectors. Another suitable prokaryote is *E. coli* W3110 (ATCC No. 27325). When expressed by prokaryotes the peptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic microbes such as filamentous fungi or yeast are suitable cloning or expression hosts for fusion-protein-encoding vectors. Saccharomyces cerevisiae is a commonly used lower eukaryotic host microorganism. Others include Schizosaccharomyces pombe (Beach and Nurse, Nature, 290: 140 (1981); EP 139,383 published 2 May 1985); *Kluyveromyces* hosts (U.S. Pat. No. 4,943,529; Fleer et al., Bio/Technology, 9:968-975 (1991)) such as, e.g., *K. lactis* (MW98-8C, CBS683, CBS4574; Louvencourt et al., J. Bacteriol., 154(2):737-742 (1983)), *K. fragilis* (ATCC 12,424), *K. bulgaricus* (ATCC No. 16,045), *K. wickeramii* (ATCC No. 24,178), *K. waltii* (ATCC No. 56,500), *K. drosophilarum* (ATCC No. 36,906; Van den Berg et al., Bio/Technology, 8:135 (1990)), *K. thermotolerans*, and *K. marxianus; yarrowia* (EP 402,226); *Pichia pastoris* (EP 183,070; Sreekrishna et al., J. Basic Microbiol., 28:265-278 (1988)); *Candida; Trichoderma reesia* (EP 244,234); *Neurospora crassa* (Case et al., Proc. Natl. Acad. Sci. USA, 76:5259-5263 (1979)); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., Biochem. Biophys. Res. Commun., 112:284-289 (1983); Tilbum et al., Gene, 26:205-221 (1983); Yelton et al., Proc. Natl.

Acad. Sci. USA, 81: 1470-1474 (1984)) and *A. niger* (Kelly and Hynes, EMBO J., 4:475-479 (1985)). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982). Host cells also include insect cells such as *Drosophila* S2 and *Spodoptera* Sf9, as well as plant cells.

Examples of useful mammalian host cell lines include, but are not limited to, HeLa, Chinese hamster ovary (CHO), COS-7, L cells, C127, 3T3, BHK, CHL-1, NSO, HEK293, W138, BHK, C127 or MDCK cell lines. Another exemplary mammalian cell line is CHL-1. When CHL-1 is used hygromycin is included as a eukaryotic selection marker. CHL-1 cells are derived from RPMI 7032 melanoma cells, a readily available human cell line. Cells suitable for use in this invention are commercially available from the ATCC.

In some embodiments, the host cell is a non-human host cell. In some embodiment, the host cell is a CHO cell. In some embodiments, the host cell is a 293 cell.

The CR2-FH molecules can be isolated by a variety of methods known in the art. In some embodiments, when the CR2-FH molecule is a fusion protein secreted into the growth media, the molecule can be purified directly from the media. If the fusion protein is not secreted, it is isolated from cell lysates. Cell disruption can be done by any conventional method, including freeze-thaw cycling, sonication, mechanical disruption, or use of cell lysing agents. The CR2-FH molecules can be obtained by various methods. These include, but are not limited to, immunoaffinity chromatography, reverse phase chromatography, cation exchange chromatography, anion exchange chromatography, hydrophobic interaction chromatography, gel filtration chromatography, and HPLC. For example, the CR2-FH molecule can be purified by immunoaffinity chromatography using an antibody that recognizes the CR2 portion or an antibody that recognizes the FH portion, or both. In some embodiments, an antibody recognizing the first two N-terminal SCR domains of CR2 is used for purifying the CR2-FH molecule. In some embodiments, the CR2-FH molecule is purified by ion change chromatography.

The peptide may or may not be properly folded when expressed as a fusion protein. These factors determine whether the fusion protein must be denatured and refolded, and if so, whether these procedures are employed before or after cleavage. When denaturing and refolding are needed, typically the peptide is treated with a chaotrope, such a guanidine HCl, and is then treated with a redox buffer, containing, for example, reduced and oxidized dithiothreitol or glutathione at the appropriate ratios, pH, and temperature, such that the peptide is refolded to its native structure.

The CR2-FH molecules described herein may also contain a tag (such as a cleavable tag) for purification. This tag can be fused to the C-terminus or N-terminus of the CR2 portion or the FH portion, and can be used to facilitate protein purification.

In some embodiments, the CR2-FH molecule could be synthesized de novo in whole or in part, using chemical methods well known in the art. For example, the component amino acid sequences can be synthesized by solid phase techniques, cleaved from the resin, and purified by preparative high performance liquid chromatography followed by chemical linkage to form a desired polypeptide. The composition of the synthetic peptides may be confirmed by amino acid analysis or sequencing.

The CR2-FH molecules can be assayed for their desired properties using in vitro or in vivo assays. For example, binding of CR2-FH to CR2 ligand can be determined by surface plasmon resonance method. By way of example, kinetic analysis of the interaction of the CR2-FH with C3dg-biotin can be performed using surface plasmon resonance (SPR) measurements made on a BIAcore 3000 instrument (Biacore AB, Uppsala, Sweden). Human C3dg-biotin can be bound to the surface of BIAcore streptavidin sensor chips by injecting C3dg-biotin over the surface of one flow cell of the chip. Binding can be evaluated over a range of CR2-FH concentrations. Association of CR2-FH molecule with the ligand can be monitored for a certain period of time (such as 120 seconds), after which the complex is allowed to dissociate in the presence of buffer only for an additional period of time (such as 120 seconds). Binding of CR2 fusion protein fragments to C3dg-immobilized flow cells can be corrected for binding to control flow cells. Binding data can be fitted to a 1:1 Langmuir binding model using BIAevaluation Version 3.1 software (BIAcore) and evaluated for best fit. The kinetic dissociation profiles obtained can be used to calculate on and off rates ($k_a$ and $k_d$) and affinity constants (KD) using the BIAevaluation Version 3.1 program. Other assay methods for ligand binding are known in the art and can also be used.

In vitro zymosan complement assay can be used to determine complement inhibitory activity of CR2-FH molecules. Lysis of rabbit erythrocytes by serum in Mg-EGTA is another measure of activity that can be used. Lysis in Mg-EGTA of human or sheep erythrocytes that have had sialic acid removed provides for additional measures of activity.

Pharmaceutical Compositions

Also provided herein are pharmaceutical compositions comprising a CR2-FH molecule and a pharmaceutically acceptable carrier. The pharmaceutical compositions may be suitable for a variety of modes of administration described herein, including for example systemic or localized administration. The pharmaceutical compositions can be in the form of eye drops, injectable solutions, or in a form suitable for inhalation (either through the mouth or the nose) or oral administration. The pharmaceutical compositions described herein can be packaged in single unit dosages or in multidosage forms.

In some embodiments, the pharmaceutical compositions comprise a CR2-FH molecule and a pharmaceutically acceptable carrier suitable for administration to human. In some embodiments, the pharmaceutical compositions comprise a CR2-FH molecule and a pharmaceutically acceptable carrier suitable for intraocular injection. In some embodiments, the pharmaceutical compositions comprise a CR2-FH molecule and a pharmaceutically acceptable carrier suitable for topical application to the eye. In some embodiments, the pharmaceutical compositions comprise a CR2-FH molecule and a pharmaceutically acceptable carrier suitable for intravenous injection. In some embodiments, the pharmaceutical compositions comprise a CR2-FH molecule and a pharmaceutically acceptable carrier suitable for injection into the arteries (such as renal arteries).

The compositions are generally formulated as sterile, substantially isotonic, and in full compliance with all Good Manufacturing Practice (GMP) regulations of the U.S. Food and Drug Administration. In some embodiments, the composition is free of pathogen. For injection, the pharmaceutical composition can be in the form of liquid solutions, for example in physiologically compatible buffers such as Hank's solution or Ringer's solution. In addition, the CR2-FH pharmaceutical composition can be in a solid form and redissolved or suspended immediately prior to use. Lyophilized compositions are also included.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

The present invention in some embodiments provides compositions comprising a CR2-FH molecule and a pharmaceutically acceptable carrier suitable for administration to the eye. Such pharmaceutical carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. Suitable pharmaceutical excipients include starch, glucose, lactose, sucrose, gelatin, malt, rice, sodium state, glycerol monostearate, glycerol, propylene, water, and the like. The pharmaceutical composition, if desired, can also contain minor amounts of wetting or emulsifying agents, or pH buffering agents. The CR2-FH molecule and other components of the composition may be encased in polymers or fibrin glues to provide controlled release of the molecule. These compositions can take the form of solutions, suspensions, emulsions, ointment, gel, or other solid or semisolid compositions, and the like. The compositions typically have a pH in the range of 4.5 to 8.0. The compositions must also be formulated to have osmotic values that are compatible with the aqueous humor of the eye and ophthalmic tissues. Such osmotic values will generally be in the range of from about 200 to about 400 milliosmoles per kilogram of water ("mOsm/kg"), but will preferably be about 300 mOsm/kg.

In some embodiment, the composition is formulated in accordance with routine procedures as a pharmaceutical composition adapted for injection intravenously, introperitoneally, or intravitreally. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions may further comprise additional ingredients, for example preservatives, buffers, tonicity agents, antioxidants and stabilizers, nonionic wetting or clarifying agents, viscosity-increasing agents, and the like.

Suitable preservatives for use in a solution include polyquaternium-1, benzalkonium chloride, thimerosal, chlorobutanol, methyl paraben, propyl paraben, phenylethyl alcohol, edetate disodium, sorbic acid, benzethonium chloride, and the like. Typically (but not necessarily) such preservatives are employed at a level of from 0.001% to 1.0% by weight.

Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5.

Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

The use of viscosity enhancing agents to provide topical compositions with viscosities greater than the viscosity of simple aqueous solutions may be desirable to increase ocular absorption of the active compounds by the target tissues or increase the retention time in the eye. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents know to those skilled in the art. Such agents are typically employed at a level of from 0.01% to 2% by weight.

In some embodiments, there is provided a pharmaceutical composition for delivery of a nucleotide encoding a CR2-FH molecule. The pharmaceutical composition for gene therapy can be in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical composition can comprise one or more cells which produce the gene delivery system.

In clinical settings, a gene delivery system for a gene therapeutic can be introduced into a subject by any of a number of methods. For instance, a pharmaceutical composition of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter, See U.S. Pat. No. 5,328,470, or by stereotactic injection, Chen et al. (1994), Proc. Natl. Acad. Sci., USA 91: 3054-3057. A polynucleotide encoding a CR2-FH molecule can be delivered in a gene therapy construct by electroporation using techniques described, Dev et al. (1994), *Cancer Treat. Rev.* 20:105-115.

In some embodiments, there is provided a pharmaceutical composition for gene delivery to the eye. Ophthalmic solutions useful for storing and/or delivering expression vectors have been disclosed, for example, in WO03077796A2.

Uses of CR2-FH Molecules and Compositions Thereof

The CR2-FH molecules described herein can function to specifically inhibit in vivo complement activation in the alternative complement pathway and inflammatory manifestations that accompany it, such as recruitment and activation of macrophages, neutrophils, platelets, and mast cells, edema, tissue damage, and direct activation of local and endogenous cells. Compositions comprising these molecules can therefore be used for treatment of diseases or conditions that are mediated by excessive or uncontrolled activation of the complement system, particularly diseases or conditions mediated by excessive or uncontrolled activation of the alternative complement pathway. In some embodiments, there are provided methods of treating diseases involving local inflammation process. In some embodiments, there are provided methods of treating diseases associated with FH deficiencies (for example a decrease in FH level, decrease in FH activity, or lack of wild type or protective FH), including, for example, age-related macular degeneration, membranoproliferative glomerulonephritis, proteineuric disease, hemolytic-uremic syndrome, recurrent microbial infection, ischemia reperfusion (such as renal ischemia reperfusion or intestinal ischemia reperfusion), organ transplant rejection, and chronic inflammation such as rheumatoid arthritis.

In some embodiments, there is provided a method of treating a disease in which the alternative complement pathway is implicated (such as macular degeneration, for example AMD) in an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there is provided a method of inhibiting complement activation in an individual having a disease in which the alternative complement pathway is implicated (such as macular degeneration, for example AMD), comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there is provided a method of inhibiting inflammation in an individual having a disease in which the alternative pathway is implicated (such as macular degeneration, for example AMD), comprising administering to the individual an effective amount of a composition comprising a CR2-FH molecule comprising: a) a CR2 portion comprising a CR2 or a fragment thereof, and b) a FH portion comprising a FH or a fragment thereof.

"Treating" or "to treat" a disease is defined as administering one or more CR2-FH molecules, with or without other therapeutic agents, in order to palliate, ameliorate, stabilize, reverse, slow, delay, prevent, reduce, or eliminate either the disease or a symptom of the disease, or to retard or stop the progression of the disease or a symptom of the disease. An "effective amount" is an amount sufficient to treat a disease, as defined above.

An "individual" is a vertebrate, preferably a mammal, more preferably a human. Mammals include, but are not limited to, farm animals, sport animals, pets, primates, mice and rats. In some embodiments, the individual is human. In some embodiments, the individual is an individual other than human. In some embodiments, the individual is an animal model for the study of a disease in which the alternative complement pathway is implicated. Individuals amenable to treatment include those who are presently asymptomatic but who are at risk of developing a symptomatic macular degeneration-related disorder at a later time. For example, human individuals include those having relatives who have experienced such a disease, and those whose risk is determined by analysis of genetic or biochemical markers, by biochemical methods, or by other assays such as T cell proliferation assay. In some embodiments, the individual is a human having a mutation or polymorph in its FH gene that indicates an increased susceptibility to develop a disease in which alternative complement pathway is implicated (such as age-related macular degeneration). In some embodiments, the individual has a wildtype or protective haplotype of FH. Different polymorphs of FH have been disclosed in US Pat. Pub. No. 20070020647, which is incorporated herein in its entirety.

The compositions described herein are particularly useful for treating macular degeneration, such as age-related macular degeneration (AMD). AMD is clinically characterized by progressive loss of central vision which occurs as a result of damage to the photoreceptor cells in an area of the retina called the macula. AMD has been broadly classified into two clinical states: a wet form and a dry form, with the dry form making up to 80-90% of total cases. The dry form is characterized clinically by the presence of macular drusen, which are localized deposits between the retinal pigment epithelium (RPE) and the Bruch's membrane, and by geographic atrophy characterized by RPE cell death with overlying photoreceptor atrophy. Wet AMD, which accounts for approximately 90% of serious vision loss, is associated with neovascularization in the area of the macular and leakage of these new vessels. The accumulation of blood and fluid can cause retina detachment followed by rapid photoreceptor degeneration and loss of vision. It is generally accepted that the wet form of AMD is preceded by and arises from the dry form.

Analysis of the contents of drusen in AMD patients has shown a large number of inflammatory proteins including amyloid proteins, coagulation factors, and a large number of proteins of the complement pathway. A genetic variation in the complement factor H substantially raises the risk of age-related macular degeneration (AMD), suggesting that uncontrolled complement activation underlies the pathogenesis of AMD. Edward et al., *Science* 2005, 308:421; Haines et al., *Science* 2005, 308:419; Klein et al., *Science* 308:385-389; Hageman et al., *Proc. Natl. Acad. Sci. USA* 2005, 102:7227.

The present invention provides methods of treating AMD (such as wet or dry forms of AMD) by administering an effective amount of a composition comprising a CR2-FH molecule. In some embodiments, the invention provides methods of treating or preventing one or more aspects or symptoms of AMD, including, but not limited to, formation of ocular drusen, inflammation in the eye or eye tissue, loss of photoreceptor cells, loss of vision (including for example visual acuity and visual field), neovascularization (such as choroidal neovascularization or CNV), and retinal detachment. Other related aspects, such as photoreceptor degeneration, RPE degeneration, retinal degeneration, chorioretinal degeneration, cone degeneration, retinal dysfunction, retinal damage in response to light exposure (such as constant light exposure), damage of the Bruch's membrane, loss of RPE function, loss of integrity of the histoarchitecture of the cells and/or extracellular matrix of the normal macular, loss of function of the cells in the macula, photoreceptor dystrophy, mucopolysaccharidoses, rod-cone dystrophies, cone-rod dystrophies, anterior and posterior uvitis, and diabetic neuropathy, are also included.

In some embodiments, there are provided methods of treating macular degeneration (such as age-related macular degeneration or AMD) in an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, the disease to be treated is a dry form of AMD. In some embodiments, the disease to be treated is a wet form of AMD.

In some embodiments, there are provided methods of treating (such as reducing, delaying, eliminating, or preventing) formation of drusen in the eye of an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there are provided methods of treating (such as reducing, delaying, eliminating, or preventing) inflammation in the eye of an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there are provided methods of treating (such as reducing, delaying, eliminating, or preventing) loss of photoreceptors cells in an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there are provided methods of treating (such as reducing, delaying, eliminating, or preventing) loss of photoreceptors cells in an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there are provided methods of treating (such as reducing, delaying, eliminating, or preventing) neovascularization associated with AMD, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there are provided methods of treating (such as reducing, delaying, eliminating, or preventing) retinal detachment associated with AMD, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there are provided methods of improving (including for example decreasing, delaying, or blocking loss of) visual acuity or visual field in the eye of an individual, comprising administering to the individual an effective amount of a composition comprising a CR2-FH molecule comprising: a) a CR2 portion comprising a CR2 or a fragment thereof, and b) a FH portion comprising a FH or a fragment thereof.

In addition to macular degeneration, other eye diseases that can be treated by methods of the present invention include, for example, retinitis pigmentosa, diabetic retinopathy, and other eye diseases that involve a local inflammatory process. In some embodiments, the eye disease is diabetic retinopathy. In some embodiments, the eye disease is retinitis pigmentosa.

The methods described herein can also be useful for treatment of certain renal diseases. In some embodiments, there are provided methods of treating membranoproliferative glomerulonephritis type II (MPGN II). MPGN II is a rare kidney disease leading to persisting proteinuria, hematuria, and nephritic syndrome. FH deficiency and dysfunction in MPGN II have been reported in several cases. For example, mutations in FH have been found in human patients with MPGN II. Pigs of the Norwegian Yorkshire breed have FH defects that are inherited in a recessive pattern. These animals develop MPGN II and show massive complement deposits in the renal glomeruli and die at an early age because of the renal failure. Furthermore, an autoantibody that recognizes FH has been described in a patient with hypocomplementemic MPGN II. Targeting FH to complement activation sites thus will have therapeutic effects on an individual having MPGN II. Accordingly, in some embodiments, there are provided methods of treating MPGN II in an individual, comprising administering to the individual a composition comprising a CR2-FH molecule comprising: a) a CR2 portion comprising a CR2 or a fragment thereof, and b) a FH portion comprising a FH or a fragment thereof. In some embodiments, there are provided methods of treating proteinuria associated with MPGN II. In some embodiments, there are provided methods of treating hematuria associated with MPGN II. In some embodiments, there is provided a method of treating nephritic syndrome associated with MPGN II.

In some embodiments, there are provided methods of treating hemolytic-uremic syndrome (HUS). HUS is a disease consisting of microangiopathic hemolytic anemia, thrombocytopenia, and acute renal failure, caused by continuous platelet degradation in the periphery and platelet thrombin in the microcirculation of the kidney. Zipfel, *Seminars in Thrombosis Hemostasis,* 2001, 27(3):191-199. There is now considerable evidence that the nondiarrheal form of HUS (D-HUS) is associated with alternations and mutations of FH. In addition, autoantibodies to FH have been reported in HUS patients. Targeting FH to complement activation sites thus will have therapeutic effects on an individual having HUS. Accordingly, in some embodiments, there are provided methods of treating HUS in an individual, comprising administering to the individual an effective amount of a composition comprising a CR2-FH molecule comprising: a) a CR2 portion comprising a CR2 or a fragment thereof, and b) a FH portion comprising a FH or a fragment thereof. In some embodiments, there are provided methods of treating microangiopathic hemolytic anemia associated with HUS. In some embodiments, there is provided a method of treating thrombocytopenia associated with HUS. In some embodiments, there are provided methods of treating acute renal failure associated with HUS.

In some embodiments, the disease to be treated is systemic lupus erythematosus, such as lupus nephritis. Systemic lupus erythematosus (SLE) is the prototypic autoimmune disease resulting in multiorgan involvement. This anti-self response is characterized by autoantibodies directed against a variety of nuclear and cytoplasmic cellular components. These autoantibodies bind to their respective antigens, forming immune complexes which circulate and eventually deposit in tissues. This immune complex deposition causes chronic inflammation and tissue damage. Complement pathways (including the alternative complement pathway) are implicated in the pathology of SLE, and the methods provided herein are thus useful for treating SLE (such as lupus nephritis).

In some embodiments, the disease to be treated is rheumatoid arthritis. Rheumatoid arthritis is a chronic disease which can exhibit a variety of systemic manifestations. This disease has an unknown etiology and characteristically exhibits a persistent inflammatory synovitis which usually involves peripheral joints in a symmetric distribution. Complement-mediated inflammation which causes cartilage destruction, bone erosions and, ultimately, joint deformities is the most important feature of this disease. Methods provided herein are thus useful for treatment of rheumatoid arthritis.

In some embodiments, the disease to be treated is ischemia reperfusion. Ischemia reperfusion (I/R) injury refers to inflammatory injury to the endothelium and underlying parenchymal tissues following reperfusion of hypoxic tissues. It is a general syndrome that is responsible for both acute and chronic injury to various tissues including, for example, myocardium, central nervous system, hind limb and intestine. Ischemia reperfusion injury can result in necrosis and irreversible cell injury. The complement pathway (including the alternative complement pathway) is a major mediator of I/R injury. Methods provided herein are thus useful for treatment of ischemia reperfusion that occurs in any organ or tissues, including, but not limited to, intestinal ischemia-reperfusion injury, renal ischemia-reperfusion injury, cardiac ischemia-reperfusion injury, ischemia-reperfusion injury of other internal organs such as the lung or liver, central nervous system ischemia-reperfusion injury, ischemia-reperfusion injury of the limbs or digits, trauma-induced hypovolemic, or ischemia-reperfusion injury of any transplanted organ or tissue. Ischemia-reperfusion injury can also occur in conjunction with a variety of other conditions including, but not limited to, stroke, spinal cord injury, trauma-induced hypovolemic shock, and autoimmune diseases such as rheumatoid arthritis (e.g., which can be greatly worsened by ischemic injury of the synovium) or a variety of other inflammatory diseases (diseases mediated by inflammation or wherein inflammation is a symptom that may result in or be associated with ischemic events and reperfusion). Other conditions and diseases in which ischemia-reperfusion injury occurs will be known to those of skill in the art.

In some embodiments, there are provided methods of treating a drusen-associated disease. The term "drusen-associated disease" refers to any disease in which formation of drusen or drusen-like extracellular disease plaque takes place, and for which drusen or drusen-like extracellular disease plaque causes or contributes to thereto or represents a sign thereof. For example, AMD, characterized by the formation of macular drusen, is considered as a drusen-associated disease. Non-ocular drusen-related disease include, but are not limited to, amyloidosis, elastosis, dense deposit disease, and/or atherosclerosis. The term "drusen-related disease" also includes glomerulonephritis (such as MPGN II).

Other diseases in which the alternative complement pathway is implicated that can be treated by methods of the present invention include, for example: (1) tissue damage due to ischemia-reperfusion following acute myocardial infarction, aneurysm, stroke, hemorrhagic shock, crush injury, multiple organ failure, hypovolemic shock intestinal ischemia, spinal cord injury, and traumatic brain injury; (2) inflammatory disorders, e.g., burns, endotoxemia and septic shock, adult respiratory distress syndrome, cardiopulmonary bypass, hemodialysis; anaphylactic shock, severe asthma, angioedema, Crohn's disease, sickle cell anemia, poststreptococcal glomerulonephritis, membraneous nephritis, and pancreatitis; (3) transplant rejection, e.g., hyperacute xenograft rejection; (4) pregnancy related diseases such as recurrent fetal loss and pre-eclampsia, and (5) adverse drug reactions, e.g., drug allergy, IL-2 induced vascular leakage syndrome and radiographic contrast media allergy. Autoimmune disorders including, but not limited to, myasthenia gravis, Alzheimer's disease, multiple sclerosis, emphysema, obesity, rheumatoid arthritis, systemic lupus erythematosus, multiple sclerosis, myasthenia gravis, insulin-dependent diabetes mellitus, acute disseminated encephalomyelitis, Addison's disease, antiphospholipid antibody syndrome, autoimmune hepatitis, Crohn's disease, Goodpasture's syndrome, Graves' disease, Guillain-Barré syndrome, Hashimoto's disease, idiopathic thrombocytopenic purpura, pemphigus, Sjögren's syndrome, and Takayasu's arteritis, may also be treated with the inhibitors of the invention.

In some embodiments, the disease to be treated is any of the following: post cardiopulmonary bypass complications; myocardial infarction; ischemia/reperfusion injury; stroke; acute respiratory distress syndrome (ARDS); sepsis; burn injury; inflammation associated with cardiopulmonary bypass and hemodialysis; plasmapheresis; plateletpheresis; leukopheresis; extracorporeal; membrane oxygenation (ECMO); heparin-induced extracorporeal LDL precipitation (HELP); radiographic contrast media induced allergic response; transplant rejection; and other inflammatory conditions and autoimmune/immune complex diseases such as multiple sclerosis, myasthemia gravis, pancreatitis, rheumatoid arthritis, Alzheimer's disease, asthma, thermal injury, anaphylactic shock, bowel inflammation, urticaria, angioedema, vasculitis, glomerularnephritis, and Sjogren's syndrome, lupus erythromatosus, and glomerular nephritis.

The compositions described herein can be administered to an individual via any route, including, but not limited to, intravenous (e.g., by infusion pumps), intraperitoneal, intraocular, intra-arterial, intrapulmonary, oral, inhalation, intravesicular, intramuscular, intra-tracheal, subcutaneous, intraocular, intrathecal, transdermal, transpleural, intraarterial, topical, inhalational (e.g., as mists of sprays), mucosal (such as via nasal mucosa), subcutaneous, transdermal, gastrointestinal, intraarticular, intracisternal, intraventricular, rectal (i.e., via suppository), vaginal (i.e., via pessary), intracranial, intraurethral, intrahepatic, and intratumoral. In some embodiments, the compositions are administered systemically (for example by intravenous injection). In some embodiments, the compositions are administered locally (for example by intraarterial or intraocular injection).

In some embodiments, the compositions are administered directly to the eye or the eye tissue. In some embodiments, the compositions are administered topically to the eye, for example, in eye drops. In some embodiments, the compositions are administered by injection to the eye (intraocular injection) or to the tissues associated with the eye. The compositions can be administered, for example, by intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. These methods are known in the art. For example, for a description of exemplary periocular routes for retinal drug delivery, see Periocular routes for retinal drug delivery, Raghava et al. (2004), *Expert Opin. Drug Deliv.* 1(1):99-114. The compositions may be administered, for example, to the vitreous, aqueous humor, sclera, conjunctiva, the area between the sclera and conjunctiva, the retina choroids tissues, macula, or other area in or proximate to the eye of an individual. The compositions can also be administered to the individual as an implant. Preferred implants are biocompatible and/or biodegradable sustained release formulations which gradually release the compounds over a period of time. Ocular implants for drug delivery are well-known in the art. See, e.g., U.S. Pat. No. 5,501,856, 5,476,511, and 6,331, 313. The compositions can also be administered to the individual using iontophoresis, including, but are not limited to, the ionophoretic methods described in U.S. Pat. No. 4,454, 151 and U.S. Pat. App. Pub. No. 2003/0181531 and 2004/0058313.

In some embodiments, the compositions are administered intravascularly, such as intravenously (IV) or intraarterially. In some embodiments (for example for the treatment of renal diseases), the compositions are administered directly into arteries (such as renal arteries).

The optimal effective amount of the compositions can be determined empirically and will depend on the type and severity of the disease, route of administration, disease progression and health, mass and body area of the individual. Such determinations are within the skill of one in the art. The effective amount can also be determined based on in vitro complement activation assays. Examples of dosages of CR2-FH molecules which can be used for methods described herein include, but are not limited to, an effective amount within the dosage range of any of about 0.01 µg/kg to about 300 mg/kg, or within about 0.1 µg/kg to about 40 mg/kg, or with about 1 µg/kg to about 20 mg/kg, or within about 1 µg/kg to about 10 mg/kg. For example, when administered intraocularly, the composition may be administered at low microgram ranges, including for example about 0.1 µg/kg or less, about 0.05 µg/kg or less, or 0.01 µg/kg or less. In some embodiments, the amount of CR2-FH administered to an individual is about 10 µg to about 500 mg per dose, including for example any of about 10 µg to about 50 µg, about 50 µg to about 100 µg, about 100 µg to about 200 µg, about 200 µg to about 300 µg, about 300 µg to about 500 µg, about 500 µg to about 1 mg, about 1 mg to about 10 mg, about 10 mg to about 50 mg, about 50 mg to about 100 mg, about 100 mg to about 200 mg, about 200 mg to about 300 mg, about 300 mg to about 400 mg, or about 400 mg to about 500 mg per dose.

The CR2-FH compositions may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgical implanted in various locations in the eye or tissue associated with the eye, such as intraocular, intravitreal, subretinal, periocular, subconjunctival, or sub-Tenons.

The pharmaceutical compositions can be administered alone or in combination with other molecules known to have a beneficial effect on retinal attachment or damaged retinal tissue, including molecules capable of tissue repair and regeneration and/or inhibiting inflammation. Examples of useful cofactors include anti-VEGF agents (such as an antibody against VEGF), basic fibroblast growth factor (bFGF), ciliary neurotrophic factor (CNTF), axokine (a mutein of CNTF), leukemia inhibitory factor (LIF), neutrophin 3 (NT-3), neurotrophin-4 (NT-4), nerve growth factor (NGF), insulin-like growth factor II, prostaglandin E2, 30 kD survival factor, taurine, and vitamin A. Other useful cofactors include symptom-alleviating cofactors, including antiseptics, antibiotics, antiviral and antifungal agents and analgesics and anesthetics.

Gene Therapy

The CR2-FH molecules can also be delivered by expression of the CR2-FH fusion protein in vivo, which is often referred to as "gene therapy". For example, cells may be engineered with a polynucleotide (DNA or RNA) encoding for the fusion protein ex vivo, the engineered cells are then provided to an individual to be treated with the fusion protein. Such methods are well-known in the art. For example, cells may be engineered by procedures known in the art by use of a retroviral particle containing RNA encoding for the fusion protein of the present invention.

Local delivery of the fusion proteins of the present invention using gene therapy may provide the therapeutic agent to the target area, for example to the eye or the eye tissue.

Methods of gene delivery are known in the art. These methods include, but are not limited to, direct DNA transfer, see, e.g., Wolff et al. (1990) *Science* 247: 1465-1468; 2) Liposome-mediated DNA transfer, see, e.g., Caplen et al. (1995) *Nature Med.* 3:39-46; Crystal (1995) *Nature Med.* 1:15-17; Gao and Huang (1991) *Biochem. Biophys. Res. Comm.* 179:280-285; 3) Retrovirus-mediated DNA transfer, see, e.g., Kay et al. (1993) *Science* 262:117-119; Anderson (1992) *Science* 256:808-813; 4) DNA Virus-mediated DNA transfer. Such DNA viruses include adenoviruses (preferably Ad2 or Ad5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al. (1994) *Gene Therapy* 1:367-384; U.S. Pat. No. 4,797,368, incorporated herein by reference, and U.S. Pat. No. 5,139,941.

Retroviruses from which the retroviral plasmid vectors hereinabove mentioned may be derived include, but are not limited to, Moloney Mouse Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Mouse Leukemia Virus.

Adenoviruses have the advantage that they have a broad host range, can infect quiescent or terminally differentiated cells, such as neurons or hepatocytes, and appear essentially non-oncogenic. See, e.g., Ali et al. (1994), supra, p. 367. Adenoviruses do not appear to integrate into the host genome. Because they exist extrachromosomally, the risk of insertional mutagenesis is greatly reduced. Ali et al. (1994), supra, p. 373.

Adeno-associated viruses exhibit similar advantages as adenoviral-based vectors. However, AAVs exhibit site-specific integration on human chromosome 19 (Ali et al. (1994), supra, p. 377).

The gene therapy vectors-include one or more promoters. In some embodiments, the vector has a promoter that drives expression in multiple cell types. In some embodiments, the vector has a promoter that drives expression in specific cell types (such as cells of retina or cells in the kidney). Suitable promoters which may be employed include, but are not limited to, the retroviral LTR; the SV40 promoter; and the human cytomegalovirus (CVM) promoter described in Miller et al.

(1989) *Biotechniques* 7(9):980-990, or any other promoter (e.g., cellular promoters such as eukaryotic cellular promoters including, but not limited to, the histone, pol III, and .beta.-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding a CR2-FH fusion protein is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoA1 promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoter.

Retroviral plasmid vectors can be employed to transduce packaging cell lines to form producer cell lines. Examples of packaging cells which maybe transfected are described in Miller (1990) *Human Gene Therapy* 1:5-14. The vectors may transduce the packaging cells through any means known in the art. Such means include, but are not limited to, electroporation, the use of liposomes, and CaPO.sub.4 precipitation. In one alternative, the retroviral plasmid vector may be encapsulated into a liposome, or coupled to a lipid, and then administered to a host. The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

In some embodiments, gene delivery vectors which direct expression of CR2-FH in the eye are used. Vectors for gene delivery to the eye are known in the art, and have been disclosed, for example, in U.S. Pat. No. 6,943,153, and U.S. Patent Application Publication Nos. US20020194630, US20030129164, US200600627165.

In some embodiments, the complement activation is inhibited by contacting a body fluid with a composition comprising a CR2-FH molecule ex vivo under conditions that permit the CR2-FH molecule to function to inhibit complement activation. Suitable body fluids include those that can be returned to the individual, such as blood, plasma, or lymph. Affinity adsorption apheresis is described generally in Nilsson et al. (1988) *Blood* 58(1):38-44; Christie et al. (1993) *Transfusion* 33:234-242; Richter et al. (1997) *ASAIO J.* 43(1):53-59; Suzuki et al. (1994) *Autoimmunity* 19: 105-112; U.S. Pat. No. 5,733,254; Richter et al. (1993) *Metabol. Clin. Exp.* 42:888-894; and Wallukat et al. (1996) *Int'l J. Card.* 54:1910195.

Accordingly, the invention include methods of treating one or more diseases described herein in an individual comprising treating the individual's blood extracoporeally (i.e., outside the body or ex vivo) with a composition comprising a CR2-FH molecule under conditions that permit the molecule to function to inhibit complement activation, and returning the blood to the individual.

Unit Dosages, Articles of Manufacture, and Kits

Also provided are unit dosage forms of CR2-FH molecule compositions, each dosage containing from about 0.01 mg to about 50 mg, including for example any of about 0.1 mg to about 50 mg, about 1 mg to about 50 mg, about 5 mg to about 40 mg, about 10 mg to about 20 mg, or about 15 mg of the CR2-FH molecule. In some embodiments, the unit dosage forms of CR2-FH molecule composition comprises about any of 0.01 mg-0.1 mg, 0.1 mg-0.2 mg, 0.2 mg-0.25 mg, 0.25 mg-0.3 mg, 0.3 mg-0.35 mg, 0.35 mg-0.4 mg, 0.4 mg-0.5 mg, 0.5 mg-1.0 mg, 10 mg-20 mg, 20 mg-50 mg, 50 mg-80 mg, 80 mg-100 mg, 100 mg-150 mg, 150 mg-200 mg, 200 mg-250 mg, 250 mg-300 mg, 300 mg-400 mg, or 400 mg-500 mg CR2-FH molecule. In some embodiments, the unit dosage form comprises about 0.25 mg CH2-FH molecule. The term "unit dosage form" refers to a physically discrete unit suitable as unitatry dosages for an individual, each unit containing a predetermined quantity of active material calculated to produce the desired therapeutic effect, in association with a suitable pharmaceutical carrier, diluent, or excipient. These unit dosage forms can be stored in a suitable packaging in single or multiple unit dosages and may also be further sterilized and sealed.

Also provided are articles of manufacture comprising the compositions described herein in suitable packaging. Suitable packaging for compositions (such as ophthalmic compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions (or unit dosages forms and/or articles of manufacture) described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein.

EXAMPLES

Example 1

Exemplary Sequences of CR2-FH Molecules and Signal Peptides

FIGS. 4-6 provide exemplary amino acid sequences of CR2-FH molecules described herein (SEQ ID NOs: 5-10). "nnn" represents an optional linker.

FIG. 7 provides exemplary amino acid sequences of signaling peptides described herein (SEQ ID NOs: 11 and 13) and polynucleotides encoding the signaling peptides (SEQ ID NOs:12 and 14).

FIG. 9 provides amino acid sequence of a mouse CR2-FH fusion protein (designated as CR2-fH or CR2NLFH) (SEQ ID NO:17) and a polynucleotide that encodes a mouse CR2-FH plus the signal peptide (SEQ ID NO:18).

FIG. 10 provides the DNA sequence of CR2NLFHFH, a mouse CR2-FH fusion protein containing a CR2 portion and two FH portions without a linker sequence (SEQ ID NO:19).

FIG. 11 provides the DNA sequence of CR2LFHFH, a mouse CR2-FH fusion protein containing a CR2 portion linked to two FH portions via a linker sequence (SEQ ID NO:20).

FIG. 20 provides amino acid sequence of a human CR2-FH fusion protein (designated as human CR2-fH or CR2fH) (SEQ ID NO:21) and a polynucleotide that encodes a human CR2-fH plus the signal peptide (SEQ ID NO:22).

FIG. 21 provides amino acid sequence of a human CR2-FH fusion protein containing two FH portions (designated as human CR2-FH2 or CR2fH2 or human CR2fH2) (SEQ ID NO:23) and a polynucleotide that encodes a human CR2-FH2 plus the signal peptide (SEQ ID NO:24).

Example 2

In Vitro Inhibition of Alternative Pathway by CR2-FH

Mouse fusion proteins containing the first four SCR domains of CR2 and the first five SCR domains of FH (with linker (CR2LFH) or without linker (CR2NLFH or CR2-fH)) were made by recombinant DNA cloning and gene expression method. The sequence for one of the CR2-FH fusion proteins is provided in FIG. 9. SEQ ID NO:17 is the polypeptide sequence of the CR2-FH fusion protein. SEQ ID NO:18 is the nucleotide used to encode the fusion protein, as well as a signal peptide at the N-terminus of the signal peptide.

A mouse CR2-FH fusion protein (designated as CR2LFHFH, CR2-fH2 or CR2-fHH) containing the first four SCR domains of CR2 and two tandemly linked FH portions (each containing the first five SCR domains of FH) was also made. The CR2 portion and the first FH portion was linked by a linker sequence. The DNA sequence (including the DNA encoding the signal peptide) of CR2LFHFH is provided in FIG. 11 (SEQ ID NO:20).

In vitro assays for activation of the alternative pathway were conducted as essentially described in Quigg et al., *J. Immunol.* 1998, 160(9):4553-60. Factor H (fH) or CR2-Crry were used as controls in the experiment. Specifically, 50 mg of zymosan beads in 10 ml of 0.15M NaCl were activated by boiling for 60 minutes, and washed twice in PBS. In each reaction mixture add: 1) 10 mM EGTA and 5 MM MgCl2 (final concentration); 2) $1 \times 10^7$ beads; 3) 10 mM EDTA (negative control 1) or HIC serum (negative control 2) or increasing concentration of one of the CR2-FH fusion proteins or control proteins; 4) 10 µl of serum; and 5) PBS to bring the total volume to 100 µl. The mixtures were incubated at 37° C. for 20 minutes, and the reactions were stopped by addition of 10 mM EDTA (final concentration). The beads were washed twice with cold PBSB (PBS with 1% BSA), and incubated with FTIC-conjugated goat-anti-C3 antibody for one hour on ice. The sample were then washed twice in PBSB, resuspended with 1% paraformaldehyde and analyzed under flow cytometry.

FIG. 12A provides a graphic representation of data obtained in an in vitro zymosan complement assay using mouse CR2-FH fusion proteins (CR2-fH) and factor H alone (fH). As shown in the figure, CR2-fH was significantly more effective than FH in inhibiting complement activation. FIG. 12B provides a graphic representation of data obtained in an in vitro zymosan complement assay using the first five SCR domains of mouse FH (FH 15) and the first four domains of mouse CR2 (CR2). The first five SCR domains of mouse FH had an EC50 of 250 nM, which approximately equal to the amount of FH in serum. The molecule having the first four domains of CR2 has no inhibitory effect at all. These data demonstrate that the effect seen with CR2-FH is due to the combined effects of the two portions of the molecule, rather than the independent function of each portion.

FIG. 13 provides a graphic representation of data obtained in an in vitro zymosan complement assay using mouse CR2-FH fusion protein with linker (CR2LFH), CR2-FH fusion protein without linker (CR2NLFH), CR2-FH-FH with linker (CR2LFHFH), and CR2-Crry. As shown in the figure, CR2-FH was more effective than CR2-Crry in inhibiting complement activation of the alternative pathway. CR2LFH and CR2NLFH were equally effective in inhibiting complement activation of the alternative pathway. CR2LFHFH is much more effective than CR2LFH and CR2NLFH.

Example 3

Treatment of Intestinal Ischemia and Reperfusion Injury by CR2-FH

This experiment shows treatment of intestinal ischemia and reperfusion injury in a mouse model.

Intestinal ischemia reperfusion injury. Three adult male mice aged 8 weeks and weighing 20-25 g were anesthetized with 10 mg/kg ketamine and 6 mg/kg xylazine by i.p. injection. Animals were breathing spontaneously and body temperature was maintained using a heat mat for the entire experiment. A medial laparotomy was preformed and the intestines were carefully moved allowing access to the superior mesenteric artery. The superior mesenteric artery was clamped using a microsurgical clamp (Fine Instruments, USA). Ischemia was confirmed by palor of the small intestine. Sham treated mice underwent laparotomy without clamping of superior mesenteric artery. After 30 min. ischemia the arterial clamp was removed allowing reperfusion of the mesenteric vasculature. Animals were sutured using 6.0 ethicon suture and allowed to reperfuse for 2 hours. 0.1 mg or 0.05 mg CR2-fH, or control (PBS) were administered i.v. 30 minutes post reperfusion and animals were sacrificed 90 minutes later following a total of 2 hours of reperfusion.

Histology. Tissue samples for histological staining were taken from the intestine and either fixed in 10% formalin at 4° C. overnight and subsequently processed to paraffin, or frozen in liquid nitrogen for immunofluorescence analysis. Sections of intestine from each animal were stained with hematoxylin and eosin and scored for mucosal damage and villi height as previously described (46). Briefly, a score of 0 was assigned to a normal villus; villi with tip distortion were scored as 1; villi lacking goblet cells and containing Gugenheims' spaces were scored 2; villi with patchy disruption of the epithelial cells were scored 3; villi exposed but intact lamina propria and epithelial cell sloughing were assigned 4; villi in which lamina propria were exuding were scored as 5, and finally, villi displaying hemorrhage or denuded villi were scored as 6. All histological evaluations were carried out in a blinded fashion.

The results of the experiment are shown in FIG. 14A. As shown in the figure, both 0.1 mg and 0.05 mg of CR2-fH showed protective effect in the animal model compared to the control animals even though the control animals had normal levels of circulating endogenous factor H (about 0.5 mg/ml) in excess of the amounts of CR2-fH administered.

Example 3.1

Treatment of Intestinal Ischemia and Reperfusion Injury by Mouse CR2-FH

The experiment was carried out essentially as disclosed in Example 3.

Briefly, 0.05 mg, 0.1 mg, or 0.2 mg of mouse CR2-fH or mouse CR2-fH2 (CR2-fHH) were administered i.v. 30 minutes post reperfusion and animals were sacrificed 90 minutes later for histology analysis. The results of the experiment are shown in FIG. 14B. As shown in FIG. 14B, both mouse CR2-fH and mouse CR2-fHH protected the intestine from complement-mediated ischemia reperfusion injury.

Example 3.2

Treatment of Intestinal Ischemia and Reperfusion Injury by Mouse CR2-FH

This experiment shows the effects of mouse CR2-fH and CR2-fH2 on alternative complement pathway and intestinal ischemia reperfusion. The experiments are carried out essentially as described above.

In vitro assays demonstrated that mouse CR2-fH was significantly more effective in inhibiting the alternative pathway of complement than CR2-Crry, and that mouse CR2-fH2 was about 2-fold more effective than mouse CR2-fH. The complement inhibitory activity of mouse CR2-fH was dependent on CR2-mediated targeting as demonstrated by anti-CR2 antibody blocking experiments. Furthermore, purified mouse factor H had only minimal complement inhibitory activities in the in vitro assays.

Mouse CR2-fH and mouse CR2-fH2 targeted to sites of local and remote (lung) complement activation following intestinal ischemia and reperfusion injury, and both proteins protected the intestinal mucosa and the lung parenchyma from injury at a low dose and in a dose dependent manner. Although mouse CR2-fH2 was a more potent inhibitor of the alternative complement pathway than mouse CR2-fH in vitro, there was no difference in the protective effect of the two proteins in the in vivo model. Compared to CR2-Crry, an approximate 2-fold higher dose of mouse CR2-fH was required to provide equivalent protection from local injury.

Example 4

Treatment of Renal Ischemia Reperfusion by Mouse CR2-FH

This example shows the effect of CR2-FH on renal ischemia reperfusion.

Protocol for induction of ischemic ARF. Mice weighing 20-25 grams were anesthetized with 300 μl of 2,2,2-Tribromoethanol (Sigma-Aldrich) injected intra-peritoneally. After the mice were anesthetized, they were placed on a heating pad to maintain their body temperature during surgery. Laparotomies were then performed, and the renal pedicles were located and isolated by blunt dissection. The pedicles were clamped with surgical clips (Miltex Instrument Company, Inc.), and occlusion of blood flow was confirmed by visual inspection of the kidneys. The clamps were left in place for 24 minutes and then released. The time of ischemia was chosen to obtain a reversible model of ischemic ARF with a minimum of vascular thrombosis, and to avoid animal mortality. The kidneys were observed for approximately one minute to ensure blood re-flow. After 15 minutes of reperfusion the mice received 0.25 mg of the mouse CR2-fH (CR2NLFH) intraperitoneally. Fascia and skin were sutured with 4-0 silk (United States Surgical). The mice were volume resuscitated with 0.5 ml of normal saline and kept in an incubator at 29° C. to maintain body temperature.

After 24 hours of reperfusion the mice were anesthetized, and blood was obtained by cardiac puncture. Laparotomy was performed and the kidneys were harvested. The study protocol was approved by the University of Colorado Health Sciences Center Animal Care and Use Committee.

Serum Urea Nitrogen Measurements. Serum urea nitrogen was determined for each mouse using a Beckman Autoanalyzer (Beckman). The result of is shown in FIG. 15A. As shown in the figure, serum urea nitrogen was reduced in mouse CR2-fH treated animals, indicating preservation of kidney function.

Renal morphology. After the kidneys were removed from the mice, sagittal sections were fixed in 4% paraformaldehyde. After being embedded in paraffin, four μm sections were cut and stained with periodic acid Schiff. The sections were evaluated by a renal pathologist in a blinded fashion. The cortex and outer stripe of the outer medulla were assessed for epithelial necrosis, loss of brush border, tubular dilatation and cast formation. At least ten fields (400×) were reviewed for each slide, and the percentage of tubules displaying these findings was determined. The kidney sections were scored as follows based on the percentage of affected tubules: 0, none; 1, <10%, 2, 11-25%, 3, 26-45%, 4, 46-75%, 5, >75%. The result of the experiment is shown in FIG. 15B. As shown in the figure, CR2-fH showed protective effect in the animal model compared to the control animal.

Immunofluorescence. For immunofluorescence, sagittal sections of the kidneys were snap frozen in OCT compound (Sakura Finetek). Four μm sections were cut with a cryostat and stored at −70° C. The slides were later fixed with acetone and incubated with the FITC conjugated antibody to mouse C3 (Cappel). After hybridization with the antibody for one hour at room temperature, the slides were counterstained with hematoxylin (Vector Laboratories, Inc.). The results of the experiment are shown in FIGS. 15C and 15D. As shown in the figure, more C3 was deposited into kidneys of sham treated mice (15C) relative to mouse CR2-fH-treated mice (15D).

Example 5

Treatment of Age-Related Macular Degeneration by CR2-FH

Constant light exposed albino rats are used as animal models for age-related macular degeneration (dry AMD). Five to eight animals are injected intraocularly under anesthesia every other day with a CR2-FH fusion protein (1 μl of 4.3 mg/ml stock solution), starting with the first injection the day prior to the onset of continuous light exposure (days −1, 1, 3, 5, 7). One eye serves as the experimental, while the other eye serves as the PBS-injected control eye. Animals are tested with ERG on day 8 and then euthanized for histology and PCR analysis. Number of rows of photoreceptors in eyes injected with CR2-FH are compared with those of the PBS control eyes.

The effect of CR2-FH are measured using three parameters: functional activity (ERG and DC potentials, i.e., photoreceptor and RPE responses), histology and measures of inflammation (e.g., gene expression by RT-PCR and protein expression by immunohistochemistry.

In a second animal model (wet AMD), we test whether eliminating complement activators reduces choroidal neovascularization (CNV). CNV is produced in five to eight rats with a Krypton laser (200 mW, 50 µm, 0.05 sec) and documented in choroidal flatmounts after fluorescein injections.

The effect of CR2-FH are measured using four parameters: functional activity (ERG and DC potentials, i.e., photoreceptor and RPE responses), histology, vascular integrity (choroidal flatmounts after fluorescein injections) and measures of inflammation (e.g., gene expression by RT-PCR and protein expression by immunohistochemistry).

Example 6

Reduction in CNV Volume by Mouse CR2-FH

For generation of CNV, 3-month-old animals were anesthetized using xylazine and ketamine (20 and 80 mg/kg, respectively) and pupils dilated with a drop of phenylephrine HCl (2.5%) and atropine sulfate (1%). Argon laser photocoagulation (532 nm, 50 µm spot size, 0.05 s duration, 250 mW) was used to generate four laser spots in each eye surrounding the optic nerve, using a handheld coverslip as a contact lens. A bubble formed at a laser spot indicated the rupture of Bruch's membrane. Nozaki et al., *Proc. Natl. Acad. Sci.* 2006, 103(7):2328-33.

For assessment of CNV lesions, CNV size was determined in flat-mount preparations of RPE/choroids stained with isolectin B (which binds to terminal β-D-galactose residues on the surface of endothelial cells and selectively labels the mouse vasculature). Fluorescence measurements taken in 2 µm sections using confocal microscopy were used for size determination. In short, a Z-stack of images through the CNV lesion was obtained, using the same laser intensity setting for all experiments. For each slice the overall fluorescence was determined and plotted against depth.

For electroretinography, animals were anesthetized using xylazine (20 mg/kg bodyweight) and ketamine (80 mg/kg bodyweight). Pupils were dilated with a drop of phenylephrine HCl (2.5%) and tropicamide (1%). Body temperature was stabilized via a DC-powered heating pad held at 37° C. The ERG setup used was previously described by Rohrer et al., J. Neurosci., 1999, 19(20): 8919-30 and was built according to Lyubarsky and Pugh Lyubarsky et al., J. Neurosci., 1996, 16(2):563-571. Stimulus light intensity was controlled using neutral density filters. Stimulus paradigms. Animals were dark-adapted overnight and ERGs will be recorded. Rods were analyzed in response to single-flash stimuli of increasing light intensity. The single-flash responses were an average of at least 3 flashes with an inter-stimulus interval (ISI) of 15 s to 2 min (lowest intensity to highest, respectively). The different ISIs ensured that ERG amplitudes at a given intensity were identical between the first and the last flash. Data analysis. For all ERG recordings, a-wave amplitude were measured from baseline to trough; b-wave amplitude were measured from a-wave trough or baseline to peak of b-wave, and implicit times were measured from onset of stimulus to a-wave trough or b-wave peak.

In one experiment, mice were treated with intravenous mouse CR2-fH (250 µg) 30 minutes post laser burn, 48 hours post laser burn, and 6 hours post laser burn. 6 days post later burn, retinal function was assessed, then mice were sacrificed for histology.

FIG. 16 shows a- and b-wave retinal responses in mice treated with or without CR2-fH. As shown in FIG. 16, both a- and b-waves of retinal response were protected by CR2-fH treatment relative to PBS treatment. FIGS. 17A and 17B show isolectin-b staining of lesions 6 days post laser burn. FIG. 17C shows quantification of lesion sizes based on the isolectin-b staining. As shown in FIGS. 17A-C, mice treated with CR2-fH show significant reduction in lesion size as compared to animals treated with PBS.

In a separate experiment, 1 µg mouse CR2-fH was administered intraoptically immediately after laser burn, 48 hours post burn, and 96 hours post burn. Eyes were collected at day 6 for histology. Lesions were visualized by isolectin-b staining. The results are shown in FIG. 18. FIGS. 18A and 18B show isolectin-b staining of lesions 6 days post laser burn. FIG. 18C shows quantification of lesion size based on the isolectin-b staining. As shown in FIGS. 18A-C, CR2-fH delivered directly to the eye reduces spread of the lesion.

Example 7

Delay of Onset of Antibody-Mediated Rejection in a Mouse Heterotropic Heart Transplant Model by Mouse CR2-FH In this experiment, hearts were heterotopically transplanted from C3H donor mice into Balb/c recipient mice. This strain combination promotes a TH2 immune phenotype which promotes acute vascular rejection, and is characterized by anti-graft antibody production and graft deposition of complement activation fragments.

Recipient mice were treated with 1) PBS, i.v., 2) a single 0.25 mg dose of mouse CR2-fH, i.v. 30 minutes post reperfusion, and 3) multiple doses of 0.25 mg mouse CR2-fH i.v. starting 30 minutes post reperfusion and then every three days thereafter.

Hearts were harvested 24 hours post reperfusion for analysis. Mouse CR2-fH treated animals were protected from ischemia and reperfusion injury as assessed by histology, the absence of C3, a reduction in neutrophil infiltration, and a reduction in inflammatory cytokines.

The effects of mouse CR2-fH on acute vascular rejection are shown in FIG. 21. As shown in the figure, control heart transplant recipients survived 7.1±1 days, compared to 11.1±1.6 days (single dose group) and 10.7±1.3 days (multiple dose group). There is a significant improvement in survival in mice treated with mouse CR2-fH when compared to controls (p=0.02).

At the time of harvest there were no obvious differences in pathological rejection profiles or in the levels of anti-donor antibodies between any of the groups. Interestingly, there appears to be no significant improvement in survival associated with the administration of multiple doses of mouse CR2-fH when compared to the single dose group (p<0.05).

Example 8

Inhibition of Alternative Complement Pathway by Human CR2-FH

The protein sequences of human CR2-FH (SEQ ID NO:21, also designated as CR2fH) and human CR2-FH2 (SEQ ID NO:23, also designated as CR2fH2), not including signal peptides, are shown in FIGS. 20 and 21, respectively. The nucleic acid sequences of human CR2-FH (SEQ ID NO: 22) and human CR2-FH2 (SEQ ID NO:24), including nucleotide sequences for signal peptides, are shown in FIGS. 20 and 21, respectively.

Human CR2-FH and human CR2-FH2 were purified from transfected 293 cell supernatants by affinity chromatography using HB5-separose, which contains anti-human CR2 monoclonal antibody HB5 (ATCC catalog # HB-135) linked to CNBr-activated sepharose (Amershan Biosciences). Crude CR2-FH or CR2-FH2 supernatants were passed over the matrix, washed with PBS, and eluted in 0.1M glycine-HCl, pH 3.0. The eluted fraction was immediately neutralized by the addition of 1M Tris-Cl, pH 9.0 followed by exchange into PBS using centricon columns (Millipore). 300 ng of nonreduced, purified CR2-FH and CR2-FH2 were resolved on SDS-PAGE and visualized by Commassie staining. CR2-FH was present as two distinct proteins, as determined by mass spectrometry (Alphalyse, Palo Alto, Calif.) of 64.0 and 65.3 kDa which resolved into a single band following deglycosylation, while CR2-FH2 was a single species of 99.2 kDa. The inherent secondary structure of these molecules makes them run smaller than their actual molecular weight under nonreducing conditions.

The effects of human CR2-FH and human CR2-FH2 on alternative pathway specific C3b deposition onto zymosan particles are shown in FIG. 22A. Briefly, Zymosan particles were incubated in PBS containing 5 mM $Mg^{2+}$, 10 mM EGTA, 10% human serum, and increasing concentrations of CR2-FH and CR2-FH2 for 30 minutes at room temperature with FITC conjugated goat anti-human C3 antibody. Zymosan was pelleted and washed, followed by FACS analysis. As shown in FIG. 24A, both CR2-FH and CR2-FH2 inhibited activation of the alternative complement pathway. Similar results were obtained by incubating with mouse serum followed by detection with FITC conjugated goat anti-mouse C3 antibody. Significantly, there was 200-400 nM FH present in the assay system. The CR2-FH had an EC50 of 8-22 nM, which was 20-fold lower than the amount of FH present in the assay, demonstrating a clear benefit of targeted FH over endogenous FH.

The effects of human CR2-FH and human CR2-FH2 on alternative pathway-mediated erythrocyte lysis are shown in FIG. 22B. Briefly, rabbit erythrocytes ($1 \times 10^8$) were incubated with varying concentrations of CR2-FH or CR2-FH2 in 1×GVB++ (Boston BioProducts) and 17% human serum for 30 minutes at 37° C. The reaction was stopped with the addition of one tenth volume cold PBS followed by centrifugation to pellet unlysed erythrocytes. Hemolysis was quantified by measuring $OD_{415nm}$. As shown in FIG. 24B, both CR2-FH and CR2-FH2 significantly inhibited activation of the alternative complement pathway. Significantly, there was 340-680 nM FH present in the assay. The CR2-FH had an EC50 of 20-30 nM, which was 15-20 fold lower than the amount of FH present in the assay, demonstrating a clear benefit of targeted FH over endogenous FH.

Example 9

Inhibition of the Alternative Complement Pathway by Mouse CR2-FH

This example shows inhibition of the alternative complement pathway by mouse CR2-FH using serum for mice deficient in the classical pathway.

ELISA assay with immune complexes of collagen-anti-collagen antibodies on the plates were used. C3 deposition/activation was measured by using anti-C3b antibody in the presence of serum from wildtype or from C4-/C4-mice. Different amounts of full length mouse FH (2 μg/10 μl), the first four SCR domains of mouse CR2 (2 μg/10 μl), and mouse CR2-FH (2 μg/10 μl) were added to the serum. The result of the in vitro study is shown in FIG. 23. As shown in the figure, mouse CR2-FH had little effect on C3b deposition using serum from wildtype mice. By contrast, mouse CR2-FH almost completely prevented C3b deposition in serum from classical pathway deficient mice. Mouse FH or mouse CR2, on the other hand, had little effects in both assay systems. This experiment demonstrates a clear advantage of using CR2-FH to inhibit alternative complement pathway, particularly when the classical complement pathway is not involved.

To further demonstrate that the inhibition of C3b deposition observed with CR2-FH was due to inhibition of the alternative pathway, we studied the effects of CR2-FH on C3b deposition in the absence of the classical pathway (C4-/C4-mice). Calcium inhibits the lectin complement pathway. FIG. 24 shows a titration curve of mouse CR2-FH in calcium sufficient buffer using serum from C4-/C4-knockout mice. As shown in the figure, CR2-FH significantly inhibits C3b deposition at the concentration of 0.5 μg/μl.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A complement receptor 2 (CR2)-factor H (FH) molecule comprising:
   a) a CR2 portion comprising a CR2 or a fragment thereof, and
   b) a FH portion comprising a FH or a fragment thereof, said FH or fragment thereof comprising at least the first four N-terminal short consensus repeat (SCR) domains of FH;
   wherein the CR2 portion of the CR2-FH molecule is capable of binding to a CR2 ligand, and wherein the FH portion of the CR2-FH molecule is capable of inhibiting complement activation of the alternative pathway.

2. The CR2-FH molecule of claim 1, wherein the CR2 portion comprises at least the first two N-terminal SCR domains of CR2.

3. The CR2-FH molecule of claim 1, wherein the CR2 portion comprises at least the first four N-terminal SCR domains of CR2.

4. The CR2-FH molecule of claim 1, wherein the FH portion comprises at least the first five N-terminal SCR domains of FH.

5. The CR2-FH molecule of claim 1, wherein the CR2-FH molecule comprises two or more FH portions, wherein the two or more FH portions each comprise a FH or fragment thereof comprising at least the first four N-terminal SCR domains of FH.

6. The CR2-FH molecule of claim 1, wherein the CR2 portion comprises the first four N-terminal SCR domains of CR2 and the FH portion comprises the first five N-terminal SCR domains of FH.

7. The CR2-FH molecule of claim 6, wherein the CR2 portion comprises amino acids 23 to 271 of SEQ ID NO:1 and the FH portion comprises amino acids 21 to 320 of SEQ ID NO:2.

8. The CR2-FH molecule of claim 1, wherein the CR2-FH molecule is a fusion protein.

9. A polynucleotide encoding the fusion protein of claim 8.

10. A vector encoding the polynucleotide of claim 9.

11. A host cell comprising the polynucleotide of claim 10.

12. A pharmaceutical composition comprising a CR2-FH molecule of claim 1 and a pharmaceutically acceptable carrier.

13. The composition of claim 12, wherein the composition is suitable for intraocular, intravenous, intraarterial, sub-cutaneous, intratracheal, or inhalational administration.

14. A method of treating a disease in which the alternative complement pathway is implicated in an individual, comprising administering to the individual an effective amount of a pharmaceutical composition of claim 12.

15. The method of claim 14, wherein the disease in which the alternative complement pathway is implicated is any of macular degeneration, rheumatoid arthritis, ischemia reperfusion, organ transplant rejection, membranoproliferative glomerulonephritis, type II (MPGN II), hemolytic uremic syndrome (HUS), and lupus nephritis.

16. The method of claim 15, wherein the disease in which the alternative complement pathway is implicated is age-related macular degeneration.

17. The method of claim 15, wherein the disease in which the alternative complement pathway is implicated is ischemia reperfusion.

18. The method of claim 15, wherein the disease in which alternative complement pathway is implicated is organ transplant rejection.

19. The method of claim 15, wherein the HUS is factor H-related.

20. A method of treating an individual having a disease in which the alternative complement pathway is implicated, wherein the disease is characterized by symptoms comprising microangiopathic hemolytic anemia, thrombocytopenia, and acute renal failure, the method comprising administering to the individual an effective amount of a pharmaceutical composition of claim 12.

* * * * *

SEQUENCE LISTING

```
<160> NUMBER OF SEQ ID NOS: 26

<210> SEQ ID NO 1
<211> LENGTH: 1087
<212> TYPE: PRT
<213> ORGANISM: Homo sapiens

<400> SEQUENCE: 1

Met Gly Ala Ala Gly Leu Leu Gly Val Phe Leu Ala Leu Val Ala Pro
 1               5                   10                  15

Gly Val Leu Gly Ile Ser Cys Gly Ser Pro Pro Pro Ile Leu Asn Gly
                20                  25                  30

Arg Ile Ser Tyr Tyr Ser Thr Pro Ile Ala Val Gly Thr Val Ile Arg
            35                  40                  45

Tyr Ser Cys Ser Gly Thr Phe Arg Leu Ile Gly Glu Lys Ser Leu Leu
        50                  55                  60
```

```
Cys Ile Thr Lys Asp Lys Val Asp Gly Thr Trp Asp Lys Pro Ala Pro
 65                  70                  75                  80

Lys Cys Glu Tyr Phe Asn Lys Tyr Ser Ser Cys Pro Glu Pro Ile Val
                 85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
            115                 120                 125

Ser Val Trp Cys Gln Ala Asn Asn Met Trp Gly Pro Thr Arg Leu Pro
130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
            195                 200                 205

Thr Cys Glu Glu Ala Arg Cys Lys Ser Leu Gly Arg Phe Pro Asn Gly
210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
            260                 265                 270

Glu Ile Phe Cys Pro Ser Pro Pro Ile Leu Asn Gly Arg His Ile
            275                 280                 285

Gly Asn Ser Leu Ala Asn Val Ser Tyr Gly Ser Ile Val Thr Tyr Thr
            290                 295                 300

Cys Asp Pro Asp Pro Glu Glu Gly Val Asn Phe Ile Leu Ile Gly Glu
305                 310                 315                 320

Ser Thr Leu Arg Cys Thr Val Asp Ser Gln Lys Thr Gly Thr Trp Ser
                325                 330                 335

Gly Pro Ala Pro Arg Cys Glu Leu Ser Thr Ser Ala Val Gln Cys Pro
            340                 345                 350

His Pro Gln Ile Leu Arg Gly Arg Met Val Ser Gly Gln Lys Asp Arg
            355                 360                 365

Tyr Thr Tyr Asn Asp Thr Val Ile Phe Ala Cys Met Phe Gly Phe Thr
            370                 375                 380

Leu Lys Gly Ser Lys Gln Ile Arg Cys Asn Ala Gln Gly Thr Trp Glu
385                 390                 395                 400

Pro Ser Ala Pro Val Cys Glu Lys Glu Cys Gln Ala Pro Pro Asn Ile
                405                 410                 415

Leu Asn Gly Gln Lys Glu Asp Arg His Met Val Arg Phe Asp Pro Gly
            420                 425                 430

Thr Ser Ile Lys Tyr Ser Cys Asn Pro Gly Tyr Val Leu Val Gly Glu
            435                 440                 445

Glu Ser Ile Gln Cys Thr Ser Glu Gly Val Trp Thr Pro Pro Val Pro
            450                 455                 460

Gln Cys Lys Val Ala Ala Cys Glu Ala Thr Gly Arg Gln Leu Leu Thr
465                 470                 475                 480
```

```
Lys Pro Gln His Gln Phe Val Arg Pro Asp Val Asn Ser Ser Cys Gly
                485                 490                 495
Glu Gly Tyr Lys Leu Ser Gly Ser Val Tyr Gln Glu Cys Gln Gly Thr
            500                 505                 510
Ile Pro Trp Phe Met Glu Ile Arg Leu Cys Lys Glu Ile Thr Cys Pro
        515                 520                 525
Pro Pro Pro Val Ile Tyr Asn Gly Ala His Thr Gly Ser Ser Leu Glu
    530                 535                 540
Asp Phe Pro Tyr Gly Thr Thr Val Thr Tyr Thr Cys Asn Pro Gly Pro
545                 550                 555                 560
Glu Arg Gly Val Glu Phe Ser Leu Ile Gly Glu Ser Thr Ile Arg Cys
                565                 570                 575
Thr Ser Asn Asp Gln Glu Arg Gly Thr Trp Ser Gly Pro Ala Pro Leu
            580                 585                 590
Cys Lys Leu Ser Leu Leu Ala Val Gln Cys Ser His Val His Ile Ala
        595                 600                 605
Asn Gly Tyr Lys Ile Ser Gly Lys Glu Ala Pro Tyr Phe Tyr Asn Asp
    610                 615                 620
Thr Val Thr Phe Lys Cys Tyr Ser Gly Phe Thr Leu Lys Gly Ser Ser
625                 630                 635                 640
Gln Ile Arg Cys Lys Arg Asp Asn Thr Trp Asp Pro Glu Ile Pro Val
                645                 650                 655
Cys Glu Lys Gly Cys Gln Pro Pro Gly Leu His His Gly Arg His
            660                 665                 670
Thr Gly Gly Asn Thr Val Phe Phe Val Ser Gly Met Thr Val Asp Tyr
        675                 680                 685
Thr Cys Asp Pro Gly Tyr Leu Leu Val Gly Asn Lys Ser Ile His Cys
    690                 695                 700
Met Pro Ser Gly Asn Trp Ser Pro Ser Ala Pro Arg Cys Glu Glu Thr
705                 710                 715                 720
Cys Gln His Val Arg Gln Ser Leu Gln Glu Leu Pro Ala Gly Ser Arg
                725                 730                 735
Val Glu Leu Val Asn Thr Ser Cys Gln Asp Gly Tyr Gln Leu Thr Gly
            740                 745                 750
His Ala Tyr Gln Met Cys Gln Asp Ala Glu Asn Gly Ile Trp Phe Lys
        755                 760                 765
Lys Ile Pro Leu Cys Lys Val Ile His Cys His Pro Pro Pro Val Ile
    770                 775                 780
Val Asn Gly Lys His Thr Gly Met Met Ala Glu Asn Phe Leu Tyr Gly
785                 790                 795                 800
Asn Glu Val Ser Tyr Glu Cys Asp Gln Gly Phe Tyr Leu Leu Gly Glu
                805                 810                 815
Lys Asn Cys Ser Ala Glu Val Ile Leu Lys Ala Trp Ile Leu Glu Arg
            820                 825                 830
Ala Phe Pro Gln Cys Leu Arg Ser Leu Cys Pro Asn Pro Glu Val Lys
        835                 840                 845
His Gly Tyr Lys Leu Asn Lys Thr His Ser Ala Tyr Ser His Asn Asp
    850                 855                 860
Ile Val Tyr Val Asp Cys Asn Pro Gly Phe Ile Met Asn Gly Ser Arg
865                 870                 875                 880
Val Ile Arg Cys His Thr Asp Asn Thr Trp Val Pro Gly Val Pro Thr
                885                 890                 895
Cys Ile Lys Lys Ala Phe Ile Gly Cys Pro Pro Pro Pro Lys Thr Pro
```

-continued

```
                900                 905                 910
Asn Gly Asn His Thr Gly Gly Asn Ile Ala Arg Phe Ser Pro Gly Met
        915                 920                 925

Ser Ile Leu Tyr Ser Cys Asp Gln Gly Tyr Leu Val Val Gly Glu Pro
    930                 935                 940

Leu Leu Leu Cys Thr His Glu Gly Thr Trp Ser Gln Pro Ala Pro His
945                 950                 955                 960

Cys Lys Glu Val Asn Cys Ser Ser Pro Ala Asp Met Asp Gly Ile Gln
                965                 970                 975

Lys Gly Leu Glu Pro Arg Lys Met Tyr Gln Tyr Gly Ala Val Val Thr
        980                 985                 990

Leu Glu Cys Glu Asp Gly Tyr Met Leu Glu Gly Ser Pro Gln Ser Gln
    995                 1000                1005

Cys Gln Ser Asp His Gln Trp Asn Pro Pro Leu Ala Val Cys Arg Ser
    1010                1015                1020

Arg Ser Leu Ala Pro Val Leu Cys Gly Ile Ala Ala Gly Leu Ile Leu
1025                1030                1035                1040

Leu Thr Phe Leu Ile Val Ile Thr Leu Tyr Val Ile Ser Lys His Arg
                1045                1050                1055

Glu Arg Asn Tyr Tyr Thr Asp Thr Ser Gln Lys Glu Ala Phe His Leu
        1060                1065                1070

Glu Ala Arg Glu Val Tyr Ser Val Asp Pro Tyr Asn Pro Ala Ser
    1075                1080                1085

<210> SEQ ID NO 2
<211> LENGTH: 1231
<212> TYPE: PRT
<213> ORGANISM: Homo sapiens

<400> SEQUENCE: 2

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190
```

-continued

```
Ser Asp Asp Gly Phe Trp Ser Lys Glu Lys Pro Lys Cys Val Glu Ile
    195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn His Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Lys Thr Cys
        435                 440                 445

Ser Lys Ser Ser Ile Asp Ile Glu Asn Gly Phe Ile Ser Glu Ser Gln
    450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Arg Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
    530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605

Val Gln Cys Tyr His Phe Gly Leu Ser Pro Asp Leu Pro Ile Cys Lys
```

-continued

```
              610                 615                 620
Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Glu
                645                 650                 655

Tyr Tyr Cys Asn Pro Arg Phe Leu Met Lys Gly Pro Asn Lys Ile Gln
                660                 665                 670

Cys Val Asp Gly Glu Trp Thr Thr Leu Pro Val Cys Ile Val Glu Glu
                675                 680                 685

Ser Thr Cys Gly Asp Ile Pro Glu Leu Glu His Gly Trp Ala Gln Leu
690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
                740                 745                 750

Cys Lys Ser Ser Asn Leu Ile Ile Leu Glu Glu His Leu Lys Asn Lys
                755                 760                 765

Lys Glu Phe Asp His Asn Ser Asn Ile Arg Tyr Arg Cys Arg Gly Lys
                770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
                820                 825                 830

Glu Lys Val Ser Val Leu Cys Gln Glu Asn Tyr Leu Ile Gln Glu Gly
                835                 840                 845

Glu Glu Ile Thr Cys Lys Asp Gly Arg Trp Gln Ser Ile Pro Leu Cys
                850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
                900                 905                 910

Thr Thr Cys Tyr Met Gly Lys Trp Ser Ser Pro Pro Gln Cys Glu Gly
                915                 920                 925

Leu Pro Cys Lys Ser Pro Pro Glu Ile Ser His Gly Val Val Ala His
                930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
                980                 985                 990

Pro Ser Phe Glu Asn Ala Ile Pro Met Gly Glu Lys Lys Asp Val Tyr
                995                1000                1005

Lys Ala Gly Glu Gln Val Thr Tyr Thr Cys Ala Thr Tyr Tyr Lys Met
                1010                1015                1020

Asp Gly Ala Ser Asn Val Thr Cys Ile Asn Ser Arg Trp Thr Gly Arg
1025                1030                1035                1040
```

```
Pro Thr Cys Arg Asp Thr Ser Cys Val Asn Pro Thr Val Gln Asn
                1045                1050                1055

Ala Tyr Ile Val Ser Arg Gln Met Ser Lys Tyr Pro Ser Gly Glu Arg
                1060                1065                1070

Val Arg Tyr Gln Cys Arg Ser Pro Tyr Glu Met Phe Gly Asp Glu Glu
                1075                1080                1085

Val Met Cys Leu Asn Gly Asn Trp Thr Glu Pro Pro Gln Cys Lys Asp
                1090                1095                1100

Ser Thr Gly Lys Cys Gly Pro Pro Pro Ile Asp Asn Gly Asp Ile
1105                1110                1115                1120

Thr Ser Phe Pro Leu Ser Val Tyr Ala Pro Ala Ser Ser Val Glu Tyr
                1125                1130                1135

Gln Cys Gln Asn Leu Tyr Gln Leu Glu Gly Asn Lys Arg Ile Thr Cys
                1140                1145                1150

Arg Asn Gly Gln Trp Ser Glu Pro Pro Lys Cys Leu His Pro Cys Val
                1155                1160                1165

Ile Ser Arg Glu Ile Met Glu Asn Tyr Asn Ile Ala Leu Arg Trp Thr
                1170                1175                1180

Ala Lys Gln Lys Leu Tyr Ser Arg Thr Gly Glu Ser Val Glu Phe Val
1185                1190                1195                1200

Cys Lys Arg Gly Tyr Arg Leu Ser Arg Ser His Thr Leu Arg Thr
                1205                1210                1215

Thr Cys Trp Asp Gly Lys Leu Glu Tyr Pro Thr Cys Ala Lys Arg
                1220                1225                1230

<210> SEQ ID NO 3
<211> LENGTH: 570
<212> TYPE: PRT
<213> ORGANISM: Homo sapiens
<220> FEATURE:
<221> NAME/KEY: VARIANT
<222> LOCATION: 197
<223> OTHER INFORMATION: Xaa = Unknown or Other

<400> SEQUENCE: 3

Ile Ser Cys Gly Ser Pro Pro Ile Leu Asn Gly Arg Ile Ser Tyr
1               5                   10                  15

Tyr Ser Thr Pro Ile Ala Val Gly Thr Val Ile Arg Tyr Ser Cys Ser
                20                  25                  30

Gly Thr Phe Arg Leu Ile Gly Glu Lys Ser Leu Leu Cys Ile Thr Lys
                35                  40                  45

Asp Lys Val Asp Gly Thr Trp Asp Lys Pro Ala Pro Lys Cys Glu Tyr
50                  55                  60

Phe Asn Lys Tyr Ser Ser Cys Pro Glu Pro Ile Val Pro Gly Gly Tyr
65                  70                  75                  80

Lys Ile Arg Gly Ser Thr Pro Tyr Arg His Gly Asp Ser Val Thr Phe
                85                  90                  95

Ala Cys Lys Thr Asn Phe Ser Met Asn Gly Asn Lys Ser Val Trp Cys
                100                 105                 110

Gln Ala Asn Asn Ile Asn Asn Met Trp Gly Pro Thr Arg Leu Pro Thr
                115                 120                 125

Cys Val Ser Val Phe Pro Leu Glu Cys Pro Ala Leu Pro Met Ile His
                130                 135                 140

Asn Gly His His Thr Ser Glu Asn Val Gly Ser Ile Ala Pro Gly Leu
145                 150                 155                 160
```

-continued

```
Ser Val Thr Tyr Ser Cys Glu Ser Gly Tyr Leu Leu Val Gly Glu Lys
            165                 170                 175

Ile Ile Asn Cys Leu Ser Ser Gly Lys Trp Ser Ala Val Pro Pro Thr
        180                 185                 190

Cys Glu Glu Ala Xaa Cys Lys Ser Leu Gly Arg Phe Pro Asn Gly Lys
            195                 200                 205

Val Lys Glu Pro Pro Ile Leu Arg Val Gly Val Thr Ala Asn Phe Phe
        210                 215                 220

Cys Asp Glu Gly Tyr Arg Leu Gln Gly Pro Pro Ser Ser Arg Cys Val
225                 230                 235                 240

Ile Ala Gly Gln Gly Val Ala Trp Thr Lys Met Pro Val Cys Gly Gly
            245                 250                 255

Gly Gly Ser Gly Gly Gly Gly Ser Cys Val Ala Glu Asp Cys Asn Glu
            260                 265                 270

Leu Pro Pro Arg Arg Asn Thr Glu Ile Leu Thr Gly Ser Trp Ser Asp
        275                 280                 285

Gln Thr Tyr Pro Glu Gly Thr Gln Ala Ile Tyr Lys Cys Arg Pro Gly
        290                 295                 300

Tyr Arg Ser Leu Gly Asn Val Ile Met Val Cys Arg Lys Gly Glu Trp
305                 310                 315                 320

Val Ala Leu Asn Pro Leu Arg Lys Cys Gln Lys Arg Pro Cys Gly His
            325                 330                 335

Pro Gly Asp Thr Pro Phe Gly Thr Phe Thr Leu Thr Gly Gly Asn Val
            340                 345                 350

Phe Glu Tyr Gly Val Lys Ala Val Tyr Thr Cys Asn Glu Gly Tyr Gln
        355                 360                 365

Leu Leu Gly Glu Ile Asn Tyr Arg Glu Cys Asp Thr Asp Gly Trp Thr
        370                 375                 380

Asn Asp Ile Pro Ile Cys Glu Val Val Lys Cys Leu Pro Val Thr Ala
385                 390                 395                 400

Pro Glu Asn Gly Lys Ile Val Ser Ser Ala Met Glu Pro Asp Arg Glu
            405                 410                 415

Tyr His Phe Gly Gln Ala Val Arg Phe Val Cys Asn Ser Gly Tyr Lys
            420                 425                 430

Ile Glu Gly Asp Glu Glu Met His Cys Ser Asp Asp Gly Phe Trp Ser
        435                 440                 445

Lys Glu Lys Pro Lys Cys Val Glu Ile Ser Cys Lys Ser Pro Asp Val
        450                 455                 460

Ile Asn Gly Ser Pro Ile Ser Gln Lys Ile Ile Tyr Lys Glu Asn Glu
465                 470                 475                 480

Arg Phe Gln Tyr Lys Cys Asn Met Gly Tyr Glu Tyr Ser Glu Arg Gly
            485                 490                 495

Asp Ala Val Cys Thr Glu Ser Gly Trp Arg Pro Leu Pro Ser Cys Glu
            500                 505                 510

Glu Lys Ser Cys Asp Asn Pro Tyr Ile Pro Asn Gly Asp Tyr Ser Pro
        515                 520                 525

Leu Arg Ile Lys His Arg Thr Gly Asp Glu Ile Thr Tyr Gln Cys Arg
        530                 535                 540

Asn Gly Phe Tyr Pro Ala Thr Arg Gly Asn Thr Ala Lys Cys Thr Ser
545                 550                 555                 560

Thr Gly Trp Ile Pro Ala Pro Arg Cys Thr
            565                 570
```

<210> SEQ ID NO 4
<211> LENGTH: 1711
<212> TYPE: DNA
<213> ORGANISM: Homo sapiens

<400> SEQUENCE: 4

```
atttcttgtg gctctcctcc gcctatccta aatggccgga ttagttatta ttctaccccc    60
attgctgttg gtaccgtgat aaggtacagt tgttcaggta ccttccgcct cattggagaa   120
aaaagtctat tatgcataac taaagacaaa gtggatggaa cctgggataa acctgctcct   180
aaatgtgaat atttcaataa atattcttct tgccctgagc ccatagtacc aggaggatac   240
aaaattagag gctctacacc ctacagacat ggtgattctg tgacatttgc ctgtaaaacc   300
aacttctcca tgaacggaaa caagtctgtt tggtgtcaag caataatat aataatatg   360
tgggggccga cacgactacc aacctgtgta agtgttttcc ctctcgagtg tccagcactt   420
cctatgatcc acaatggaca tcacacaagt gagaatgttg gctccattgc tccaggattg   480
tctgtgactt acagctgtga atctggttac ttgcttgttg gagaaaagat cattaactgt   540
ttgtcttcgg gaaatggag tgctgtcccc cccacatgtg aagaggcacg ctgtaaatct   600
ctaggacgat ttcccaatgg gaaggtaaag gagcctccaa ttctccgggt tggtgtaact   660
gcaaactttt tctgtgatga agggtatcga ctgcaaggcc caccttctag tcggtgtgta   720
attgctggac agggagttgc ttggaccaaa atgccagtat gtggcggagg tgggtcgggt   780
ggcggcggat cttgtgtagc agaagattgc aatgaacttc ctccaagaag aaatacagaa   840
attctgacag gttcctggtc tgaccaaaca tatccagaag gcacccaggc tatctataaa   900
tgccgccctg gatatagatc tcttggaaat gtaataatgg tatgcaggaa gggagaatgg   960
gttgctctta atccattaag gaaatgtcag aaaaggccct gtggacatcc tggagatact   1020
cctttttggta ctttttaccct tacaggagga aatgtgtttg aatatggtgt aaaagctgtg   1080
tatacatgta atgagggta tcaattgcta ggtgagatta ttaccgtgaa atgtgacaca   1140
gatggatgga ccaatgatat tcctatatgt gaagttgtga agtgtttacc agtgacagca   1200
ccagagaatg gaaaaattgt cagtagtgca atggaaccag atcgggaata ccattttgga   1260
caagcagtac ggtttgtatg taactcaggc tacaagattg aaggagatga agaaatgcat   1320
tgttcagacg atggttttg gagtaaagag aaaccaaagt gtgtggaaat ttcatgcaaa   1380
tccccagatg ttataaatgg atctcctata tctcagaaga ttatttataa ggagaatgaa   1440
cgatttcaat ataaatgtaa catgggttat gaatacagtg aaagaggaga tgctgtatgc   1500
actgaatctg gatggcgtcc gttgccttca tgtgaagaaa aatcatgtga taatccttat   1560
attccaaatg gtgactactc acctttaagg attaaacaca gaactggaga tgaaatcacg   1620
taccagtgta gaaatggttt ttatcctgca acccggggaa atacagccaa atgcacaagt   1680
actggctgga tacctgctcc gagatgtacc t                                    1711
```

<210> SEQ ID NO 5
<211> LENGTH: 560
<212> TYPE: PRT
<213> ORGANISM: Murine
<220> FEATURE:
<221> NAME/KEY: VARIANT
<222> LOCATION: 252, 253, 254
<223> OTHER INFORMATION: Xaa = Unknown or Other
<220> FEATURE:
<221> NAME/KEY: VARIANT
<222> LOCATION: (252)...(254)
<223> OTHER INFORMATION: Optional Linker

<400> SEQUENCE: 5

```
Ile Ser Cys Gly Ser Pro Pro Ile Leu Asn Gly Arg Ile Ser Tyr
  1               5                  10                  15

Tyr Ser Thr Pro Ile Ala Val Gly Thr Val Ile Arg Tyr Ser Cys Ser
                 20                  25                  30

Gly Thr Phe Arg Leu Ile Gly Glu Lys Ser Leu Leu Cys Ile Thr Lys
             35                  40                  45

Asp Lys Val Asp Gly Thr Trp Asp Lys Pro Ala Pro Lys Cys Glu Tyr
         50                  55                  60

Phe Asn Lys Tyr Ser Ser Cys Pro Glu Pro Ile Val Pro Gly Gly Tyr
 65                  70                  75                  80

Lys Ile Arg Gly Ser Thr Pro Tyr Arg His Gly Asp Ser Val Thr Phe
                 85                  90                  95

Ala Cys Lys Thr Asn Phe Ser Met Asn Gly Asn Lys Ser Val Trp Cys
                100                 105                 110

Gln Ala Asn Asn Met Trp Gly Pro Thr Arg Leu Pro Thr Cys Val Ser
                115                 120                 125

Val Phe Pro Leu Glu Cys Pro Ala Leu Pro Met Ile His Asn Gly His
    130                 135                 140

His Thr Ser Glu Asn Val Gly Ser Ile Ala Pro Gly Leu Ser Val Thr
145                 150                 155                 160

Tyr Ser Cys Glu Ser Gly Tyr Leu Leu Val Gly Lys Ile Ile Asn
                165                 170                 175

Cys Leu Ser Ser Gly Lys Trp Ser Ala Val Pro Pro Thr Cys Glu Glu
                180                 185                 190

Ala Arg Cys Lys Ser Leu Gly Arg Phe Pro Asn Gly Lys Val Lys Glu
                195                 200                 205

Pro Pro Ile Leu Arg Val Gly Val Thr Ala Asn Phe Phe Cys Asp Glu
    210                 215                 220

Gly Tyr Arg Leu Gln Gly Pro Pro Ser Ser Arg Cys Val Ile Ala Gly
225                 230                 235                 240

Gln Gly Val Ala Trp Thr Lys Met Pro Val Cys Xaa Xaa Xaa Cys Val
                245                 250                 255

Ala Glu Asp Cys Asn Glu Leu Pro Pro Arg Arg Asn Thr Glu Ile Leu
                260                 265                 270

Thr Gly Ser Trp Ser Asp Gln Thr Tyr Pro Glu Gly Thr Gln Ala Ile
                275                 280                 285

Tyr Lys Cys Arg Pro Gly Tyr Arg Ser Leu Gly Asn Val Ile Met Val
                290                 295                 300

Cys Arg Lys Gly Glu Trp Val Ala Leu Asn Pro Leu Arg Lys Cys Gln
305                 310                 315                 320

Lys Arg Pro Cys Gly His Pro Gly Asp Thr Pro Phe Gly Thr Phe Thr
                325                 330                 335

Leu Thr Gly Gly Asn Val Phe Glu Tyr Gly Val Lys Ala Val Tyr Thr
                340                 345                 350

Cys Asn Glu Gly Tyr Gln Leu Leu Gly Glu Ile Asn Tyr Arg Glu Cys
                355                 360                 365

Asp Thr Asp Gly Trp Thr Asn Asp Ile Pro Ile Cys Glu Val Val Lys
                370                 375                 380

Cys Leu Pro Val Thr Ala Pro Glu Asn Gly Lys Ile Val Ser Ser Ala
385                 390                 395                 400

Met Glu Pro Asp Arg Glu Tyr His Phe Gly Gln Ala Val Arg Phe Val
                405                 410                 415
```

```
Cys Asn Ser Gly Tyr Lys Ile Glu Gly Asp Glu Met His Cys Ser
            420                 425                 430

Asp Asp Gly Phe Trp Ser Lys Glu Lys Pro Lys Cys Val Glu Ile Ser
            435                 440                 445

Cys Lys Ser Pro Asp Val Ile Asn Gly Ser Pro Ile Ser Gln Lys Ile
            450                 455                 460

Ile Tyr Lys Glu Asn Glu Arg Phe Gln Tyr Lys Cys Asn Met Gly Tyr
465                 470                 475                 480

Glu Tyr Ser Glu Arg Gly Asp Ala Val Cys Thr Glu Ser Gly Trp Arg
                485                 490                 495

Pro Leu Pro Ser Cys Glu Lys Ser Cys Asp Asn Pro Tyr Ile Pro
            500                 505                 510

Asn Gly Asp Tyr Ser Pro Leu Arg Ile Lys His Arg Thr Gly Asp Glu
            515                 520                 525

Ile Thr Tyr Gln Cys Arg Asn Gly Phe Tyr Pro Ala Thr Arg Gly Asn
            530                 535                 540

Thr Ala Lys Cys Thr Ser Thr Gly Trp Ile Pro Ala Pro Arg Cys Thr
545                 550                 555                 560

<210> SEQ ID NO 6
<211> LENGTH: 560
<212> TYPE: PRT
<213> ORGANISM: Murine
<220> FEATURE:
<221> NAME/KEY: VARIANT
<222> LOCATION: 252, 253, 254
<223> OTHER INFORMATION: Xaa = Unknown or Other
<220> FEATURE:
<221> NAME/KEY: VARIANT
<222> LOCATION: (252)...(254)
<223> OTHER INFORMATION: Optional Linker

<400> SEQUENCE: 6

Ile Ser Cys Gly Ser Pro Pro Ile Leu Asn Gly Arg Ile Ser Tyr
1               5                   10                  15

Tyr Ser Thr Pro Ile Ala Val Gly Thr Val Ile Arg Tyr Ser Cys Ser
            20                  25                  30

Gly Thr Phe Arg Leu Ile Gly Glu Lys Ser Leu Leu Cys Ile Thr Lys
            35                  40                  45

Asp Lys Val Asp Gly Thr Trp Asp Lys Pro Ala Pro Lys Cys Glu Tyr
            50                  55                  60

Phe Asn Lys Tyr Ser Ser Cys Pro Glu Pro Ile Val Pro Gly Gly Tyr
65                  70                  75                  80

Lys Ile Arg Gly Ser Thr Pro Tyr Arg His Gly Asp Ser Val Thr Phe
                85                  90                  95

Ala Cys Lys Thr Asn Phe Ser Met Asn Gly Asn Lys Ser Val Trp Cys
            100                 105                 110

Gln Ala Asn Asn Met Trp Gly Pro Thr Arg Leu Pro Thr Cys Val Ser
            115                 120                 125

Val Phe Pro Leu Glu Cys Pro Ala Leu Pro Met Ile His Asn Gly His
            130                 135                 140

His Thr Ser Glu Asn Val Gly Ser Ile Ala Pro Gly Leu Ser Val Thr
145                 150                 155                 160

Tyr Ser Cys Glu Ser Gly Tyr Leu Leu Val Gly Glu Lys Ile Ile Asn
                165                 170                 175

Cys Leu Ser Ser Gly Lys Trp Ser Ala Val Pro Pro Thr Cys Glu Glu
            180                 185                 190
```

Ala Arg Cys Lys Ser Leu Gly Arg Phe Pro Asn Gly Lys Val Lys Glu
            195                 200                 205

Pro Pro Ile Leu Arg Val Gly Val Thr Ala Asn Phe Phe Cys Asp Glu
210                 215                 220

Gly Tyr Arg Leu Gln Gly Pro Pro Ser Ser Arg Cys Val Ile Ala Gly
225                 230                 235                 240

Gln Gly Val Ala Trp Thr Lys Met Pro Val Cys Xaa Xaa Xaa Cys Val
            245                 250                 255

Ala Glu Asp Cys Asn Glu Leu Pro Pro Arg Arg Asn Thr Glu Ile Leu
            260                 265                 270

Thr Gly Ser Trp Ser Asp Gln Thr Tyr Pro Glu Gly Thr Gln Ala Ile
            275                 280                 285

Tyr Lys Cys Arg Pro Gly Tyr Arg Ser Leu Gly Asn Ile Ile Met Val
            290                 295                 300

Cys Arg Lys Gly Glu Trp Val Ala Leu Asn Pro Leu Arg Lys Cys Gln
305                 310                 315                 320

Lys Arg Pro Cys Gly His Pro Gly Asp Thr Pro Phe Gly Thr Phe Thr
            325                 330                 335

Leu Thr Gly Gly Asn Val Phe Glu Tyr Gly Val Lys Ala Val Tyr Thr
            340                 345                 350

Cys Asn Glu Gly Tyr Gln Leu Leu Gly Glu Ile Asn Tyr Arg Glu Cys
            355                 360                 365

Asp Thr Asp Gly Trp Thr Asn Asp Ile Pro Ile Cys Glu Val Val Lys
370                 375                 380

Cys Leu Pro Val Thr Ala Pro Glu Asn Gly Lys Ile Val Ser Ser Ala
385                 390                 395                 400

Met Glu Pro Asp Arg Glu Tyr His Phe Gly Gln Ala Val Arg Phe Val
            405                 410                 415

Cys Asn Ser Gly Tyr Lys Ile Glu Gly Asp Glu Glu Met His Cys Ser
            420                 425                 430

Asp Asp Gly Phe Trp Ser Lys Glu Lys Pro Lys Cys Val Glu Ile Ser
            435                 440                 445

Cys Lys Ser Pro Asp Val Ile Asn Gly Ser Pro Ile Ser Gln Lys Ile
450                 455                 460

Ile Tyr Lys Glu Asn Glu Arg Phe Gln Tyr Lys Cys Asn Met Gly Tyr
465                 470                 475                 480

Glu Tyr Ser Glu Arg Gly Asp Ala Val Cys Thr Glu Ser Gly Trp Arg
            485                 490                 495

Pro Leu Pro Ser Cys Glu Glu Lys Ser Cys Asp Asn Pro Tyr Ile Pro
            500                 505                 510

Asn Gly Asp Tyr Ser Pro Leu Arg Ile Lys His Arg Thr Gly Asp Glu
            515                 520                 525

Ile Thr Tyr Gln Cys Arg Asn Gly Phe Tyr Pro Ala Thr Arg Gly Asn
            530                 535                 540

Thr Ala Lys Cys Thr Ser Thr Gly Trp Ile Pro Ala Pro Arg Cys Thr
545                 550                 555                 560

<210> SEQ ID NO 7
<211> LENGTH: 560
<212> TYPE: PRT
<213> ORGANISM: Murine
<220> FEATURE:
<221> NAME/KEY: VARIANT
<222> LOCATION: 197, 255, 256, 257
<223> OTHER INFORMATION: Xaa = Unknown or Other

```
<220> FEATURE:
<221> NAME/KEY: VARIANT
<222> LOCATION: (255)...(257)
<223> OTHER INFORMATION: Optional Linker

<400> SEQUENCE: 7
```

| | | | | | | | | | | | | | | |
|---|---|---|---|---|---|---|---|---|---|---|---|---|---|---|
| Ile | Ser | Cys | Gly | Ser | Pro | Pro | Ile | Leu | Asn | Gly | Arg | Ile | Ser | Tyr |
| 1 | | | | 5 | | | | | 10 | | | | | 15 |
| Tyr | Ser | Thr | Pro | Ile | Ala | Val | Gly | Thr | Val | Ile | Arg | Tyr | Ser | Cys | Ser |
| | | | 20 | | | | | 25 | | | | | 30 | | |
| Gly | Thr | Phe | Arg | Leu | Ile | Gly | Glu | Lys | Ser | Leu | Leu | Cys | Ile | Thr | Lys |
| | | | 35 | | | | | 40 | | | | | 45 | | |
| Asp | Lys | Val | Asp | Gly | Thr | Trp | Asp | Lys | Pro | Ala | Pro | Lys | Cys | Glu | Tyr |
| 50 | | | | | 55 | | | | | 60 | | | | | |
| Phe | Asn | Lys | Tyr | Ser | Ser | Cys | Pro | Glu | Pro | Ile | Val | Pro | Gly | Gly | Tyr |
| 65 | | | | | 70 | | | | | 75 | | | | | 80 |
| Lys | Ile | Arg | Gly | Ser | Thr | Pro | Tyr | Arg | His | Gly | Asp | Ser | Val | Thr | Phe |
| | | | | 85 | | | | | 90 | | | | | 95 | |
| Ala | Cys | Lys | Thr | Asn | Phe | Ser | Met | Asn | Gly | Asn | Lys | Ser | Val | Trp | Cys |
| | | | 100 | | | | | 105 | | | | | 110 | | |
| Gln | Ala | Asn | Asn | Ile | Asn | Asn | Met | Trp | Gly | Pro | Thr | Arg | Leu | Pro | Thr |
| | | | 115 | | | | | 120 | | | | | 125 | | |
| Cys | Val | Ser | Val | Phe | Pro | Leu | Glu | Cys | Pro | Ala | Leu | Pro | Met | Ile | His |
| 130 | | | | | 135 | | | | | 140 | | | | | |
| Asn | Gly | His | His | Thr | Ser | Glu | Asn | Val | Gly | Ser | Ile | Ala | Pro | Gly | Leu |
| 145 | | | | | 150 | | | | | 155 | | | | | 160 |
| Ser | Val | Thr | Tyr | Ser | Cys | Glu | Ser | Gly | Tyr | Leu | Leu | Val | Gly | Glu | Lys |
| | | | | 165 | | | | | 170 | | | | | 175 | |
| Ile | Ile | Asn | Cys | Leu | Ser | Ser | Gly | Lys | Trp | Ser | Ala | Val | Pro | Pro | Thr |
| | | | 180 | | | | | 185 | | | | | 190 | | |
| Cys | Glu | Glu | Ala | Xaa | Cys | Lys | Ser | Leu | Gly | Arg | Phe | Pro | Asn | Gly | Lys |
| | | | 195 | | | | | 200 | | | | | 205 | | |
| Val | Lys | Glu | Pro | Pro | Ile | Leu | Arg | Val | Gly | Val | Thr | Ala | Asn | Phe | Phe |
| | | 210 | | | | | 215 | | | | | 220 | | | |
| Cys | Asp | Glu | Gly | Tyr | Arg | Leu | Gln | Gly | Pro | Pro | Ser | Ser | Arg | Cys | Val |
| 225 | | | | | 230 | | | | | 235 | | | | | 240 |
| Ile | Ala | Gly | Gln | Gly | Val | Ala | Trp | Thr | Lys | Met | Pro | Val | Cys | Xaa | Xaa |
| | | | | 245 | | | | | 250 | | | | | 255 | |
| Xaa | Glu | Asp | Cys | Asn | Glu | Leu | Pro | Pro | Arg | Arg | Asn | Thr | Glu | Ile | Leu |
| | | | 260 | | | | | 265 | | | | | 270 | | |
| Thr | Gly | Ser | Trp | Ser | Asp | Gln | Thr | Tyr | Pro | Glu | Gly | Thr | Gln | Ala | Ile |
| | | 275 | | | | | 280 | | | | | 285 | | | |
| Tyr | Lys | Cys | Arg | Pro | Gly | Tyr | Arg | Ser | Leu | Gly | Asn | Val | Ile | Met | Val |
| | | 290 | | | | | 295 | | | | | 300 | | | |
| Cys | Arg | Lys | Gly | Glu | Trp | Val | Ala | Leu | Asn | Pro | Leu | Arg | Lys | Cys | Gln |
| 305 | | | | | 310 | | | | | 315 | | | | | 320 |
| Lys | Arg | Pro | Cys | Gly | His | Pro | Gly | Asp | Thr | Pro | Phe | Gly | Thr | Phe | Thr |
| | | | | 325 | | | | | 330 | | | | | 335 | |
| Leu | Thr | Gly | Gly | Asn | Val | Phe | Glu | Tyr | Gly | Val | Lys | Ala | Val | Tyr | Thr |
| | | | 340 | | | | | 345 | | | | | 350 | | |
| Cys | Asn | Glu | Gly | Tyr | Gln | Leu | Leu | Gly | Glu | Ile | Asn | Tyr | Arg | Glu | Cys |
| | | 355 | | | | | 360 | | | | | 365 | | | |
| Asp | Thr | Asp | Gly | Trp | Thr | Asn | Asp | Ile | Pro | Ile | Cys | Glu | Val | Val | Lys |
| | 370 | | | | | 375 | | | | | 380 | | | | |

```
Cys Leu Pro Val Thr Ala Pro Glu Asn Gly Lys Ile Val Ser Ser Ala
385                 390                 395                 400

Met Glu Pro Asp Arg Glu Tyr His Phe Gly Gln Ala Val Arg Phe Val
            405                 410                 415

Cys Asn Ser Gly Tyr Lys Ile Glu Gly Asp Glu Met His Cys Ser
        420                 425                 430

Asp Asp Gly Phe Trp Ser Lys Glu Lys Pro Lys Cys Val Glu Ile Ser
        435                 440                 445

Cys Lys Ser Pro Asp Val Ile Asn Gly Ser Pro Ile Ser Gln Lys Ile
    450                 455                 460

Ile Tyr Lys Glu Asn Glu Arg Phe Gln Tyr Lys Cys Asn Met Gly Tyr
465                 470                 475                 480

Glu Tyr Ser Glu Arg Gly Asp Ala Val Cys Thr Glu Ser Gly Trp Arg
            485                 490                 495

Pro Leu Pro Ser Cys Glu Glu Lys Ser Cys Asp Asn Pro Tyr Ile Pro
        500                 505                 510

Asn Gly Asp Tyr Ser Pro Leu Arg Ile Lys His Arg Thr Gly Asp Glu
        515                 520                 525

Ile Thr Tyr Gln Cys Arg Asn Gly Phe Tyr Pro Ala Thr Arg Gly Asn
530                 535                 540

Thr Ala Lys Cys Thr Ser Thr Gly Trp Ile Pro Ala Pro Arg Cys Thr
545                 550                 555                 560

<210> SEQ ID NO 8
<211> LENGTH: 560
<212> TYPE: PRT
<213> ORGANISM: Murine
<220> FEATURE:
<221> NAME/KEY: VARIANT
<222> LOCATION: 197, 255, 256, 257
<223> OTHER INFORMATION: Xaa = Unknown or Other
<220> FEATURE:
<221> NAME/KEY: VARIANT
<222> LOCATION: (255)...(257)
<223> OTHER INFORMATION: Optional Linker

<400> SEQUENCE: 8

Ile Ser Cys Gly Ser Pro Pro Ile Leu Asn Gly Arg Ile Ser Tyr
1               5                   10                  15

Tyr Ser Thr Pro Ile Ala Val Gly Thr Val Ile Arg Tyr Ser Cys Ser
            20                  25                  30

Gly Thr Phe Arg Leu Ile Gly Glu Lys Ser Leu Leu Cys Ile Thr Lys
        35                  40                  45

Asp Lys Val Asp Gly Thr Trp Asp Lys Pro Ala Pro Lys Cys Glu Tyr
    50                  55                  60

Phe Asn Lys Tyr Ser Ser Cys Pro Glu Pro Ile Val Pro Gly Gly Tyr
65                  70                  75                  80

Lys Ile Arg Gly Ser Thr Pro Tyr Arg His Gly Asp Ser Val Thr Phe
                85                  90                  95

Ala Cys Lys Thr Asn Phe Ser Met Asn Gly Asn Lys Ser Val Trp Cys
            100                 105                 110

Gln Ala Asn Asn Ile Asn Asn Met Trp Gly Pro Thr Arg Leu Pro Thr
        115                 120                 125

Cys Val Ser Val Phe Pro Leu Glu Cys Pro Ala Leu Pro Met Ile His
    130                 135                 140

Asn Gly His His Thr Ser Glu Asn Val Gly Ser Ile Ala Pro Gly Leu
145                 150                 155                 160
```

```
Ser Val Thr Tyr Ser Cys Glu Ser Gly Tyr Leu Leu Val Gly Glu Lys
            165                 170                 175

Ile Ile Asn Cys Leu Ser Ser Gly Lys Trp Ser Ala Val Pro Pro Thr
        180                 185                 190

Cys Glu Glu Ala Xaa Cys Lys Ser Leu Gly Arg Phe Pro Asn Gly Lys
            195                 200                 205

Val Lys Glu Pro Pro Ile Leu Arg Val Gly Val Thr Ala Asn Phe Phe
    210                 215                 220

Cys Asp Glu Gly Tyr Arg Leu Gln Gly Pro Pro Ser Ser Arg Cys Val
225                 230                 235                 240

Ile Ala Gly Gln Gly Val Ala Trp Thr Lys Met Pro Val Cys Xaa Xaa
            245                 250                 255

Xaa Glu Asp Cys Asn Glu Leu Pro Pro Arg Arg Asn Thr Glu Ile Leu
        260                 265                 270

Thr Gly Ser Trp Ser Asp Gln Thr Tyr Pro Glu Gly Thr Gln Ala Ile
        275                 280                 285

Tyr Lys Cys Arg Pro Gly Tyr Arg Ser Leu Gly Asn Ile Ile Met Val
    290                 295                 300

Cys Arg Lys Gly Glu Trp Val Ala Leu Asn Pro Leu Arg Lys Cys Gln
305                 310                 315                 320

Lys Arg Pro Cys Gly His Pro Gly Asp Thr Pro Phe Gly Thr Phe Thr
            325                 330                 335

Leu Thr Gly Gly Asn Val Phe Glu Tyr Gly Val Lys Ala Val Tyr Thr
        340                 345                 350

Cys Asn Glu Gly Tyr Gln Leu Leu Gly Glu Ile Asn Tyr Arg Glu Cys
        355                 360                 365

Asp Thr Asp Gly Trp Thr Asn Asp Ile Pro Ile Cys Glu Val Val Lys
    370                 375                 380

Cys Leu Pro Val Thr Ala Pro Glu Asn Gly Lys Ile Val Ser Ser Ala
385                 390                 395                 400

Met Glu Pro Asp Arg Glu Tyr His Phe Gly Gln Ala Val Arg Phe Val
            405                 410                 415

Cys Asn Ser Gly Tyr Lys Ile Glu Gly Asp Glu Glu Met His Cys Ser
        420                 425                 430

Asp Asp Gly Phe Trp Ser Lys Glu Lys Pro Lys Cys Val Glu Ile Ser
        435                 440                 445

Cys Lys Ser Pro Asp Val Ile Asn Gly Ser Pro Ile Ser Gln Lys Ile
    450                 455                 460

Ile Tyr Lys Glu Asn Glu Arg Phe Gln Tyr Lys Cys Asn Met Gly Tyr
465                 470                 475                 480

Glu Tyr Ser Glu Arg Gly Asp Ala Val Cys Thr Glu Ser Gly Trp Arg
            485                 490                 495

Pro Leu Pro Ser Cys Glu Glu Lys Ser Cys Asp Asn Pro Tyr Ile Pro
        500                 505                 510

Asn Gly Asp Tyr Ser Pro Leu Arg Ile Lys His Arg Thr Gly Asp Glu
        515                 520                 525

Ile Thr Tyr Gln Cys Arg Asn Gly Phe Tyr Pro Ala Thr Arg Gly Asn
    530                 535                 540

Thr Ala Lys Cys Thr Ser Thr Gly Trp Ile Pro Ala Pro Arg Cys Thr
545                 550                 555                 560

<210> SEQ ID NO 9
<211> LENGTH: 557
<212> TYPE: PRT
```

```
<213> ORGANISM: Murine
<220> FEATURE:
<221> NAME/KEY: VARIANT
<222> LOCATION: 252, 253, 254
<223> OTHER INFORMATION: Xaa = Unknown or Other
<220> FEATURE:
<221> NAME/KEY: VARIANT
<222> LOCATION: (252)...(254)
<223> OTHER INFORMATION: Optional Linker

<400> SEQUENCE: 9

Ile Ser Cys Gly Ser Pro Pro Ile Leu Asn Gly Arg Ile Ser Tyr
  1               5                  10                  15

Tyr Ser Thr Pro Ile Ala Val Gly Thr Val Ile Arg Tyr Ser Cys Ser
                 20                  25                  30

Gly Thr Phe Arg Leu Ile Gly Glu Lys Ser Leu Leu Cys Ile Thr Lys
                 35                  40                  45

Asp Lys Val Asp Gly Thr Trp Asp Lys Pro Ala Pro Lys Cys Glu Tyr
 50                  55                  60

Phe Asn Lys Tyr Ser Ser Cys Pro Glu Pro Ile Val Pro Gly Gly Tyr
 65                  70                  75                  80

Lys Ile Arg Gly Ser Thr Pro Tyr Arg His Gly Asp Ser Val Thr Phe
                 85                  90                  95

Ala Cys Lys Thr Asn Phe Ser Met Asn Gly Asn Lys Ser Val Trp Cys
                100                 105                 110

Gln Ala Asn Asn Met Trp Gly Pro Thr Arg Leu Pro Thr Cys Val Ser
                115                 120                 125

Val Phe Pro Leu Glu Cys Pro Ala Leu Pro Met Ile His Asn Gly His
130                 135                 140

His Thr Ser Glu Asn Val Gly Ser Ile Ala Pro Gly Leu Ser Val Thr
145                 150                 155                 160

Tyr Ser Cys Glu Ser Gly Tyr Leu Leu Val Gly Glu Lys Ile Ile Asn
                165                 170                 175

Cys Leu Ser Ser Gly Lys Trp Ser Ala Val Pro Pro Thr Cys Glu Glu
                180                 185                 190

Ala Arg Cys Lys Ser Leu Gly Arg Phe Pro Asn Gly Lys Val Lys Glu
                195                 200                 205

Pro Pro Ile Leu Arg Val Gly Val Thr Ala Asn Phe Phe Cys Asp Glu
210                 215                 220

Gly Tyr Arg Leu Gln Gly Pro Pro Ser Ser Arg Cys Val Ile Ala Gly
225                 230                 235                 240

Gln Gly Val Ala Trp Thr Lys Met Pro Val Cys Xaa Xaa Xaa Glu Asp
                245                 250                 255

Cys Asn Glu Leu Pro Pro Arg Arg Asn Thr Glu Ile Leu Thr Gly Ser
                260                 265                 270

Trp Ser Asp Gln Thr Tyr Pro Glu Gly Thr Gln Ala Ile Tyr Lys Cys
                275                 280                 285

Arg Pro Gly Tyr Arg Ser Leu Gly Asn Val Ile Met Val Cys Arg Lys
                290                 295                 300

Gly Glu Trp Val Ala Leu Asn Pro Leu Arg Lys Cys Gln Lys Arg Pro
305                 310                 315                 320

Cys Gly His Pro Gly Asp Thr Pro Phe Gly Thr Phe Thr Leu Thr Gly
                325                 330                 335

Gly Asn Val Phe Glu Tyr Gly Val Lys Ala Val Tyr Thr Cys Asn Glu
                340                 345                 350

Gly Tyr Gln Leu Leu Gly Glu Ile Asn Tyr Arg Glu Cys Asp Thr Asp
```

-continued

```
                355                 360                 365
Gly Trp Thr Asn Asp Ile Pro Ile Cys Glu Val Val Lys Cys Leu Pro
        370                 375                 380

Val Thr Ala Pro Glu Asn Gly Lys Ile Val Ser Ser Ala Met Glu Pro
385                 390                 395                 400

Asp Arg Glu Tyr His Phe Gly Gln Ala Val Arg Phe Val Cys Asn Ser
                405                 410                 415

Gly Tyr Lys Ile Glu Gly Asp Glu Met His Cys Ser Asp Asp Gly
                    420                 425                 430

Phe Trp Ser Lys Glu Lys Pro Lys Cys Val Glu Ile Ser Cys Lys Ser
            435                 440                 445

Pro Asp Val Ile Asn Gly Ser Pro Ile Ser Gln Lys Ile Ile Tyr Lys
    450                 455                 460

Glu Asn Glu Arg Phe Gln Tyr Lys Cys Asn Met Gly Tyr Glu Tyr Ser
465                 470                 475                 480

Glu Arg Gly Asp Ala Val Cys Thr Glu Ser Gly Trp Arg Pro Leu Pro
                485                 490                 495

Ser Cys Glu Glu Lys Ser Cys Asp Asn Pro Tyr Ile Pro Asn Gly Asp
            500                 505                 510

Tyr Ser Pro Leu Arg Ile Lys His Arg Thr Gly Asp Glu Ile Thr Tyr
    515                 520                 525

Gln Cys Arg Asn Gly Phe Tyr Pro Ala Thr Arg Gly Asn Thr Ala Lys
530                 535                 540

Cys Thr Ser Thr Gly Trp Ile Pro Ala Pro Arg Cys Thr
545                 550                 555
```

```
<210> SEQ ID NO 10
<211> LENGTH: 557
<212> TYPE: PRT
<213> ORGANISM: Murine
<220> FEATURE:
<221> NAME/KEY: VARIANT
<222> LOCATION: 252, 253, 254
<223> OTHER INFORMATION: Xaa = Unknown or Other
<220> FEATURE:
<221> NAME/KEY: VARIANT
<222> LOCATION: (252)...(254)
<223> OTHER INFORMATION: Optional Linker

<400> SEQUENCE: 10
```

```
Ile Ser Cys Gly Ser Pro Pro Ile Leu Asn Gly Arg Ile Ser Tyr
1               5                   10                  15

Tyr Ser Thr Pro Ile Ala Val Gly Thr Val Ile Arg Tyr Ser Cys Ser
                20                  25                  30

Gly Thr Phe Arg Leu Ile Gly Glu Lys Ser Leu Leu Cys Ile Thr Lys
            35                  40                  45

Asp Lys Val Asp Gly Thr Trp Asp Lys Pro Ala Pro Lys Cys Glu Tyr
    50                  55                  60

Phe Asn Lys Tyr Ser Ser Cys Pro Glu Pro Ile Val Pro Gly Gly Tyr
65                  70                  75                  80

Lys Ile Arg Gly Ser Thr Pro Tyr Arg His Gly Asp Ser Val Thr Phe
                85                  90                  95

Ala Cys Lys Thr Asn Phe Ser Met Asn Gly Asn Lys Ser Val Trp Cys
                100                 105                 110

Gln Ala Asn Asn Met Trp Gly Pro Thr Arg Leu Pro Thr Cys Val Ser
            115                 120                 125

Val Phe Pro Leu Glu Cys Pro Ala Leu Pro Met Ile His Asn Gly His
```

-continued

```
            130                 135                 140
His Thr Ser Glu Asn Val Gly Ser Ile Ala Pro Gly Leu Ser Val Thr
145                 150                 155                 160

Tyr Ser Cys Glu Ser Gly Tyr Leu Leu Val Gly Glu Lys Ile Ile Asn
                165                 170                 175

Cys Leu Ser Ser Gly Lys Trp Ser Ala Val Pro Pro Thr Cys Glu Glu
                180                 185                 190

Ala Arg Cys Lys Ser Leu Gly Arg Phe Pro Asn Gly Lys Val Lys Glu
                195                 200                 205

Pro Pro Ile Leu Arg Val Gly Val Thr Ala Asn Phe Phe Cys Asp Glu
210                 215                 220

Gly Tyr Arg Leu Gln Gly Pro Pro Ser Ser Arg Cys Val Ile Ala Gly
225                 230                 235                 240

Gln Gly Val Ala Trp Thr Lys Met Pro Val Cys Xaa Xaa Xaa Glu Asp
                245                 250                 255

Cys Asn Glu Leu Pro Pro Arg Arg Asn Thr Glu Ile Leu Thr Gly Ser
                260                 265                 270

Trp Ser Asp Gln Thr Tyr Pro Glu Gly Thr Gln Ala Ile Tyr Lys Cys
                275                 280                 285

Arg Pro Gly Tyr Arg Ser Leu Gly Asn Ile Ile Met Val Cys Arg Lys
                290                 295                 300

Gly Glu Trp Val Ala Leu Asn Pro Leu Arg Lys Cys Gln Lys Arg Pro
305                 310                 315                 320

Cys Gly His Pro Gly Asp Thr Pro Phe Gly Thr Phe Thr Leu Thr Gly
                325                 330                 335

Gly Asn Val Phe Glu Tyr Gly Val Lys Ala Val Tyr Thr Cys Asn Glu
                340                 345                 350

Gly Tyr Gln Leu Leu Gly Glu Ile Asn Tyr Arg Glu Cys Asp Thr Asp
                355                 360                 365

Gly Trp Thr Asn Asp Ile Pro Ile Cys Glu Val Val Lys Cys Leu Pro
                370                 375                 380

Val Thr Ala Pro Glu Asn Gly Lys Ile Val Ser Ser Ala Met Glu Pro
385                 390                 395                 400

Asp Arg Glu Tyr His Phe Gly Gln Ala Val Arg Phe Val Cys Asn Ser
                405                 410                 415

Gly Tyr Lys Ile Glu Gly Asp Glu Glu Met His Cys Ser Asp Asp Gly
                420                 425                 430

Phe Trp Ser Lys Glu Lys Pro Lys Cys Val Glu Ile Ser Cys Lys Ser
                435                 440                 445

Pro Asp Val Ile Asn Gly Ser Pro Ile Ser Gln Lys Ile Ile Tyr Lys
450                 455                 460

Glu Asn Glu Arg Phe Gln Tyr Lys Cys Asn Met Gly Tyr Glu Tyr Ser
465                 470                 475                 480

Glu Arg Gly Asp Ala Val Cys Thr Glu Ser Gly Trp Arg Pro Leu Pro
                485                 490                 495

Ser Cys Glu Glu Lys Ser Cys Asp Asn Pro Tyr Ile Pro Asn Gly Asp
                500                 505                 510

Tyr Ser Pro Leu Arg Ile Lys His Arg Thr Gly Asp Glu Ile Thr Tyr
                515                 520                 525

Gln Cys Arg Asn Gly Phe Tyr Pro Ala Thr Arg Gly Asn Thr Ala Lys
                530                 535                 540

Cys Thr Ser Thr Gly Trp Ile Pro Ala Pro Arg Cys Thr
545                 550                 555
```

<210> SEQ ID NO 11
<211> LENGTH: 21
<212> TYPE: PRT
<213> ORGANISM: Homo sapiens
<220> FEATURE:
<221> NAME/KEY: VARIANT
<222> LOCATION: (1)...(21)
<223> OTHER INFORMATION: signal peptide

<400> SEQUENCE: 11

Met Pro Met Gly Ser Leu Gln Pro Leu Ala Thr Leu Tyr Leu Leu Gly
 1               5                  10                  15

Met Leu Val Ala Ser
            20

<210> SEQ ID NO 12
<211> LENGTH: 72
<212> TYPE: DNA
<213> ORGANISM: Homo sapiens
<220> FEATURE:
<221> NAME/KEY: misc_feature
<222> LOCATION: (1)...(72)
<223> OTHER INFORMATION: signal peptide

<400> SEQUENCE: 12
atgcccatgg ggtctctgca accgctggcc accttgtacc tgctggggat gctggtcgct     60
tcctgcctcg ga                                                        72

<210> SEQ ID NO 13
<211> LENGTH: 17
<212> TYPE: PRT
<213> ORGANISM: Homo sapiens
<220> FEATURE:
<221> NAME/KEY: VARIANT
<222> LOCATION: (1)...(17)
<223> OTHER INFORMATION: signal peptide

<400> SEQUENCE: 13

Met Gly Ala Ala Gly Leu Leu Gly Val Phe Leu Ala Leu Val Ala Pro
 1               5                  10                  15

Gly

<210> SEQ ID NO 14
<211> LENGTH: 60
<212> TYPE: DNA
<213> ORGANISM: Homo sapiens
<220> FEATURE:
<221> NAME/KEY: misc_feature
<222> LOCATION: (1)...(60)
<223> OTHER INFORMATION: signal peptide

<400> SEQUENCE: 14
atgggcgccg cgggcctgct cggggttttc ttggctctcg tcgcaccggg ggtcctcggg     60

<210> SEQ ID NO 15
<211> LENGTH: 1025
<212> TYPE: PRT
<213> ORGANISM: Mus musculus

<400> SEQUENCE: 15

Met Leu Thr Trp Phe Leu Phe Tyr Phe Ser Glu Ile Ser Cys Asp Pro
 1               5                  10                  15

Pro Pro Glu Val Lys Asn Ala Arg Lys Pro Tyr Tyr Ser Leu Pro Ile
            20                  25                  30

```
Val Pro Gly Thr Val Leu Arg Tyr Thr Cys Ser Pro Ser Tyr Arg Leu
         35                  40                  45

Ile Gly Glu Lys Ala Ile Phe Cys Ile Ser Glu Asn Gln Val His Ala
 50                  55                  60

Thr Trp Asp Lys Ala Pro Ile Cys Glu Ser Val Asn Lys Thr Ile
 65                  70                  75                  80

Ser Cys Ser Asp Pro Ile Val Pro Gly Gly Phe Met Asn Lys Gly Ser
                 85                  90                  95

Lys Ala Pro Phe Arg His Gly Asp Ser Val Thr Phe Thr Cys Lys Ala
                100                 105                 110

Asn Phe Thr Met Lys Gly Ser Lys Thr Val Trp Cys Gln Ala Asn Glu
            115                 120                 125

Met Trp Gly Pro Thr Ala Leu Pro Val Cys Glu Ser Asp Phe Pro Leu
            130                 135                 140

Glu Cys Pro Ser Leu Pro Thr Ile His Asn Gly His His Thr Gly Gln
145                 150                 155                 160

His Val Asp Gln Phe Val Ala Gly Leu Ser Val Thr Tyr Ser Cys Glu
                165                 170                 175

Pro Gly Tyr Leu Leu Thr Gly Lys Lys Thr Ile Lys Cys Leu Ser Ser
                180                 185                 190

Gly Asp Trp Asp Gly Val Ile Pro Thr Cys Lys Glu Ala Gln Cys Glu
            195                 200                 205

His Pro Gly Lys Phe Pro Asn Gly Gln Val Lys Glu Pro Leu Ser Leu
            210                 215                 220

Gln Val Gly Thr Thr Val Tyr Phe Ser Cys Asn Glu Gly Tyr Gln Leu
225                 230                 235                 240

Gln Gly Gln Pro Ser Ser Gln Cys Val Ile Val Glu Gln Lys Ala Ile
                245                 250                 255

Trp Thr Lys Lys Pro Val Cys Lys Glu Ile Leu Cys Pro Pro Pro Pro
            260                 265                 270

Pro Val Arg Asn Gly Ser His Thr Gly Ser Phe Ser Glu Asn Val Pro
            275                 280                 285

Tyr Gly Ser Thr Val Thr Tyr Thr Cys Asp Pro Ser Pro Glu Lys Gly
            290                 295                 300

Val Ser Phe Thr Leu Ile Gly Glu Lys Thr Ile Asn Cys Thr Thr Gly
305                 310                 315                 320

Ser Gln Lys Thr Gly Ile Trp Ser Gly Pro Ala Pro Tyr Cys Val Leu
                325                 330                 335

Ser Thr Ser Ala Val Leu Cys Leu Gln Pro Lys Ile Lys Arg Gly Gln
            340                 345                 350

Ile Leu Ser Ile Leu Lys Asp Ser Tyr Ser Tyr Asn Asp Thr Val Ala
            355                 360                 365

Phe Ser Cys Glu Pro Gly Phe Thr Leu Lys Gly Asn Arg Ser Ile Arg
            370                 375                 380

Cys Asn Ala His Gly Thr Trp Glu Pro Pro Val Pro Val Cys Glu Lys
385                 390                 395                 400

Gly Cys Gln Ala Pro Lys Ile Ile Asn Gly Gln Lys Glu Asp Ser
                405                 410                 415

Tyr Leu Leu Asn Phe Asp Pro Gly Thr Ser Ile Arg Tyr Ser Cys Asp
                420                 425                 430

Pro Gly Tyr Leu Leu Val Gly Glu Asp Thr Ile His Cys Thr Pro Glu
            435                 440                 445
```

```
Gly Lys Trp Thr Pro Ile Thr Pro Gln Cys Thr Val Ala Glu Cys Lys
    450                 455                 460

Pro Val Gly Pro His Leu Phe Lys Arg Pro Gln Asn Gln Phe Ile Arg
465                 470                 475                 480

Thr Ala Val Asn Ser Ser Cys Asp Glu Gly Phe Gln Leu Ser Glu Ser
                485                 490                 495

Ala Tyr Gln Leu Cys Gln Gly Thr Ile Pro Trp Phe Ile Glu Ile Arg
            500                 505                 510

Leu Cys Lys Glu Ile Thr Cys Pro Pro Pro Val Ile His Asn Gly
        515                 520                 525

Thr His Thr Trp Ser Ser Glu Asp Val Pro Tyr Gly Thr Val Val
    530                 535                 540

Thr Tyr Met Cys Tyr Pro Gly Pro Glu Glu Gly Val Lys Phe Lys Leu
545                 550                 555                 560

Ile Gly Glu Gln Thr Ile His Cys Thr Ser Asp Ser Arg Gly Arg Gly
                565                 570                 575

Ser Trp Ser Ser Pro Ala Pro Leu Cys Lys Leu Ser Leu Pro Ala Val
            580                 585                 590

Gln Cys Thr Asp Val His Val Glu Asn Gly Val Lys Leu Thr Asp Asn
        595                 600                 605

Lys Ala Pro Tyr Phe Tyr Asn Asp Ser Val Met Phe Lys Cys Asp Asp
    610                 615                 620

Gly Tyr Ile Leu Ser Gly Ser Ser Gln Ile Arg Cys Lys Ala Asn Asn
625                 630                 635                 640

Thr Trp Asp Pro Glu Lys Pro Leu Cys Lys Lys Glu Gly Cys Glu Pro
                645                 650                 655

Met Arg Val His Gly Leu Pro Asp Asp Ser His Ile Lys Leu Val Lys
            660                 665                 670

Arg Thr Cys Gln Asn Gly Tyr Gln Leu Thr Gly Tyr Thr Tyr Glu Lys
        675                 680                 685

Cys Gln Asn Ala Glu Asn Gly Thr Trp Phe Lys Lys Ile Glu Val Cys
    690                 695                 700

Thr Val Ile Leu Cys Gln Pro Pro Lys Ile Ala Asn Gly Gly His
705                 710                 715                 720

Thr Gly Met Met Ala Lys His Phe Leu Tyr Gly Asn Glu Val Ser Tyr
                725                 730                 735

Glu Cys Asp Glu Gly Phe Tyr Leu Leu Gly Glu Lys Ser Leu Gln Cys
            740                 745                 750

Val Asn Asp Ser Lys Gly His Gly Ser Trp Ser Gly Pro Pro Pro Gln
        755                 760                 765

Cys Leu Gln Ser Ser Pro Leu Thr His Cys Pro Asp Pro Glu Val Lys
    770                 775                 780

His Gly Tyr Lys Leu Asn Lys Thr His Ser Ala Phe Ser His Asn Asp
785                 790                 795                 800

Ile Val His Phe Val Cys Asn Gln Gly Phe Ile Met Asn Gly Ser His
                805                 810                 815

Leu Ile Arg Cys His Thr Asn Asn Thr Trp Leu Pro Gly Val Pro Thr
            820                 825                 830

Cys Ile Arg Lys Ala Ser Leu Gly Cys Gln Ser Pro Ser Thr Ile Pro
        835                 840                 845

Asn Gly Asn His Thr Gly Gly Ser Ile Ala Arg Phe Pro Pro Gly Met
    850                 855                 860

Ser Val Met Tyr Ser Cys Tyr Gln Gly Phe Leu Met Ala Gly Glu Ala
```

```
                865                 870                 875                 880
Arg Leu Ile Cys Thr His Glu Gly Thr Trp Ser Gln Pro Pro Phe
                885                 890                 895
Cys Lys Glu Val Asn Cys Ser Phe Pro Glu Asp Thr Asn Gly Ile Gln
                900                 905                 910
Lys Gly Phe Gln Pro Gly Lys Thr Tyr Arg Phe Gly Ala Thr Val Thr
                915                 920                 925
Leu Glu Cys Glu Asp Gly Tyr Thr Leu Glu Gly Ser Pro Gln Ser Gln
                930                 935                 940
Cys Gln Asp Asp Ser Gln Trp Asn Pro Leu Ala Leu Cys Lys Tyr
945                 950                 955                 960
Arg Arg Trp Ser Thr Ile Pro Leu Ile Cys Gly Ile Ser Val Gly Ser
                965                 970                 975
Ala Leu Ile Ile Leu Met Ser Val Gly Phe Cys Met Ile Leu Lys His
                980                 985                 990
Arg Glu Ser Asn Tyr Tyr Thr Lys Thr Arg Pro Lys Glu Gly Ala Leu
                995                 1000                1005
His Leu Glu Thr Arg Glu Val Tyr Ser Ile Asp Pro Tyr Asn Pro Ala
                1010                1015                1020
Ser
1025

<210> SEQ ID NO 16
<211> LENGTH: 1249
<212> TYPE: PRT
<213> ORGANISM: Mus musculus

<400> SEQUENCE: 16

Met Arg Leu Ser Ala Arg Ile Ile Trp Leu Ile Leu Trp Thr Val Cys
1               5                   10                  15
Ala Ala Glu Asp Cys Lys Gly Pro Pro Pro Arg Glu Asn Ser Glu Ile
                20                  25                  30
Leu Ser Gly Ser Trp Ser Glu Gln Leu Tyr Pro Glu Gly Thr Gln Ala
                35                  40                  45
Thr Tyr Lys Cys Arg Pro Gly Tyr Arg Thr Leu Gly Thr Ile Val Lys
                50                  55                  60
Val Cys Lys Asn Gly Lys Trp Val Ala Ser Asn Pro Ser Arg Ile Cys
65                  70                  75                  80
Arg Lys Lys Pro Cys Gly His Pro Gly Asp Thr Pro Phe Gly Ser Phe
                85                  90                  95
Arg Leu Ala Val Gly Ser Gln Phe Glu Phe Gly Ala Lys Val Val Tyr
                100                 105                 110
Thr Cys Asp Asp Gly Tyr Gln Leu Leu Gly Glu Ile Asp Tyr Arg Glu
                115                 120                 125
Cys Gly Ala Asp Gly Trp Ile Asn Asp Ile Pro Leu Cys Glu Val Val
                130                 135                 140
Lys Cys Leu Pro Val Thr Glu Leu Glu Asn Gly Arg Ile Val Ser Gly
145                 150                 155                 160
Ala Ala Glu Thr Asp Gln Glu Tyr Tyr Phe Gly Gln Val Val Arg Phe
                165                 170                 175
Glu Cys Asn Ser Gly Phe Lys Ile Glu Gly His Lys Glu Ile His Cys
                180                 185                 190
Ser Glu Asn Gly Leu Trp Ser Asn Glu Lys Pro Arg Cys Val Glu Ile
                195                 200                 205
```

```
Leu Cys Thr Pro Pro Arg Val Glu Asn Gly Asp Gly Ile Asn Val Lys
    210                 215                 220
Pro Val Tyr Lys Glu Asn Glu Arg Tyr His Tyr Lys Cys Lys His Gly
225                 230                 235                 240
Tyr Val Pro Lys Glu Arg Gly Asp Ala Val Cys Thr Gly Ser Gly Trp
                245                 250                 255
Ser Ser Gln Pro Phe Cys Glu Glu Lys Arg Cys Ser Pro Pro Tyr Ile
            260                 265                 270
Leu Asn Gly Ile Tyr Thr Pro His Arg Ile Ile His Arg Ser Asp Asp
        275                 280                 285
Glu Ile Arg Tyr Glu Cys Asn Tyr Gly Phe Tyr Pro Val Thr Gly Ser
    290                 295                 300
Thr Val Ser Lys Cys Thr Pro Thr Gly Trp Ile Pro Val Pro Arg Cys
305                 310                 315                 320
Thr Leu Lys Pro Cys Glu Phe Pro Gln Phe Lys Tyr Gly Arg Leu Tyr
                325                 330                 335
Tyr Glu Glu Ser Leu Arg Pro Asn Phe Pro Val Ser Ile Gly Asn Lys
            340                 345                 350
Tyr Ser Tyr Lys Cys Asp Asn Gly Phe Ser Pro Pro Ser Gly Tyr Ser
        355                 360                 365
Trp Asp Tyr Leu Arg Cys Thr Ala Gln Gly Trp Glu Pro Glu Val Pro
    370                 375                 380
Cys Val Arg Lys Cys Val Phe His Tyr Val Glu Asn Gly Asp Ser Ala
385                 390                 395                 400
Tyr Trp Glu Lys Val Tyr Val Gln Gly Gln Ser Leu Lys Val Gln Cys
                405                 410                 415
Tyr Asn Gly Tyr Ser Leu Gln Asn Gly Gln Asp Thr Met Thr Cys Thr
            420                 425                 430
Glu Asn Gly Trp Ser Pro Pro Pro Lys Cys Ile Arg Ile Lys Thr Cys
        435                 440                 445
Ser Ala Ser Asp Ile His Ile Asp Asn Gly Phe Leu Ser Glu Ser Ser
    450                 455                 460
Ser Ile Tyr Ala Leu Asn Arg Glu Thr Ser Tyr Arg Cys Lys Gln Gly
465                 470                 475                 480
Tyr Val Thr Asn Thr Gly Glu Ile Ser Gly Ser Ile Thr Cys Leu Gln
                485                 490                 495
Asn Gly Trp Ser Pro Gln Pro Ser Cys Ile Lys Ser Cys Asp Met Pro
            500                 505                 510
Val Phe Glu Asn Ser Ile Thr Lys Asn Thr Arg Thr Trp Phe Lys Leu
        515                 520                 525
Asn Asp Lys Leu Asp Tyr Glu Cys Leu Val Gly Phe Glu Asn Glu Tyr
    530                 535                 540
Lys His Thr Lys Gly Ser Ile Thr Cys Thr Tyr Tyr Gly Trp Ser Asp
545                 550                 555                 560
Thr Pro Ser Cys Tyr Glu Arg Glu Cys Ser Val Pro Thr Leu Asp Arg
                565                 570                 575
Lys Leu Val Val Ser Pro Arg Lys Lys Tyr Arg Val Gly Asp Leu
            580                 585                 590
Leu Glu Phe Ser Cys His Ser Gly His Arg Val Gly Pro Asp Ser Val
        595                 600                 605
Gln Cys Tyr His Phe Gly Trp Ser Pro Gly Phe Pro Thr Cys Lys Gly
    610                 615                 620
Gln Val Ala Ser Cys Ala Pro Pro Leu Glu Ile Leu Asn Gly Glu Ile
```

-continued

```
                625                 630                 635                 640
Asn Gly Ala Lys Lys Val Glu Tyr Ser His Gly Glu Val Val Lys Tyr
                    645                 650                 655
Asp Cys Lys Pro Arg Phe Leu Leu Lys Gly Pro Asn Lys Ile Gln Cys
                    660                 665                 670
Val Asp Gly Asn Trp Thr Thr Leu Pro Val Cys Ile Glu Glu Glu Arg
                675                 680                 685
Thr Cys Gly Asp Ile Pro Glu Leu Glu His Gly Ser Ala Lys Cys Ser
                690                 695                 700
Val Pro Pro Tyr His His Gly Asp Ser Val Glu Phe Ile Cys Glu Glu
705                 710                 715                 720
Asn Phe Thr Met Ile Gly His Gly Ser Val Ser Cys Ile Ser Gly Lys
                    725                 730                 735
Trp Thr Gln Leu Pro Lys Cys Val Ala Thr Asp Gln Leu Glu Lys Cys
                    740                 745                 750
Arg Val Leu Lys Ser Thr Gly Ile Glu Ala Ile Lys Pro Lys Leu Thr
                    755                 760                 765
Glu Phe Thr His Asn Ser Thr Met Asp Tyr Lys Cys Arg Asp Lys Gln
                770                 775                 780
Glu Tyr Glu Arg Ser Ile Cys Ile Asn Gly Lys Trp Asp Pro Glu Pro
785                 790                 795                 800
Asn Cys Thr Ser Lys Thr Ser Cys Pro Pro Pro Gln Ile Pro Asn
                    805                 810                 815
Thr Gln Val Ile Glu Thr Thr Val Lys Tyr Leu Asp Gly Glu Lys Leu
                    820                 825                 830
Ser Val Leu Cys Gln Asp Asn Tyr Leu Thr Gln Asp Ser Glu Glu Met
                    835                 840                 845
Val Cys Lys Asp Gly Arg Trp Gln Ser Leu Pro Arg Cys Ile Glu Lys
                850                 855                 860
Ile Pro Cys Ser Gln Pro Pro Thr Ile Glu His Gly Ser Ile Asn Leu
865                 870                 875                 880
Pro Arg Ser Ser Glu Glu Arg Arg Asp Ser Ile Glu Ser Ser Ser His
                    885                 890                 895
Glu His Gly Thr Thr Phe Ser Tyr Val Cys Asp Asp Gly Phe Arg Ile
                    900                 905                 910
Pro Glu Glu Asn Arg Ile Thr Cys Tyr Met Gly Lys Trp Ser Thr Pro
                915                 920                 925
Pro Arg Cys Val Gly Leu Pro Cys Gly Pro Pro Ser Ile Pro Leu
                930                 935                 940
Gly Thr Val Ser Leu Glu Leu Glu Ser Tyr Gln His Gly Glu Glu Val
945                 950                 955                 960
Thr Tyr His Cys Ser Thr Gly Phe Gly Ile Asp Gly Pro Ala Phe Ile
                    965                 970                 975
Ile Cys Glu Gly Gly Lys Trp Ser Asp Pro Pro Lys Cys Ile Lys Thr
                    980                 985                 990
Asp Cys Asp Val Leu Pro Thr Val Lys Asn Ala Ile Ile Arg Gly Lys
                    995                 1000                1005
Ser Lys Lys Ser Tyr Arg Thr Gly Glu Gln Val Thr Phe Arg Cys Gln
                1010                1015                1020
Ser Pro Tyr Gln Met Asn Gly Ser Asp Thr Val Thr Cys Val Asn Ser
                1025                1030                1035                1040
Arg Trp Ile Gly Gln Pro Val Cys Lys Asp Asn Ser Cys Val Asp Pro
                    1045                1050                1055
```

```
Pro His Val Pro Asn Ala Thr Ile Val Thr Arg Thr Lys Asn Lys Tyr
        1060                1065                1070

Leu His Gly Asp Arg Val Arg Tyr Glu Cys Asn Lys Pro Leu Glu Leu
        1075                1080                1085

Phe Gly Gln Val Glu Val Met Cys Glu Asn Gly Ile Trp Thr Glu Lys
        1090                1095                1100

Pro Lys Cys Arg Gly Leu Phe Asp Leu Ser Leu Lys Pro Ser Asn Val
1105                1110                1115                1120

Phe Ser Leu Asp Ser Thr Gly Lys Cys Gly Pro Pro Pro Ile Asp
                1125                1130                1135

Asn Gly Asp Ile Thr Ser Leu Ser Leu Pro Val Tyr Glu Pro Leu Ser
        1140                1145                1150

Ser Val Glu Tyr Gln Cys Gln Lys Tyr Leu Leu Lys Gly Lys Lys
        1155                1160                1165

Thr Ile Thr Cys Thr Asn Gly Lys Trp Ser Glu Pro Pro Thr Cys Leu
        1170                1175                1180

His Ala Cys Val Ile Pro Glu Asn Ile Met Glu Ser His Asn Ile Ile
1185                1190                1195                1200

Leu Lys Trp Arg His Thr Glu Lys Ile Tyr Ser His Ser Gly Glu Asp
        1205                1210                1215

Ile Glu Phe Gly Cys Lys Tyr Gly Tyr Tyr Lys Ala Arg Asp Ser Pro
        1220                1225                1230

Pro Phe Arg Thr Lys Cys Ile Asn Gly Thr Ile Asn Tyr Pro Thr Cys
        1235                1240                1245

Val

<210> SEQ ID NO 17
<211> LENGTH: 559
<212> TYPE: PRT
<213> ORGANISM: Mus musculus

<400> SEQUENCE: 17

Ile Ser Cys Asp Pro Pro Glu Val Lys Asn Ala Arg Lys Pro Tyr
1                5                  10                  15

Tyr Ser Leu Pro Ile Val Pro Gly Thr Val Leu Arg Tyr Thr Cys Ser
            20                  25                  30

Pro Ser Tyr Arg Leu Ile Gly Glu Lys Ala Ile Phe Cys Ile Ser Glu
        35                  40                  45

Asn Gln Val His Ala Thr Trp Asp Lys Ala Pro Ile Cys Glu Ser
    50                  55                  60

Val Asn Lys Thr Ile Ser Cys Ser Asp Pro Ile Val Pro Gly Gly Phe
65                  70                  75                  80

Met Asn Lys Gly Ser Lys Ala Pro Phe Arg His Gly Asp Ser Val Thr
                85                  90                  95

Phe Thr Cys Lys Ala Asn Phe Thr Met Lys Gly Ser Lys Thr Val Trp
            100                 105                 110

Cys Gln Ala Asn Glu Met Trp Gly Pro Thr Ala Leu Pro Val Cys Glu
        115                 120                 125

Ser Asp Phe Pro Leu Glu Cys Pro Ser Leu Pro Thr Ile His Asn Gly
    130                 135                 140

His His Thr Gly Gln His Val Asp Gln Phe Val Ala Gly Leu Ser Val
145                 150                 155                 160

Thr Tyr Ser Cys Glu Pro Gly Tyr Leu Leu Thr Gly Lys Lys Thr Ile
                165                 170                 175
```

Lys Cys Leu Ser Ser Gly Asp Trp Asp Gly Val Ile Pro Thr Cys Lys
            180                 185                 190

Glu Ala Gln Cys Glu His Pro Gly Lys Phe Pro Asn Gly Gln Val Lys
            195                 200                 205

Glu Pro Leu Ser Leu Gln Val Gly Thr Thr Val Tyr Phe Ser Cys Asn
            210                 215                 220

Glu Gly Tyr Gln Leu Gln Gly Gln Pro Ser Ser Gln Cys Val Ile Val
225                 230                 235                 240

Glu Gln Lys Ala Ile Trp Thr Lys Lys Pro Val Cys Lys Glu Ile Leu
            245                 250                 255

Glu Asp Cys Lys Gly Pro Pro Arg Glu Asn Ser Glu Ile Leu Ser
            260                 265                 270

Gly Ser Trp Ser Glu Gln Leu Tyr Pro Glu Gly Thr Gln Ala Thr Tyr
            275                 280                 285

Lys Cys Arg Pro Gly Tyr Arg Thr Leu Gly Thr Ile Val Lys Val Cys
            290                 295                 300

Lys Asn Gly Lys Trp Val Ala Ser Asn Pro Ser Arg Ile Cys Arg Lys
305                 310                 315                 320

Lys Pro Cys Gly His Pro Gly Asp Thr Pro Phe Gly Ser Phe Arg Leu
            325                 330                 335

Ala Val Gly Ser Gln Phe Glu Phe Gly Ala Lys Val Val Tyr Thr Cys
            340                 345                 350

Asp Asp Gly Tyr Gln Leu Leu Gly Glu Ile Asp Tyr Arg Glu Cys Gly
            355                 360                 365

Ala Asp Gly Trp Ile Asn Asp Ile Pro Leu Cys Glu Val Val Lys Cys
            370                 375                 380

Leu Pro Val Thr Glu Leu Glu Asn Gly Arg Ile Val Ser Gly Ala Ala
385                 390                 395                 400

Glu Thr Asp Gln Glu Tyr Tyr Phe Gly Gln Val Val Arg Phe Glu Cys
            405                 410                 415

Asn Ser Gly Phe Lys Ile Glu Gly His Lys Glu Ile His Cys Ser Glu
            420                 425                 430

Asn Gly Leu Trp Ser Asn Glu Lys Pro Arg Cys Val Glu Ile Leu Cys
            435                 440                 445

Thr Pro Pro Arg Val Glu Asn Gly Asp Gly Ile Asn Val Lys Pro Val
            450                 455                 460

Tyr Lys Glu Asn Glu Arg Tyr His Tyr Lys Cys Lys His Gly Tyr Val
465                 470                 475                 480

Pro Lys Glu Arg Gly Asp Ala Val Cys Thr Gly Ser Gly Trp Ser Ser
            485                 490                 495

Gln Pro Phe Cys Glu Glu Lys Arg Cys Ser Pro Tyr Ile Leu Asn
            500                 505                 510

Gly Ile Tyr Thr Pro His Arg Ile Ile His Arg Ser Asp Asp Glu Ile
            515                 520                 525

Arg Tyr Glu Cys Asn Tyr Gly Phe Tyr Pro Val Thr Gly Ser Thr Val
            530                 535                 540

Ser Lys Cys Thr Pro Thr Gly Trp Ile Pro Val Pro Arg Cys Thr
545                 550                 555

<210> SEQ ID NO 18
<211> LENGTH: 1750
<212> TYPE: DNA
<213> ORGANISM: Mus musculus

<400> SEQUENCE: 18

```
atgcccatgg ggtctctgca accgctggcc accttgtacc tgctggggat gctggtcgct      60
tccgtgctag cgatttcttg tgaccctcct cctgaagtca aaaatgctcg gaaaccctat     120
tattctcttc ccatagttcc tggaactgtt ctgaggtaca cttgttcacc tagctaccgc     180
ctcattggag aaaaggctat cttttgtata agtgaaaatc aagtgcatgc cacctgggat     240
aaagctcctc ctatatgtga atctgtgaat aaaaccattt cttgctcaga tcccatagta     300
ccagggggat tcatgaataa aggatctaag gcaccattca gacatggtga ttctgtgaca     360
tttacctgta aagccaactt caccatgaaa ggaagcaaaa ctgtctggtg ccaggcaaat     420
gaaatgtggg gaccaacagc tctgccagtc tgtgagagtg atttccctct ggagtgccca     480
tcacttccaa cgattcataa tggacaccac acaggacagc atgttgacca gtttgttgcg     540
gggttgtctg tgacatacag ttgtgaacct ggctatttgc tcactggaaa aagacaatt     600
aagtgcttat cttcaggaga ctgggatggt gtcatcccga catgcaaaga ggcccagtgt     660
gaacatccag gaaagtttcc caatgggcag gtaaaggaac ctctgagcct tcaggttggc     720
acaactgtgt acttctcctg taatgaaggg taccaattac aaggacaacc ctctagtcag     780
tgtgtaattg ttgaacagaa agccatctgg actaagaagc agtatgtaa agaaattctc     840
gaagattgta aggtcctcc tccaagagaa aattcagaaa ttctctcagg ctcgtggtca     900
gaacaactat atccagaagg cacccaggct acctacaaat gccgccctgg ataccgaaca     960
cttggcacta ttgtaaaagt atgcaagaat ggaaaatggg tggcgtctaa cccatccagg    1020
atatgtcgga aaaagccttg tgggcatccc ggagacacac cctttgggtc ctttaggctg    1080
gcagttggat ctcaatttga gtttggtgca aaggttgttt atacctgtga tgatgggtat    1140
caactattag gtgaaattga ttaccgtgaa tgtggtgcag atggctggat caatgatatt    1200
ccactatgtg aagttgtgaa gtgtctacct gtgacagaac tcgagaatgg aagaattgtg    1260
agtggtgcag cagaaacaga ccaggaatac tattttggac aggtggtgcg gtttgaatgc    1320
aattcaggct tcaagattga aggacataag gaaattcatt gctcagaaaa tggcctttgg    1380
agcaatgaaa agccacgatg tgtggaaatt ctctgcacac caccgcgagt ggaaaatgga    1440
gatggtataa atgtgaaacc agtttacaag gagaatgaaa gataccacta taagtgtaag    1500
catggttatg tgcccaaaga aagaggggat gccgtctgca caggctctgg atggagttct    1560
cagcctttct gtgaagaaaa gagatgctca cctccttata ttctaaatgg tatctacaca    1620
cctcacagga ttatacacag aagtgatgat gaaatcagat atgaatgtaa ttatggcttc    1680
tatcctgtaa ctggatcaac tgtttcaaag tgtacaccca ctggctggat ccctgttcca    1740
agatgtacct                                                             1750
```

<210> SEQ ID NO 19
<211> LENGTH: 2676
<212> TYPE: DNA
<213> ORGANISM: Mus musculus

<400> SEQUENCE: 19

```
gaattcgccg ccaccatgcc catggggtct ctgcaaccgc tggccacctt gtacctgctg      60
ggatgctgg tcgcttccgt gctagcgatt tcttgtgacc ctcctcctga agtcaaaaat     120
gctcggaaac cctattattc tcttcccata gttcctggaa ctgttctgag gtacacttgt     180
tcacctagct accgcctcat tggagaaaag gctatctttt gtataagtga aaatcaagtg     240
catgccacct gggataaagc tcctcctata tgtgaatctg tgaataaaac catttcttgc     300
```

```
tcagatccca tagtaccagg gggattcatg aataaaggat ctaaggcacc attcagacat    360
ggtgattctg tgacatttac ctgtaaagcc aacttcacca tgaaaggaag caaaactgtc    420
tggtgccagg caaatgaaat gtggggacca acagctctgc cagtctgtga gagtgatttc    480
cctctggagt gcccatcact tccaacgatt cataatggac accacacagg acagcatgtt    540
gaccagtttg ttgcggggtt gtctgtgaca tacagttgtg aacctggcta tttgctcact    600
ggaaaaaaga caattaagtg cttatcttca ggagactggg atggtgtcat cccgacatgc    660
aaagaggccc agtgtgaaca tccaggaaag tttcccaatg gcaggtaaa ggaacctctg    720 agccttcagg ttggcacaac tgtgtacttc tcctgtaatg aagggtacca attacaagga    780
caaccctcta gtcagtgtgt aattgttgaa cagaaagcca tctggactaa gaagccagta    840
tgtaaagaaa ttctcgaaga ttgtaaaggt cctcctccaa gagaaaattc agaaattctc    900
tcaggctcgt ggtcagaaca actatatcca gaaggcaccc aggctaccta caatgccgc    960 cctggatacc gaacacttgg cactattgta aagtatgca agaatggaaa atgggtggcg   1020
tctaacccat ccaggatatg tcggaaaaag ccttgtgggc atcccggaga cacccctttt   1080
gggtccttta ggctggcagt tggatctcaa tttgagtttg gtgcaaaggt tgtttatacc   1140
tgtgatgatg gtatcaact attaggtgaa attgattacc gtgaatgtgg tgcagatggc   1200
tggatcaatg atattccact atgtgaagtt gtgaagtgtc tacctgtgac agaactcgag   1260 aatgaagaa ttgtgagtgg tgcagcagaa acagaccagg aatactatt tggacaggtg   1320 gtgcggtttg aatgcaattc aggcttcaag attgaaggac ataaggaaat tcattgctca   1380
gaaaatggcc tttggagcaa tgaaaagcca cgatgtgtgg aaattctctg cacaccaccg   1440
cgagtggaaa atggagatgg tataaatgtg aaaccagttt acaaggagaa tgaaagatac   1500
cactataagt gtaagcatgg ttatgtgccc aaagaaagag gggatgccgt ctgcacaggc   1560
tctggatgga gttctcagcc tttctgtgaa gaaaagagat gctcacctcc ttatattcta   1620
aatggtatct acacacctca caggattata cacagaagtg atgatgaaat cagatatgaa   1680
tgtaattatg gcttctatcc tgtaactgga tcaactgttt caaagtgtac acccactggc   1740
tggatccctg ttccaagatg taccgaagat tgtaaaggtc ctcctccaag agaaaattca   1800
gaaattctct caggctcgtg gtcagaacaa ctatatccag aaggcaccca ggctacctac   1860
aaatgccgcc ctggataccg aacacttggc actattgtaa agtatgcaa gaatggaaaa   1920 tgggtggcgt ctaacccatc caggatatgt cggaaaaagc cttgtgggca tcccggagac   1980 acccctttg gtcctttag ctggcagtt ggatctcaat ttgagtttgg tgcaaaggtt   2040
gtttatacct gtgatgatgg tatcaacta ttaggtgaaa ttgattaccg tgaatgtggt   2100
gcagatggct ggatcaatga tattccacta tgtgaagttg tgaagtgtct acctgtgaca   2160
gaactcgaga atggaagaat tgtgagtggt gcagcagaaa cagaccagga atactatttt   2220
ggacaggtgg tgcggtttga atgcaattca ggcttcaaga ttgaaggaca taaggaaatt   2280
cattgctcag aaaatggcct ttggagcaat gaaaagccac gatgtgtgga attctctgc   2340 acaccaccgc gagtggaaaa tggagatggt ataaatgtga aaccagttta caaggagaat   2400
gaaagatacc actataagtg taagcatggt tatgtgccca aagaaagagg ggatgccgtc   2460
tgcacaggct ctggatggag ttctcagcct ttctgtgaag aaaagagatg ctcacctcct   2520
tatattctaa atggtatcta cacacctcac aggattatac acagaagtga tgatgaaatc   2580
agatatgaat gtaattatgg cttctatcct gtaactggat caactgtttc aaagtgtaca   2640
```

```
cccactggct ggatccctgt tccaagatgt acctaa                              2676
```

<210> SEQ ID NO 20
<211> LENGTH: 2706
<212> TYPE: DNA
<213> ORGANISM: Mus musculus

<400> SEQUENCE: 20

```
gaattcgccg ccaccatgcc catggggtct ctgcaaccgc tggccacctt gtacctgctg     60
gggatgctgg tcgcttccgt gctagcgatt tcttgtgacc ctcctcctga agtcaaaaat    120
gctcggaaac cctattattc tcttcccata gttcctggaa ctgttctgag gtacacttgt    180
tcacctagct accgcctcat tggagaaaag gctatctttt gtataagtga aaatcaagtg    240
catgccacct gggataaagc tcctcctata tgtgaatctg tgaataaaac catttcttgc    300
tcagatccca tagtaccagg gggattcatg aataaaggat ctaaggcacc attcagacat    360
ggtgattctg tgacatttac ctgtaaagcc aacttcacca tgaaaggaag caaaactgtc    420
tggtgccagg caaatgaaat gtggggacca acagctctgc cagtctgtga gagtgatttc    480
cctctggagt gcccatcact tccaacgatt cataatggac accacacagg acagcatgtt    540
gaccagtttg ttgcggggtt gtctgtgaca tacagttgtg aacctggcta tttgctcact    600
ggaaaaaaga caattaagtg cttatcttca ggagactggg atggtgtcat cccgacatgc    660
aaagaggccc agtgtgaaca tccaggaaag tttcccaatg ggcaggtaaa ggaacctctg    720
agccttcagg ttggcacaac tgtgtacttc tcctgtaatg aagggtacca attacaagga    780
caaccctcta gtcagtgtgt aattgttgaa cagaaagcca tctggactaa gagccagta    840
tgtaaagaaa ttctcggcgg aggtgggtcg ggtggcggcg gatctgaaga ttgtaaaggt    900
cctcctccaa gagaaaattc agaaattctc tcaggctcgt ggtcagaaca actatatcca    960
gaaggcaccc aggctaccta caaatgccgc cctggatacc gaacacttgg cactattgta   1020
aaagtatgca agaatggaaa atgggtggcg tctaacccat ccaggatatg tcggaaaaag   1080
ccttgtgggc atcccggaga cacccctttt ggtccttta ggctggcagt tggatctcaa   1140
tttgagtttg gtgcaaaggt tgtttatacc tgtgatgatg gtatcaact attaggtgaa    1200
attgattacc gtgaatgtgg tgcagatggc tggatcaatg atattccact atgtgaagtt    1260
gtgaagtgtc tacctgtgac agaactcgag aatggaagaa ttgtgagtgg tgcagcagaa    1320
acagaccagg aatactattt tggacaggtg gtgcggtttg aatgcaattc aggcttcaag    1380
attgaaggac ataaggaaat tcattgctca gaaaatggcc tttggagcaa tgaaaagcca    1440
cgatgtgtgg aaattctctg cacaccaccg cgagtggaaa atggagatgg tataaatgtg    1500
aaaccagttt acaaggagaa tgaaagatac cactataagt gtaagcatgg ttatgtgccc    1560
aaagaaagag gggatgccgt ctgcacaggc tctggatgga gttctcagcc tttctgtgaa    1620
gaaaagagat gctcacctcc ttatattcta atggtatct acacacctca caggattata    1680
cacagaagtg atgatgaaat cagatatgaa tgtaattatg cttctatcc tgtaactgga    1740
tcaactgttt caagtgtac acccactggc tggatccctg ttccaagatg taccgaagat    1800
tgtaaaggtc ctcctccaag agaaaattca gaaattctct caggctcgtg gtcagaacaa   1860
ctatatccag aaggcaccca ggctacctac aaatgccgcc ctggataccg aacacttggc    1920
actattgtaa aagtatgcaa gaatggaaaa tgggtggcgt ctaacccatc aggatatgt    1980
cggaaaaagc cttgtgggca tcccggagac acccctttg gtcctttag ctggcagtt     2040
ggatctcaat ttgagtttgg tgcaaaggtt gtttatacct gtgatgatgg gtatcaacta    2100
```

-continued

```
ttaggtgaaa ttgattaccg tgaatgtggt gcagatggct ggatcaatga tattccacta   2160
tgtgaagttg tgaagtgtct acctgtgaca gaactcgaga atggaagaat gtgagtggt    2220 gcagcagaaa cagaccagga atactatttt ggacaggtgg tgcggtttga atgcaattca   2280
ggcttcaaga ttgaaggaca taaggaaatt cattgctcag aaaatggcct ttggagcaat   2340
gaaaagccac gatgtgtgga aattctctgc acaccaccgc gagtggaaaa tggagatggt   2400
ataaatgtga aaccagttta caggagaat gaaagatacc actataagtg taagcatggt    2460
tatgtgccca agaaagagg ggatgccgtc tgcacaggct ctggatggag ttctcagcct    2520
ttctgtgaag aaaagagatg ctcacctcct tatattctaa atggtatcta cacacctcac   2580
aggattatac acagaagtga tgtgaaatc agatatgaat gtaattatgg cttctatcct    2640
gtaactggat caactgtttc aaagtgtaca cccactggct ggatccctgt tccaagatgt   2700
acctaa                                                              2706
```

<210> SEQ ID NO 21
<211> LENGTH: 560
<212> TYPE: PRT
<213> ORGANISM: Homo sapiens

<400> SEQUENCE: 21

```
Ile Ser Cys Gly Ser Pro Pro Ile Leu Asn Gly Arg Ile Ser Tyr
 1               5                  10                  15

Tyr Ser Thr Pro Ile Ala Val Gly Thr Val Ile Arg Tyr Ser Cys Ser
             20                  25                  30

Gly Thr Phe Arg Leu Ile Gly Glu Lys Ser Leu Leu Cys Ile Thr Lys
         35                  40                  45

Asp Lys Val Asp Gly Thr Trp Asp Lys Pro Ala Pro Lys Cys Glu Tyr
 50                  55                  60

Phe Asn Lys Tyr Ser Ser Cys Pro Glu Pro Ile Val Pro Gly Gly Tyr
 65                  70                  75                  80

Lys Ile Arg Gly Ser Thr Pro Tyr Arg His Gly Asp Ser Val Thr Phe
             85                  90                  95

Ala Cys Lys Thr Asn Phe Ser Met Asn Gly Asn Lys Ser Val Trp Cys
        100                 105                 110

Gln Ala Asn Asn Met Trp Gly Pro Thr Arg Leu Pro Thr Cys Val Ser
    115                 120                 125

Val Phe Pro Leu Glu Cys Pro Ala Leu Pro Met Ile His Asn Gly His
130                 135                 140

His Thr Ser Glu Asn Val Gly Ser Ile Ala Pro Gly Leu Ser Val Thr
145                 150                 155                 160

Tyr Ser Cys Glu Ser Gly Tyr Leu Leu Val Gly Glu Lys Ile Ile Asn
                165                 170                 175

Cys Leu Ser Ser Gly Lys Trp Ser Ala Val Pro Thr Cys Glu Glu
            180                 185                 190

Ala Arg Cys Lys Ser Leu Gly Arg Phe Pro Asn Gly Lys Val Lys Glu
        195                 200                 205

Pro Pro Ile Leu Arg Val Gly Val Thr Ala Asn Phe Phe Cys Asp Glu
    210                 215                 220

Gly Tyr Arg Leu Gln Gly Pro Pro Ser Ser Arg Cys Val Ile Ala Gly
225                 230                 235                 240

Gln Gly Val Ala Trp Thr Lys Met Pro Val Cys Glu Glu Ile Phe Glu
                245                 250                 255
```

```
Asp Cys Asn Glu Leu Pro Pro Arg Arg Asn Thr Glu Ile Leu Thr Gly
            260                 265                 270

Ser Trp Ser Asp Gln Thr Tyr Pro Glu Gly Thr Gln Ala Ile Tyr Lys
        275                 280                 285

Cys Arg Pro Gly Tyr Arg Ser Leu Gly Asn Val Ile Met Val Cys Arg
    290                 295                 300

Lys Gly Glu Trp Val Ala Leu Asn Pro Leu Arg Lys Cys Gln Lys Arg
305                 310                 315                 320

Pro Cys Gly His Pro Gly Asp Thr Pro Phe Gly Thr Phe Thr Leu Thr
            325                 330                 335

Gly Gly Asn Val Phe Glu Tyr Gly Val Lys Ala Val Tyr Thr Cys Asn
            340                 345                 350

Glu Gly Tyr Gln Leu Leu Gly Glu Ile Asn Tyr Arg Glu Cys Asp Thr
        355                 360                 365

Asp Gly Trp Thr Asn Asp Ile Pro Ile Cys Glu Val Val Lys Cys Leu
    370                 375                 380

Pro Val Thr Ala Pro Glu Asn Gly Lys Ile Val Ser Ser Ala Met Glu
385                 390                 395                 400

Pro Asp Arg Glu Tyr His Phe Gly Gln Ala Val Arg Phe Val Cys Asn
            405                 410                 415

Ser Gly Tyr Lys Ile Glu Gly Asp Glu Met His Cys Ser Asp Asp
            420                 425                 430

Gly Phe Trp Ser Lys Glu Lys Pro Lys Cys Val Glu Ile Ser Cys Lys
    435                 440                 445

Ser Pro Asp Val Ile Asn Gly Ser Pro Ile Ser Gln Lys Ile Ile Tyr
    450                 455                 460

Lys Glu Asn Glu Arg Phe Gln Tyr Lys Cys Asn Met Gly Tyr Glu Tyr
465                 470                 475                 480

Ser Glu Arg Gly Asp Ala Val Cys Thr Glu Ser Gly Trp Arg Pro Leu
            485                 490                 495

Pro Ser Cys Glu Glu Lys Ser Cys Asp Asn Pro Tyr Ile Pro Asn Gly
            500                 505                 510

Asp Tyr Ser Pro Leu Arg Ile Lys His Arg Thr Gly Asp Glu Ile Thr
            515                 520                 525

Tyr Gln Cys Arg Asn Gly Phe Tyr Pro Ala Thr Arg Gly Asn Thr Ala
    530                 535                 540

Lys Cys Thr Ser Thr Gly Trp Ile Pro Ala Pro Arg Cys Thr Leu Lys
545                 550                 555                 560

<210> SEQ ID NO 22
<211> LENGTH: 1755
<212> TYPE: DNA
<213> ORGANISM: Homo sapiens

<400> SEQUENCE: 22
gccgccacca tgggagccgc tggtctgctc ggcgtgttcc tcgccttggt ggcacctggc      60
gtcctgggca tcagctgcgg ttcccctcca ccaatcctga atggcagaat ctcctattac     120
tccacaccaa tcgccgtcgg cactgtgatc agatacagct gttcagggac ttttcggctg     180
atcggcgaga aaagcctcct ctgcattacc aaggataagg tcgatgggac atgggataaa     240
ccagctccta agtgcgagta cttcaataag tatagttcat gtccagagcc cattgttcct     300
ggtggctaca gattcggggg agcacaccc tatcgccacg tgactcagt gacctttgct     360 tgtaaaacca acttctcaat gaacggtaat aagtcagtgt ggtgtcaggc caataatatg     420
```

```
tggggtccta cacgactccc cacctgtgtg tccgtgttcc ccttggaatg ccccgccctg    480
cccatgatcc ataatggaca ccacaccagc gagaatgtcg ggagtatcgc acctggattg    540
agtgtcacct actcatgcga gtctggctac ctgcttgtag gtgaaaaaat tattaattgc    600
ttgtcctccg gcaaatggag tgccgttccc ccaacttgtg aagaggcccg gtgcaaatcc    660
ctcggccgct tccctaatgg taaagttaaa gagcctccaa tcctcagagt ggggtgacc     720 gctaacttct tctgtgatga aggctaccgg ttgcaggggac acccagtag ccggtgtgtc    780 atagctgggc agggagtggc ttggacaaag atgcccgttt gtgaggaaat cttcgaagac    840
tgtaatgagc tgccccccaag acggaataca gagatcctca caggctcttg gtccgatcaa    900
acttatccag agggtaccca ggcaatttac aagtgcagac ctggatacag gagcctgggc    960
aatgtgatta tggtgtgccg caaggggggag tgggtggccc ttaatcctct ccggaagtgt    1020
cagaaaagac catgcggaca ccctggagat acacctttcg gtacctttac ccttaccggc    1080
ggcaatgtct tcgagtatgg cgtcaaggcc gtgtacactt gtaacgaggg ataccagctg    1140
ctgggggaaa taaactatcg tgagtgtgac actgacgggt ggactaacga catccccatt    1200
tgcgaggtgg tcaagtgcct tcctgtaacc gctcccgaaa atggtaagat cgtatcttcc    1260
gcaatggagc ctgatcggga ataccacttt ggacaagccg ttcggttcgt atgtaattca    1320
gggtataaaa ttgagggcga tgaggagatg cactgcagtg atgacggctt ttggtcaaag    1380
gaaaagccaa agtgcgtaga gatcagttgt aagtctcctg acgttattaa cgggagtccc    1440
atcagtcaga agatcattta caaggaaaac gagaggttcc agtataaatg caatatggga    1500
tatgagtact ccgaaagagg ggacgccgtg tgcacagagt ccggatggcg accttttgcca    1560 tcttgtgaag aaaagtcttg tgacaacccc tatattccta acggagatta ctctcctctg    1620
cgcatcaagc accgaactgg ggacgagatc acttaccaat gtcgaaacgg cttctaccct    1680
gctaccagag gtaacactgc caagtgtacc agcaccggtt ggattcccgc ccccagatgc    1740
acacttaaat gataa                                                    1755
```

<210> SEQ ID NO 23
<211> LENGTH: 863
<212> TYPE: PRT
<213> ORGANISM: Homo sapiens

<400> SEQUENCE: 23

```
Ile Ser Cys Gly Ser Pro Pro Ile Leu Asn Gly Arg Ile Ser Tyr
  1               5                  10                  15

Tyr Ser Thr Pro Ile Ala Val Gly Thr Val Ile Arg Tyr Ser Cys Ser
            20                  25                  30

Gly Thr Phe Arg Leu Ile Gly Glu Lys Ser Leu Leu Cys Ile Thr Lys
        35                  40                  45

Asp Lys Val Asp Gly Thr Trp Asp Lys Pro Ala Pro Lys Cys Glu Tyr
    50                  55                  60

Phe Asn Lys Tyr Ser Ser Cys Pro Glu Pro Ile Val Pro Gly Gly Tyr
65                  70                  75                  80

Lys Ile Arg Gly Ser Thr Pro Tyr Arg His Gly Asp Ser Val Thr Phe
                85                  90                  95

Ala Cys Lys Thr Asn Phe Ser Met Asn Gly Asn Lys Ser Val Trp Cys
            100                 105                 110

Gln Ala Asn Asn Met Trp Gly Pro Thr Arg Leu Pro Thr Cys Val Ser
        115                 120                 125

Val Phe Pro Leu Glu Cys Pro Ala Leu Pro Met Ile His Asn Gly His
```

-continued

```
            130                 135                 140
His Thr Ser Glu Asn Val Gly Ser Ile Ala Pro Gly Leu Ser Val Thr
145                 150                 155                 160

Tyr Ser Cys Glu Ser Gly Tyr Leu Leu Val Gly Glu Lys Ile Ile Asn
                165                 170                 175

Cys Leu Ser Ser Gly Lys Trp Ser Ala Val Pro Pro Thr Cys Glu Glu
                180                 185                 190

Ala Arg Cys Lys Ser Leu Gly Arg Phe Pro Asn Gly Lys Val Lys Glu
                195                 200                 205

Pro Pro Ile Leu Arg Val Gly Val Thr Ala Asn Phe Phe Cys Asp Glu
210                 215                 220

Gly Tyr Arg Leu Gln Gly Pro Pro Ser Ser Arg Cys Val Ile Ala Gly
225                 230                 235                 240

Gln Gly Val Ala Trp Thr Lys Met Pro Val Cys Glu Ile Phe Glu
                245                 250                 255

Asp Cys Asn Glu Leu Pro Pro Arg Asn Thr Glu Ile Leu Thr Gly
                260                 265                 270

Ser Trp Ser Asp Gln Thr Tyr Pro Glu Gly Thr Gln Ala Ile Tyr Lys
                275                 280                 285

Cys Arg Pro Gly Tyr Arg Ser Leu Gly Asn Val Ile Met Val Cys Arg
                290                 295                 300

Lys Gly Glu Trp Val Ala Leu Asn Pro Leu Arg Lys Cys Gln Lys Arg
305                 310                 315                 320

Pro Cys Gly His Pro Gly Asp Thr Pro Phe Gly Thr Phe Thr Leu Thr
                325                 330                 335

Gly Gly Asn Val Phe Glu Tyr Gly Val Lys Ala Val Tyr Thr Cys Asn
                340                 345                 350

Glu Gly Tyr Gln Leu Leu Gly Glu Ile Asn Tyr Arg Glu Cys Asp Thr
                355                 360                 365

Asp Gly Trp Thr Asn Asp Ile Pro Ile Cys Glu Val Val Lys Cys Leu
                370                 375                 380

Pro Val Thr Ala Pro Glu Asn Gly Lys Ile Val Ser Ser Ala Met Glu
385                 390                 395                 400

Pro Asp Arg Glu Tyr His Phe Gly Gln Ala Val Arg Phe Val Cys Asn
                405                 410                 415

Ser Gly Tyr Lys Ile Glu Gly Asp Glu Glu Met His Cys Ser Asp Asp
                420                 425                 430

Gly Phe Trp Ser Lys Glu Lys Pro Lys Cys Val Glu Ile Ser Cys Lys
                435                 440                 445

Ser Pro Asp Val Ile Asn Gly Ser Pro Ile Ser Gln Lys Ile Ile Tyr
450                 455                 460

Lys Glu Asn Glu Arg Phe Gln Tyr Lys Cys Asn Met Gly Tyr Glu Tyr
465                 470                 475                 480

Ser Glu Arg Gly Asp Ala Val Cys Thr Glu Ser Gly Trp Arg Pro Leu
                485                 490                 495

Pro Ser Cys Glu Glu Lys Ser Cys Asp Asn Pro Tyr Ile Pro Asn Gly
                500                 505                 510

Asp Tyr Ser Pro Leu Arg Ile Lys His Arg Thr Gly Asp Glu Ile Thr
                515                 520                 525

Tyr Gln Cys Arg Asn Gly Phe Tyr Pro Ala Thr Arg Gly Asn Thr Ala
                530                 535                 540

Lys Cys Thr Ser Thr Gly Trp Ile Pro Ala Pro Arg Cys Thr Glu Asp
545                 550                 555                 560
```

Cys Asn Glu Leu Pro Arg Arg Asn Thr Glu Ile Leu Thr Gly Ser
                565                 570                 575

Trp Ser Asp Gln Thr Tyr Pro Glu Gly Thr Gln Ala Ile Tyr Lys Cys
            580                 585                 590

Arg Pro Gly Tyr Arg Ser Leu Gly Asn Val Ile Met Val Cys Arg Lys
        595                 600                 605

Gly Glu Trp Val Ala Leu Asn Pro Leu Arg Lys Cys Gln Lys Arg Pro
    610                 615                 620

Cys Gly His Pro Gly Asp Thr Pro Phe Gly Thr Phe Thr Leu Thr Gly
625                 630                 635                 640

Gly Asn Val Phe Glu Tyr Gly Val Lys Ala Val Tyr Thr Cys Asn Glu
                645                 650                 655

Gly Tyr Gln Leu Leu Gly Glu Ile Asn Tyr Arg Glu Cys Asp Thr Asp
            660                 665                 670

Gly Trp Thr Asn Asp Ile Pro Ile Cys Glu Val Val Lys Cys Leu Pro
        675                 680                 685

Val Thr Ala Pro Glu Asn Gly Lys Ile Val Ser Ser Ala Met Glu Pro
    690                 695                 700

Asp Arg Glu Tyr His Phe Gly Gln Ala Val Arg Phe Val Cys Asn Ser
705                 710                 715                 720

Gly Tyr Lys Ile Glu Gly Asp Glu Glu Met His Cys Ser Asp Asp Gly
                725                 730                 735

Phe Trp Ser Lys Glu Lys Pro Lys Cys Val Glu Ile Ser Cys Lys Ser
            740                 745                 750

Pro Asp Val Ile Asn Gly Ser Pro Ile Ser Gln Lys Ile Ile Tyr Lys
        755                 760                 765

Glu Asn Glu Arg Phe Gln Tyr Lys Cys Asn Met Gly Tyr Glu Tyr Ser
    770                 775                 780

Glu Arg Gly Asp Ala Val Cys Thr Glu Ser Gly Trp Arg Pro Leu Pro
785                 790                 795                 800

Ser Cys Glu Glu Lys Ser Cys Asp Asn Pro Tyr Ile Pro Asn Gly Asp
                805                 810                 815

Tyr Ser Pro Leu Arg Ile Lys His Arg Thr Gly Asp Glu Ile Thr Tyr
            820                 825                 830

Gln Cys Arg Asn Gly Phe Tyr Pro Ala Thr Arg Gly Asn Thr Ala Lys
        835                 840                 845

Cys Thr Ser Thr Gly Trp Ile Pro Ala Pro Arg Cys Thr Leu Lys
    850                 855                 860

<210> SEQ ID NO 24
<211> LENGTH: 2665
<212> TYPE: DNA
<213> ORGANISM: Homo sapiens

<400> SEQUENCE: 24
cgccgccacc atgggcgcag caggcttgtt gggcgtgttc ctggcattgg tggcacccgg      60
cgtattgggc atttcatgcg gctctcctcc acccattctc aatggaagga tctcctacta     120
cagcaccccc atagctgtcg gcaccgttat ccgatacagt tgttccggta ctttccggct     180
tatcggcgaa aagtctttgc tgtgcattac caaggataaa gtggacggga cttgggacaa     240
acccgcacct aagtgcgagt attttaacaa atatagcagc tgccctgagc ctatagtacc     300
cggggggtat aaaatccggg gctctactcc ctatcgtcat ggcgattctg tgaccttcgc     360
atgtaaaact aattttttcaa tgaatggcaa caagtctgta tggtgtcaag caaataacat     420

```
gtggggacct acccgcctgc caacctgtgt gtcagtgttt ccctggaat gtccagccct      480
ccctatgatc cacaacggac atcacaccag cgaaaacgtt ggatccatcg caccagggct    540
ctctgtgact tactcttgcg agtccgggta cctgctcgtg ggtgaaaaga tcatcaactg    600
cctcagtagt ggtaaatggt ccgccgtgcc tcccacatgt gaagaggccc ggtgcaagag    660
cctgggccgg ttccccaacg gaaaagtgaa ggaacctcct atcttgaggg ttggtgtgac    720
cgctaacttt ttctgcgacg aggggtacag gctccaaggg cctccctcta gtcggtgcgt    780
aatcgccggt caaggagtcg catggactaa gatgcctgtg tgtgaggaga ttttcgagga    840
ttgtaatgaa ttgccaccca ggagaaatac tgaaatcctg acaggctctt ggtctgatca    900
gacttatcca gaaggcaccc aggccattta caagtgtcgg cctggataca gatctctggg    960
aaatgtgatc atggtatgta ggaaaggaga gtgggtggct ttgaaccccc tccgcaagtg   1020
tcagaaaaga ccatgcgggc atcctggaga cacccccattc gggacattta cactgacagg   1080
cggaaacgta tttgagtacg gagtcaaggc cgtttataca tgtaacgaag ggtatcaact   1140
gctgggagaa atcaactata gggagtgcga cactgacgga tggacaaacg acattccaat   1200
ctgcgaagtg gtgaaatgtc ttccagttac agcccctgaa aacgggaaaa tcgtgtcctc   1260
cgctatggag cctgaccggg aatatcattt cggccaggcc gttagattcg tgtgtaatag   1320
cggctacaaa atcgagggcg acgaagaaat gcattgcagc gatgacgggt tctggagcaa   1380
ggagaagcct aaatgcgtcg aaatttcatg caagagtccc gacgtcataa acggttctcc   1440
aatttcccag aagatcattt ataaggagaa tgagcggttc cagtataagt gtaatatggg   1500
ctacgagtac agcgaacgcg gtgacgccgt gtgtaccgaa agtggctgga gaccactgcc   1560
tagttgcgag gagaaatcct gcgacaaccc ttatattccc aacggggact actctcctct   1620
gagaatcaag catcggactg gcgacgagat tacttaccaa tgcaggaacg gattctatcc   1680
agcaactcgg ggcaataccg ctaagtgtac ctccacaggc tggataccgg ctcctagatg   1740
tacagaggac tgcaatgaac tgccacctcg gcgcaataca gaaattttga ctggatcatg   1800
gtctgaccag acttaccccg agggcaccca ggccatctac aaatgtaggc ccggttatcg   1860
aagtttgggt aacgtgatta tggtgtgtcg aaaaggtgaa tgggtagcac tcaatcccct   1920
ccgtaaatgc cagaagcgtc cttgtgggca cccaggcgat accccttttg aactttcac   1980
cctgactgga ggaaacgtct ttgaatatgg tgtgaaagcc gtgtacacat gcaatgaagg   2040
gtaccaactg ctcggagaga taaactatcg ggagtgcgat acagatggat ggaccaatga   2100
tataccaatc tgcgaggtgg tgaagtgtct cccagtcacc gctcctgaga acggaaagat   2160
cgtcagttct gctatggaac ctgacaggga ataccacttt gggcaagccg tccgcttcgt   2220
gtgcaattca gggtacaaga tagaaggcga cgaagagatg cactgttccg acgatggttt   2280
ctggtctaag gagaagccta aatgtgtcga gattagctgc aagtctcccg atgttattaa   2340
cggctctccc atctctcaaa aaattattta taaggaaaac gaaagatttc agtacaagtg   2400
caatatgggt tatgagtaca gtgaacgtgg agacgccgtg tgcacagagt ccgggtggcg   2460
tccactgccc agctgcgaag aaaaatcctg tgacaacccc tacatcccca atggcgacta   2520
ttcccccctg cgcatcaaac atcgtactgg cgatgaaatt acttaccagt gccgcaacgg   2580
gttctaccct gccacccggg gtaacacagc caaatgcacc tccaccggat ggatccccgc   2640
cccacgctgt accttgaaat gatga                                         2665
```

<210> SEQ ID NO 25

-continued

```
<211> LENGTH: 20
<212> TYPE: PRT
<213> ORGANISM: Homo sapiens
<220> FEATURE:
<221> NAME/KEY: VARIANT
<222> LOCATION: (1)...(20)
<223> OTHER INFORMATION: signal peptide

<400> SEQUENCE: 25

Met Gly Ala Ala Gly Leu Leu Gly Val Phe Leu Ala Leu Val Ala Pro
 1               5                  10                  15

Gly Val Leu Gly
            20

<210> SEQ ID NO 26
<211> LENGTH: 60
<212> TYPE: DNA
<213> ORGANISM: Homo sapiens
<220> FEATURE:
<221> NAME/KEY: misc_feature
<222> LOCATION: (1)...(60)
<223> OTHER INFORMATION: signal peptide

<400> SEQUENCE: 26
atgggagccg ctggtctgct cggcgtgttc ctcgccttgg tggcacctgg cgtcctgggc     60
```